US010543357B2

(12) United States Patent
Kreis et al.

(10) Patent No.: US 10,543,357 B2
(45) Date of Patent: Jan. 28, 2020

(54) HIGH VOLTAGE CONNECTORS FOR PULSE GENERATORS

(71) Applicant: PULSE BIOSCIENCES, INC., Burlingame, CA (US)

(72) Inventors: Mark P. Kreis, San Francisco, CA (US); David J. Danitz, San Jose, CA (US); Cameron Dale Hinman, Thurmond, NC (US); Sean Nicholas Finson, Santa Clara, CA (US)

(73) Assignee: PULSE BIOSCIENCES, INC., Hayward, CA (US)

( * ) Notice: Subject to any disclaimer, the term of this patent is extended or adjusted under 35 U.S.C. 154(b) by 363 days.

(21) Appl. No.: 15/269,273

(22) Filed: Sep. 19, 2016

(65) Prior Publication Data

US 2018/0078755 A1    Mar. 22, 2018

(51) Int. Cl.
*A61B 18/14* (2006.01)
*A61N 1/05* (2006.01)
(Continued)

(52) U.S. Cl.
CPC ........ *A61N 1/0502* (2013.01); *A61B 18/1477* (2013.01); *A61N 1/0472* (2013.01);
(Continued)

(58) Field of Classification Search
CPC .......... A61N 1/0472; A61B 2018/1495; A61B 2018/00178; A61B 2018/0091
See application file for complete search history.

(56) References Cited

U.S. PATENT DOCUMENTS

| 5,568,035 A | 10/1996 | Kato et al. |
| 5,635,776 A | 6/1997 | Imi |

(Continued)

FOREIGN PATENT DOCUMENTS

| WO | 2011/146498 A2 | 11/2011 |
| WO | 2014/060854 A1 | 4/2014 |

(Continued)

OTHER PUBLICATIONS

Garon et al., "In Vitro and In Vivo Evaluation and a Case Report of Intense Nanosecond Pulsed Electric Field as a Local Therapy for Human Malignancies", Int. J. Cancer, vol. 121, 2007, pp. 675-682.

(Continued)

*Primary Examiner* — George R Evanisko
(74) *Attorney, Agent, or Firm* — Kilpatrick Townsend & Stockton LLP

(57) ABSTRACT

An electrode connectable to a pulse generator is disclosed. The electrode includes therapeutic terminals configured to deliver the pulse to a patient, first and second electrical pulse inlet holes, and a first pulse input terminal. The first pulse input terminal is in the first electrical pulse inlet hole and is spaced apart from an entrance to the first electrical pulse inlet hole by more than about 2.5 cm. Also, first pulse input terminal is connected with one or more of the therapeutic terminals. The electrode also includes a second pulse input terminal, where the second pulse input terminal is in the second electrical pulse inlet hole and is spaced apart from an entrance to the second electrical pulse inlet hole by a distance greater than about 2.5 cm. Also, the second pulse input terminal is electrically connected with one or more of the therapeutic terminals.

25 Claims, 58 Drawing Sheets

(51) Int. Cl.
*A61N 1/04* (2006.01)
*A61N 1/32* (2006.01)
*A61N 1/36* (2006.01)

(52) U.S. Cl.
CPC ............... *A61N 1/32* (2013.01); *A61N 1/36* (2013.01); *A61N 1/36017* (2013.01); *A61B 2018/1495* (2013.01)

(56) References Cited

U.S. PATENT DOCUMENTS

| | | | |
|---|---|---|---|
| 5,774,348 A | 6/1998 | Druce et al. | |
| 5,902,272 A * | 5/1999 | Eggers | A61B 18/12 604/114 |
| 5,907,484 A | 5/1999 | Kowshik et al. | |
| 6,008,690 A | 12/1999 | Takeshima et al. | |
| 6,017,354 A * | 1/2000 | Culp | A61B 17/1626 604/22 |
| 6,026,003 A | 2/2000 | Moore et al. | |
| 6,048,789 A | 4/2000 | Vines et al. | |
| 6,137,276 A | 10/2000 | Rudolph | |
| 6,190,381 B1 * | 2/2001 | Olsen | A61B 18/12 604/114 |
| 6,326,177 B1 | 12/2001 | Schoenbach et al. | |
| 6,831,377 B2 | 12/2004 | Yampolsky et al. | |
| 7,496,401 B2 | 2/2009 | Bernabei | |
| 7,767,433 B2 | 8/2010 | Kuthi et al. | |
| 7,855,904 B2 | 12/2010 | Kirbie et al. | |
| 7,937,143 B2 | 5/2011 | Demarais et al. | |
| 8,688,227 B2 | 4/2014 | Nuccitelli et al. | |
| 8,822,222 B2 | 9/2014 | Beebe et al. | |
| 9,101,337 B2 * | 8/2015 | Hoegerle | A61B 17/1622 |
| 9,724,155 B2 | 8/2017 | Nuccitelli et al. | |
| 2001/0025177 A1 | 9/2001 | Woloszko et al. | |
| 2002/0193833 A1 | 12/2002 | Dimmer et al. | |
| 2003/0204161 A1 | 10/2003 | Ferek-Petric | |
| 2003/0233087 A1 * | 12/2003 | Chen | A61B 18/14 606/41 |
| 2004/0080964 A1 | 4/2004 | Buchmann | |
| 2004/0240241 A1 | 12/2004 | Chueh et al. | |
| 2006/0062074 A1 | 3/2006 | Gundersen et al. | |
| 2006/0079886 A1 | 4/2006 | Orszulak et al. | |
| 2006/0090723 A1 | 5/2006 | Stuart | |
| 2006/0139977 A1 | 6/2006 | Oicles et al. | |
| 2007/0066957 A1 | 3/2007 | Demarais et al. | |
| 2007/0129626 A1 | 6/2007 | Mahesh et al. | |
| 2008/0031337 A1 | 2/2008 | Hasegawa et al. | |
| 2008/0077189 A1 | 3/2008 | Ostroff | |
| 2009/0198231 A1 | 8/2009 | Esser et al. | |
| 2009/0299362 A1 | 12/2009 | Long et al. | |
| 2010/0038971 A1 | 2/2010 | Sanders et al. | |
| 2010/0042095 A1 | 2/2010 | Bigley et al. | |
| 2010/0063496 A1 | 3/2010 | Trovato et al. | |
| 2010/0240995 A1 | 9/2010 | Nuccitelli | |
| 2010/0318082 A1 | 12/2010 | Nuccitelli et al. | |
| 2010/0331758 A1 | 12/2010 | Davalos et al. | |
| 2011/0015630 A1 | 1/2011 | Azure | |
| 2011/0118729 A1 | 5/2011 | Heeren et al. | |
| 2011/0144641 A1 | 6/2011 | Dimalanta et al. | |
| 2011/0160514 A1 | 6/2011 | Long et al. | |
| 2011/0270249 A1 | 11/2011 | Utley et al. | |
| 2012/0277763 A1 | 11/2012 | Greenblatt et al. | |
| 2012/0310230 A1 | 12/2012 | Willis et al. | |
| 2012/0315704 A1 | 12/2012 | Beebe et al. | |
| 2013/0018441 A1 | 1/2013 | Childs | |
| 2013/0150935 A1 | 6/2013 | Weissberg et al. | |
| 2013/0302409 A1 | 11/2013 | Fuchs et al. | |
| 2013/0345697 A1 | 12/2013 | Garcia et al. | |
| 2014/0046322 A1 | 2/2014 | Callas et al. | |
| 2014/0081256 A1 * | 3/2014 | Carmel | A61B 18/18 606/33 |
| 2014/0228835 A1 | 8/2014 | Mielekamp et al. | |
| 2014/0277219 A1 | 9/2014 | Nanda | |
| 2014/0336638 A1 | 11/2014 | Deem et al. | |
| 2014/0358066 A1 | 12/2014 | Nuccitelli et al. | |
| 2015/0032100 A1 | 1/2015 | Coulson et al. | |
| 2015/0065946 A1 | 3/2015 | Gehl et al. | |
| 2015/0272657 A1 | 10/2015 | Yates et al. | |
| 2017/0245928 A1 | 8/2017 | Xiao et al. | |
| 2017/0246455 A1 | 8/2017 | Athos et al. | |
| 2017/0319851 A1 | 11/2017 | Athos et al. | |
| 2017/0326361 A1 | 11/2017 | Kreis | |
| 2017/0360504 A1 | 12/2017 | Nuccitelli et al. | |
| 2018/0110557 A1 | 4/2018 | Muratori et al. | |
| 2018/0154142 A1 | 6/2018 | Guo et al. | |

FOREIGN PATENT DOCUMENTS

| | | |
|---|---|---|
| WO | 2016/089781 A1 | 6/2016 |
| WO | 2017/151260 A1 | 9/2017 |
| WO | 2017/151261 A1 | 9/2017 |
| WO | 2017/201394 A1 | 11/2017 |
| WO | 2017200954 A1 | 11/2017 |
| WO | 2018/053539 A1 | 3/2018 |
| WO | 2018/075946 A1 | 4/2018 |
| WO | 2018/089506 A1 | 5/2018 |

OTHER PUBLICATIONS

Gundersen et al., "Nanosecond Pulse Generator Using a Fast Recovery Diode", IEEE 26.sup.th Power Modulator Conference, 2004, pp. 603-606.
International Application No. PCT/US2015/63025, International Search Report and Written Opinion dated Apr. 21, 2016, 9 pages.
Nader Yatim et al., "RIPK1 and NF-κB signaling in dying cells determines cross-priming of CD8+ T cells," Science, Oct. 2015, vol. 350, Issue 6258, pp. 328-335, sciencemag.org.
PCT/US2017/052340, "International Search Report and Written Opinion", dated Jan. 8, 2018, 12 pages.
Tang et al., "Diode Opening Switch Based Nanosecond High Voltage Pulse Generators for Biological and Medical Applications", IEEE Transactions on Dielectrics and Electrical Insulation, vol. 14, No. 4, 2007, pp. 878-883.
Wang et al., "Solid-State High Voltage Nanosecond Pulse Generator," IEEE Pulsed Power Conference, 2005, pp. 1199-1202.
PCT/US2017/060654, "International Search Report and Written Opinion," dated Feb. 27, 2018, 18 pages.
International Application No. PCT/US2017/015881, Invitation to Pay Additional Fees and, Where Applicable, Protest Fee, dated Mar. 15, 2017, 2 pages.
PCT/US2017//032744, "International Search Report and Written Opinion," dated Jul. 21, 2017, 11 pages.
R. J. Baker et al., "Stacking Power MOSFETs for use in High Speed Instrumentation," Rev. Sci. Instrum. 63 (12), Dec. 1992, p. 5799-5801, vol. 63, No. 12, American Institute of Physics.
H. Kirbie et al., "An All Solid State Pulse Power Source for High PRF Induction Accselerators," IEEE 1998, p. 6-11.
K. Okamura et al. "Development of the High Repetitive Impulse Voltage Generator Using Semiconductor Switches," IEEE 1999, p. 807-810.
A. Krasnykh et al., "A Solid Stale Marx Type Modulator for Driving a TWT," Conference Record of the 24th International Power Modulator Sypolsium 2000, p. 209-211.
R.J. Richter-Sand et al., "Marx-Stacked IGBT Modulators for High Voltage, High Power Applications," IEEE 2002, p. 390-393.
Marcel P.J. Gaudreau et al., "Solid-State Pulsed Power Systems for the Next Linear Collider," IEEE 2002, p. 298-301.
E.G. Cook et al., "Design and Testing of a Fast, 50 kV Solid-Slate Kicker Pulser," IEEE 2002, p. 106-109.
Jeffrey A. Casey et al., "Solid-State Marx Bank Modulator for the Next Generation Linear Collider," Conference Record of the 26th International Power Modulator Symposium and 2004 High Voltage Workshop (PMC), San Francisco, California, May 23-26, 2004, IEEE 2004, p. 257-260.
W. Jiang et al., "Marx Generator Using Power Mosfets," IEEE 2009, p. 408-410.
Chenguo Yao et al., "FPGA-Controlled All-Solid-State Nanosecond Pulse Generator for Biological Applications," IEEE Transactions on Plasma Science, vol. 40, No. 10, Oct. 2012, p. 2366-2372.

(56) References Cited

OTHER PUBLICATIONS

Martin Sack et al., "Design Considerations for a Fast Slacked-MOSFET Switch," IEEE Transactions on Plasma Science, vol. 41, No. 10, Oct. 2013, p. 2630-2636.

Harshada C. Bhosale et al., "Design and Simulation of 50 kV. 50 A Solid State Marx Generator," International Conference on Magnetics, Machines & Drives (AICERA—2014 iCMMD), IEEE 2014, p. 1-5.

L. M. Redondo et al., "Solid-State Marx Generator Design with an Energy Recovery Reset Circuit for Output Transformer Association" 5 pages.

W. J. Carey et al., "Marx Generator Design and Performance," Applied Physical Electronics, L.C., 4 pages.

PCT/US2017/015884, "International Search Report and Written Opinion" dated Apr. 21, 2017, 12 pages.

PCT/US2017/015881, "International Search Report and Written Opinion" dated May 25, 2017, 13 pages.

Anand et al., "Adaptive Immune Response to Nano-Pulse Stimulation (NPS), Nov. 11, 2016, Poster presentation at the 31st Annual Meeting and Associated Programs of the Society for Immunotherapy of Cancer," Retrieved from the Internet: URL: http://pulsebiosciences.com/assets/Pulse%20AIR%20poster.pdf, retrieved on Mar. 13, 2018.

Anand et al., "Nano-Pulse Electro-Signaling treatment of murine tumors significantly reduces the percentage of regulatory T cells in the treated tumor," Journal for Immunotherapy of Cancer: 31st Annual Meeting and Associated Programs of the Society for Immunotherapy of Cancer (SITC 2016), Part Two, National Harbor, MD, USA Nov. 16, 2016, p. 214.

Beebe, S. J., "Hepatocellular carcinoma ablation and possible immunity in the age of nanosecond pulsed electric fields," Journal of Hepatocellular Carcioma, May 2015, No. 2, pp. 49-55.

Mcdaniel et al., "Nanosecond pulsed electric field treatment of tumor cell lines triggers immunogenic cell death (ICD)," Nov. 11, 2016, Poster presentation at the 31st Annual Meeting and Associated Programs of the Society for Immunotherapy of Cancer (SITC 2016), National Harbor, MD, USA; Retrieved from the Internet: URL: http://pulsebiosciences.com/assets/Pulse%20ICD%20poster.pdf, retrieved on Mar. 13, 2018.

Mcdaniel et al., "P329 Nanosecond pulsed electric field treatment of tumor cell lines triggers immunogenic cell death (ICD)," Journal for ImmunoTherapy of Cancer: 31st Annual Meeting and Associated Programs of the Society for Immunotherapy of Cancer (SITC 2016): part two: National Harbor, MD, USA, Nov. 16, 2016, p. 175.

PCT/US2017/057698, "International Search Report" dated Feb. 27, 2018, 3 pages.

PCT/US2017/064685, "International Search Report" dated Mar. 22, 2018, 5 pages.

PCT/US2018/019213, "International Search Report" dated May 22, 2018, 4 pages.

Australian Application No. 2017326703, Examination Report No. 1 dated Aug. 29, 2019, 6 pages.

International Application No. PCT/US2017/052340, International Preliminary Report on Patentability, dated Mar. 19, 2019, 6 pages.

\* cited by examiner

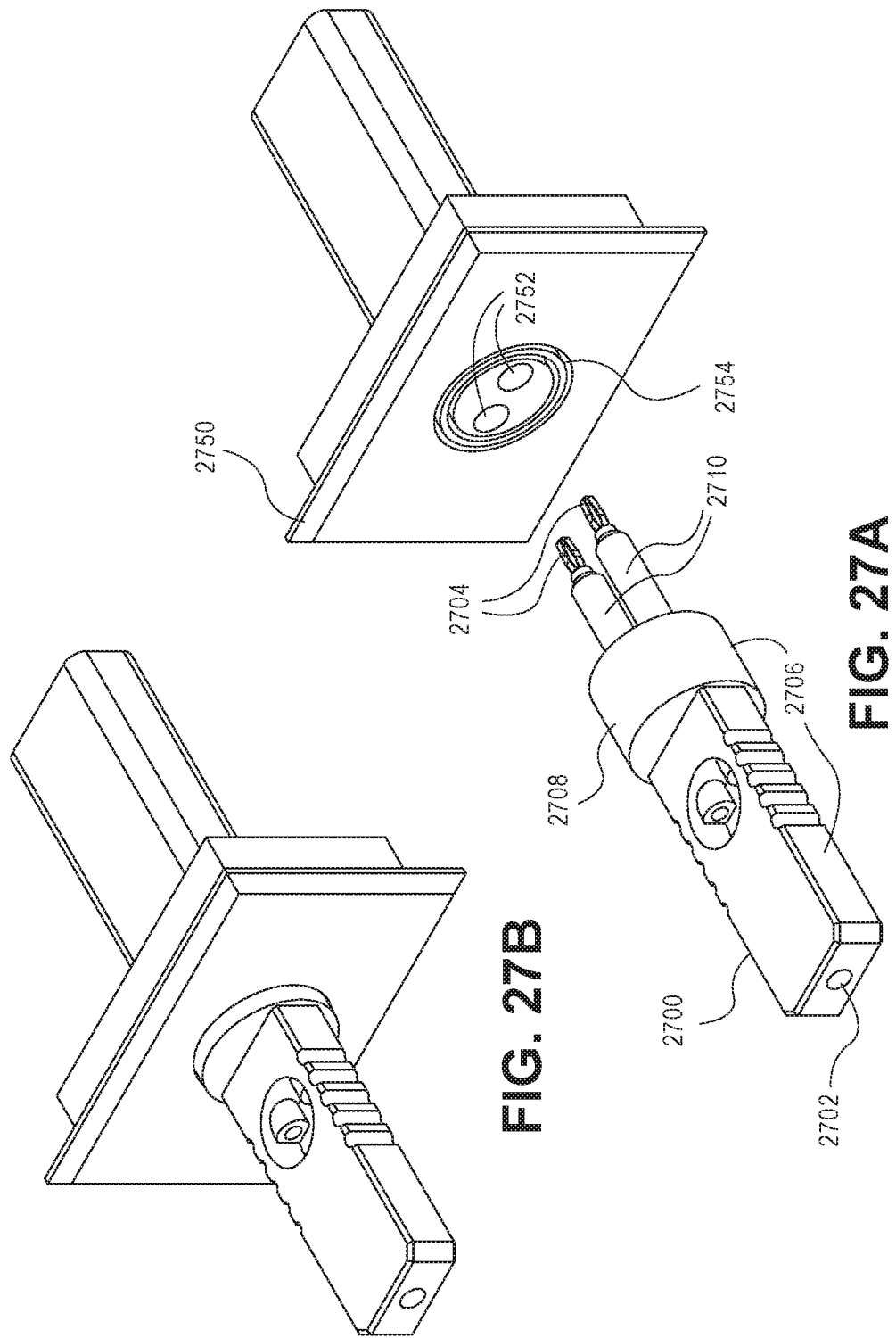

DETAIL H

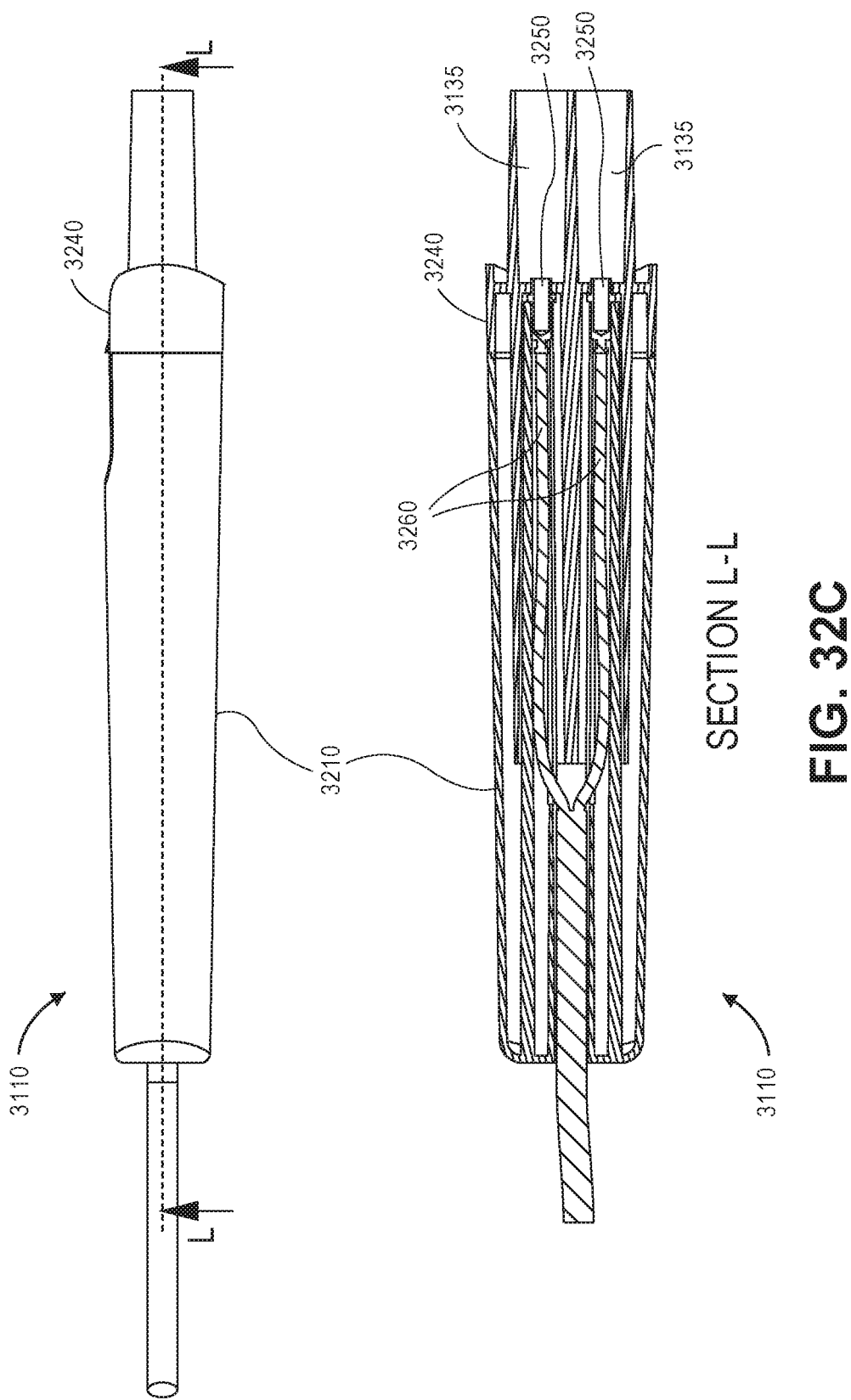

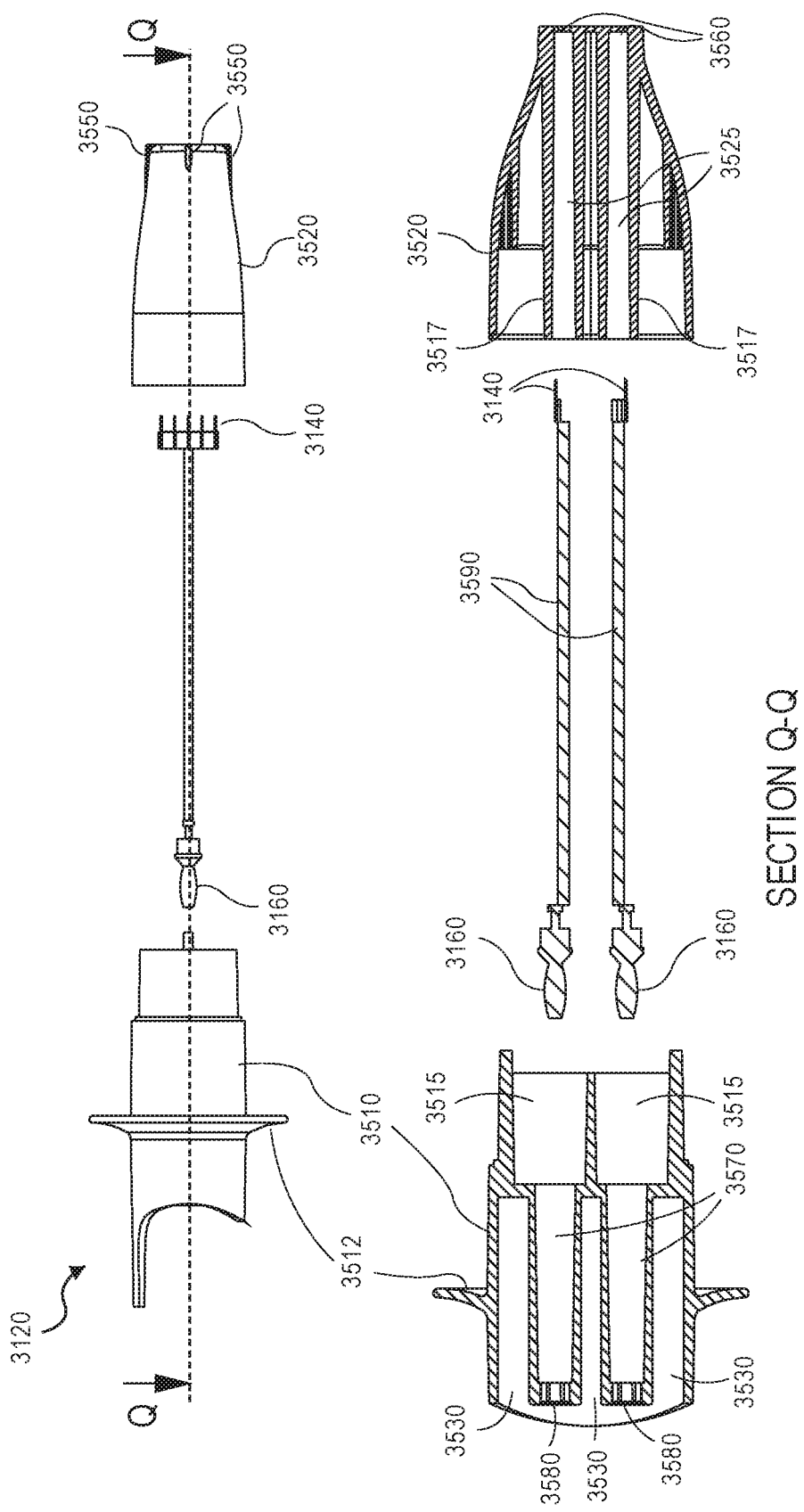

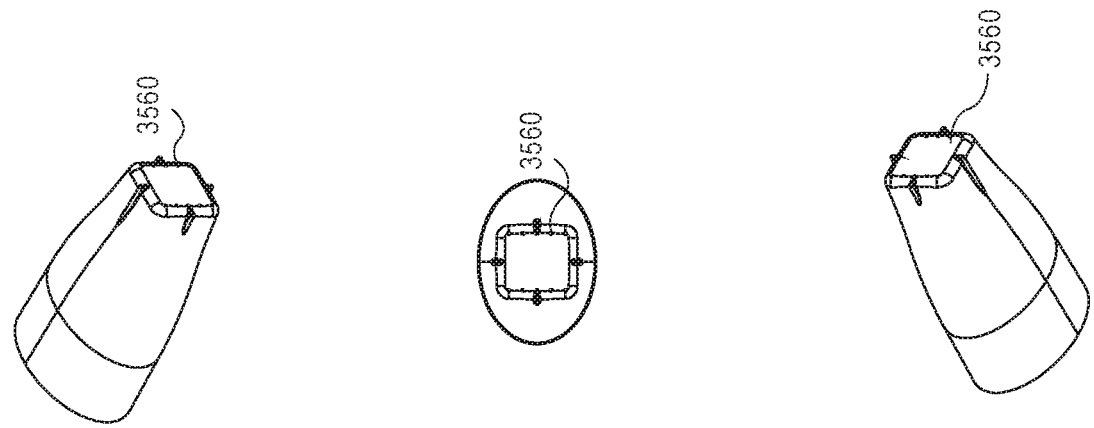
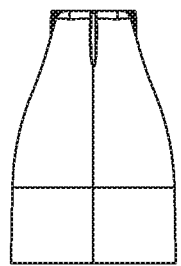  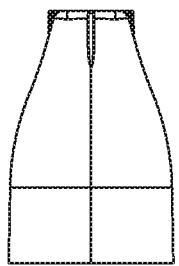
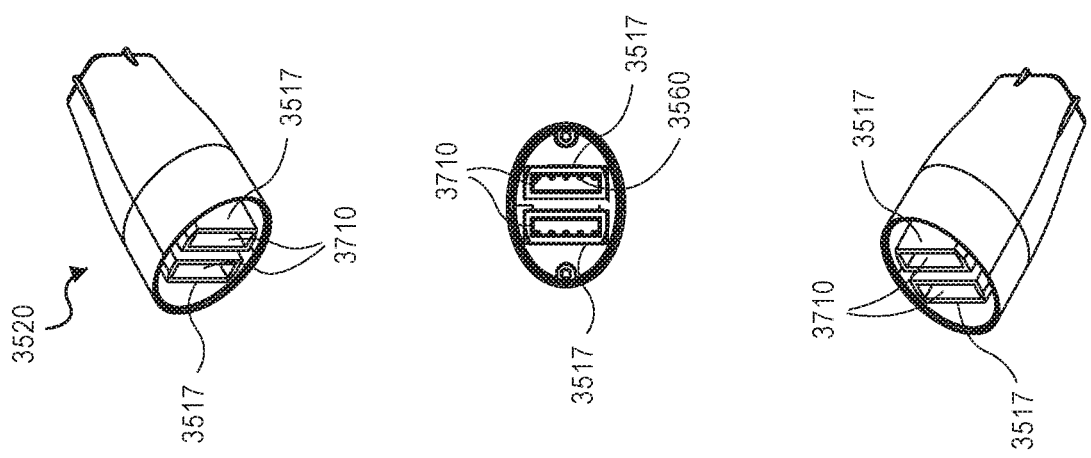
FIG. 37

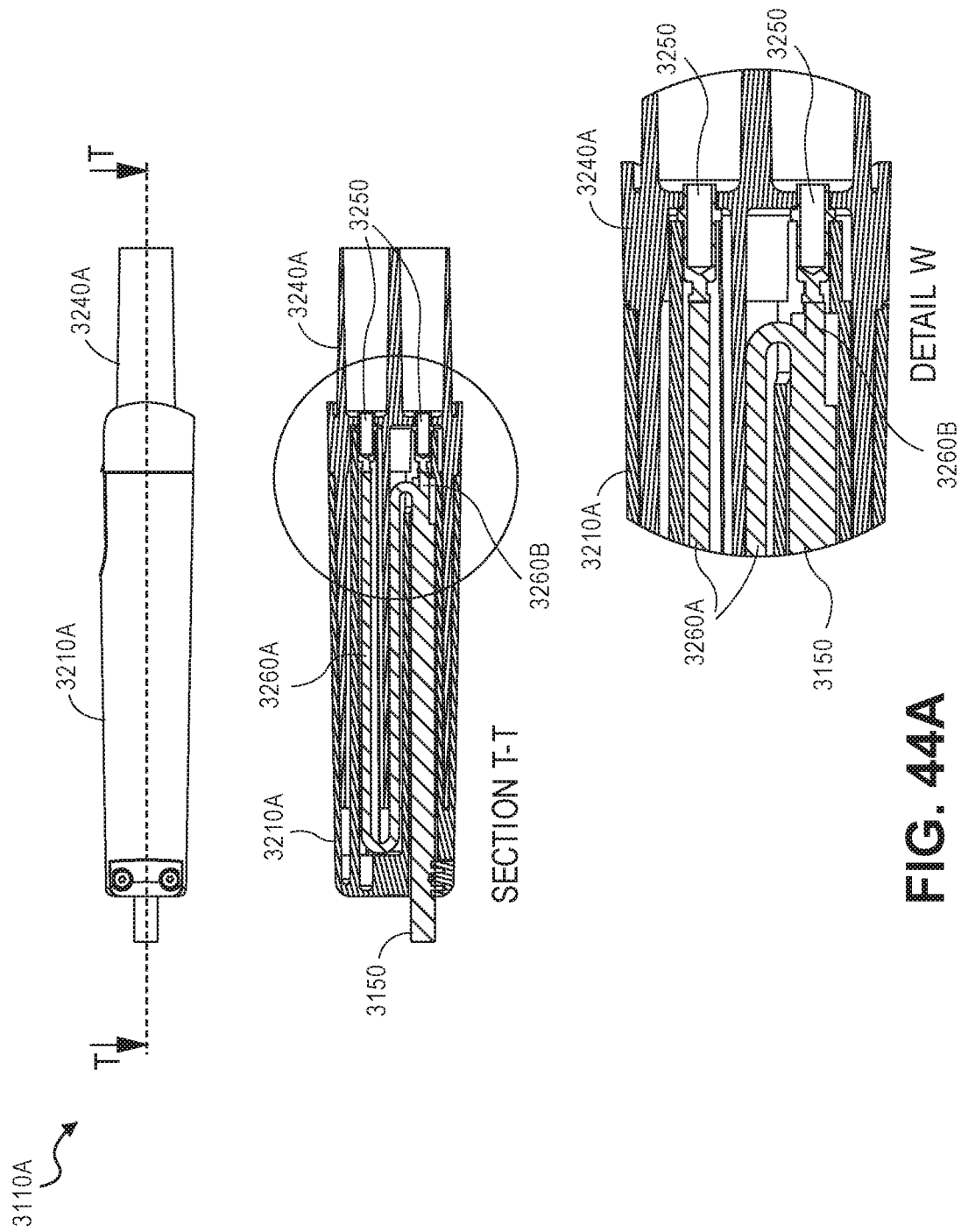

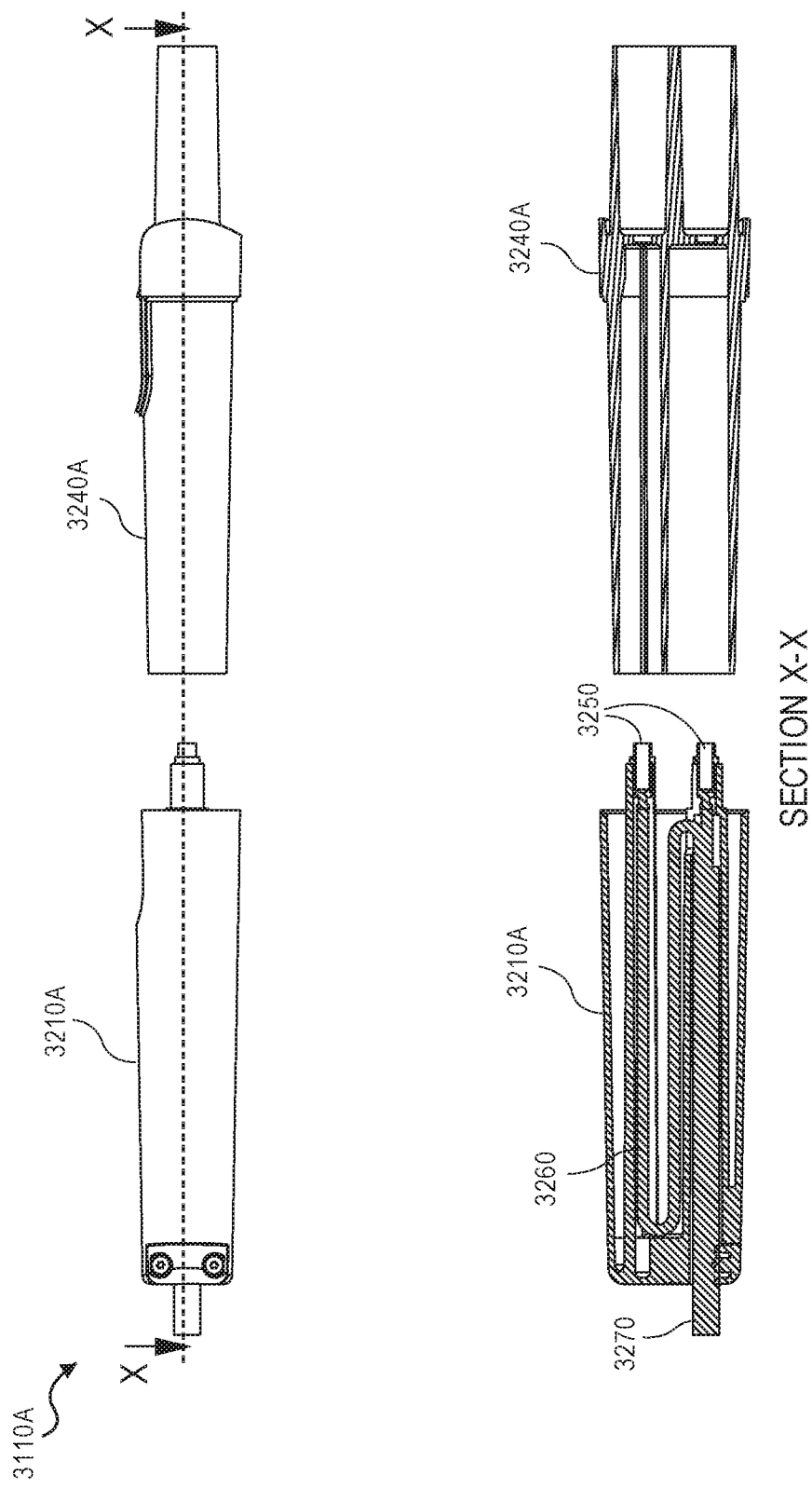

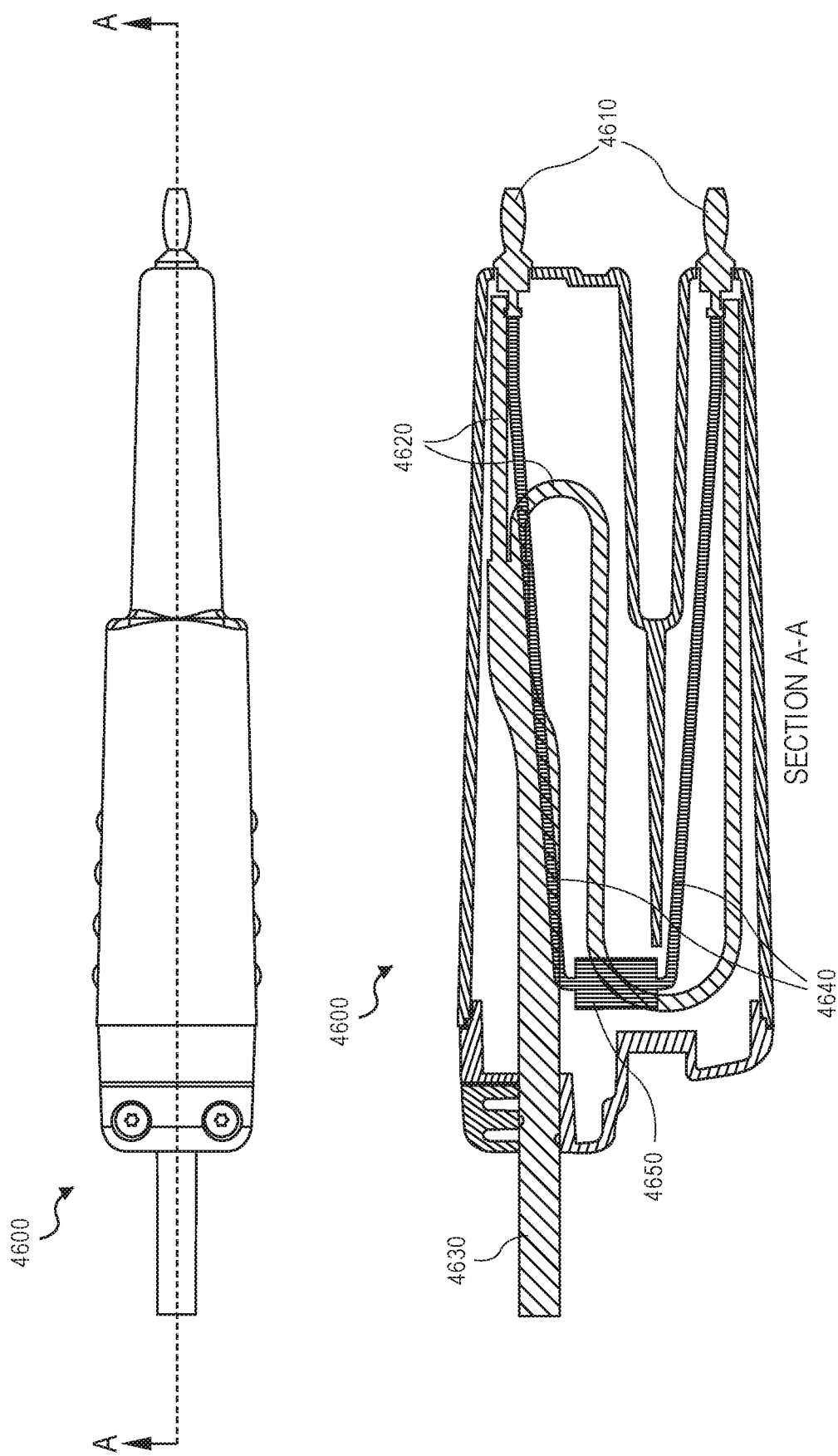

HIGH VOLTAGE CONNECTORS FOR PULSE GENERATORS

BACKGROUND

1. Field of the Invention

The present application generally relates to high voltage connectors and electrodes for applying high voltage electrical pulses to patients. Specifically, the connectors and electrodes deliver high voltage electrical pulses received from a high voltage pulse generator to patients.

2. Description of the Related Art

Surgical excision of a tumor can result in an infection and leave a scar. Furthermore, if there are more tumors, every cancerous tumor should be identified and individually excised by a surgeon. This can be time consuming and expensive, not to mention uncomfortable for patients.

Cancerous tumors that are internal to a patient may be especially difficult to remove, let alone detect and treat. Many patients' lives are turned upside down by the discovery of cancer in their bodies, sometimes which have formed relatively large tumors before being detected.

A "nanosecond pulsed electric field," sometimes abbreviated as nsPEF, includes an electric field with a sub-microsecond pulse width of between 0.1 nanoseconds (ns) and 1000 nanoseconds, or as otherwise known in the art. It is sometimes referred to as sub-microsecond pulsed electric field. NsPEFs often have high peak voltages, such as 10 kilovolts per centimeter (kV/cm), 20 kV/cm, to 500 kV/cm. Treatment of biological cells with nsPEF technology often uses a multitude of periodic pulses at a frequency ranging from 0.1 per second (Hz) to 10,000 Hz.

NsPEFs have been found to trigger apoptosis in cancerous tumors. Selective treatment of such tumors with nsPEFs can induce apoptosis within the tumor cells without substantially affecting normal cells in the surrounding tissue due to its non-thermal nature.

An example of nsPEF applied to biological cells is shown and described in U.S. Pat. No. 6,326,177 (to Schoenbach et al.), which is incorporated herein by reference in its entirety for all purposes.

The use of nsPEF for the treatment of tumors is a relatively new field. There exists a need for electrodes to deliver nsPEF pulses generated by a pulse generator to patients with minimal distortion and with maximum utility and safety.

BRIEF SUMMARY

Some inventive aspects include high voltage electrodes and a high voltage connectors. The electrodes include first and second terminals, configured to contact a patient, and a cable, configured to be connected to a pulse generator via the high voltage connector.

One inventive aspect is an electrode electrically connectable to a pulse generator. The electrode is configured to deliver a pulse generated by the pulse generator to a patient, and includes a plurality of therapeutic terminals configured to deliver the pulse to the patient, first and second electrical pulse inlet holes, and a first pulse input terminal, where the first pulse input terminal is in the first electrical pulse inlet hole and is spaced apart from an entrance to the first electrical pulse inlet hole by a distance greater than about 2.5 cm, and the first pulse input terminal is electrically connected with one or more of the therapeutic terminals. The electrode also includes a second pulse input terminal, where the second pulse input terminal is in the second electrical pulse inlet hole and is spaced apart from an entrance to the second electrical pulse inlet hole by a distance greater than about 2.5 cm, and where the second pulse input terminal is electrically connected with one or more of the therapeutic terminals.

Another inventive aspect is an electrode electrically connectable to a pulse generator. The electrode is configured to deliver a pulse generated by the pulse generator to a patient, and the electrode includes a plurality of therapeutic terminals configured to deliver the pulse to the patient. The electrode also includes a handle including a skirt, and first and second connection terminals within the skirt, and a tip, connected to the handle. The tip includes first and second connectors, configured to mechanically and electrically connect with the connection terminals of the handle while the tip is connected to the handle, and a skirt hole, configured to receive the skirt of the handle while the tip is connected to the handle. The skirt includes first and second holes configured to receive the first and second connectors of the tip while the tip is connected to the handle, and the first and second holes of the skirt are respectively separated from the first and second connection terminals by a distance greater than about 2.5 cm while the tip is connected to the handle.

BRIEF DESCRIPTION OF THE DRAWINGS

FIG. 27A is an illustration of a connector configured to be mated with a housing cutaway portion.

FIG. 27B is an illustration of a connector configured to be mated with a housing cutaway portion.

FIG. 32C illustrates an embodiment of a handle.

FIG. 35B illustrates an embodiment of a tip.

FIG. 37 illustrates an embodiment of a tip cap.

FIG. 44A illustrates an embodiment of a handle.

FIG. 44B illustrates an embodiment of a handle.

FIG. 46 illustrates an embodiment of a connector.

DETAILED DESCRIPTION

It has been shown that nsPEF treatments can be used to cause cancerous tumor cells to undergo apoptosis, a programmed cell death. Tests have shown that tumors can shrink to nonexistence after treatment. No drugs may be necessary. It has also been shown that the subject's immune system may be stimulated to attack all similar tumor cells, including those of tumors that are not within the nsPEF-treated tumor.

A "tumor" includes any neoplasm or abnormal, unwanted growth of tissue on or within a subject, or as otherwise known in the art. A tumor can include a collection of one or more cells exhibiting abnormal growth. There are many types of tumors. A malignant tumor is cancerous, a pre-malignant tumor is precancerous, and a benign tumor is noncancerous. Examples of tumors include a benign prostatic hyperplasia (BPH), uterine fibroid, pancreatic carcinoma, liver carcinoma, kidney carcinoma, colon carcinoma, pre-basal cell carcinoma, and tissue associated with Barrett's esophagus.

A "disease" includes any abnormal condition in or on a subject that is associated with abnormal, uncontrolled growths of tissue, including those that are cancerous, precancerous, and benign, or other diseases as known in the art.

"Apoptosis" of a tumor or cell includes an orderly, programmed cell death, or as otherwise known in the art.

"Immunogenic apoptosis" of a tumor or cell includes a programmed cell death that is followed by an immune system response, or as otherwise known in the art. The immune system response is thought to be engaged when the apoptotic cells express calreticulin or another antigen on their surfaces, which stimulates dendritic cells to engulf, consume, or otherwise commit phagocytosis of the targeted cells leading to the consequent activation of a specific T cell response against the target tumor or cell.

Pulse lengths of between 10 and 900 nanoseconds for nsPEF have been particularly studied to be effective in stimulating an immune response. Pulse lengths of about 100 nanoseconds are of particular interest in that they are long enough to carry sufficient energy to be effective at low pulse numbers but short enough to be effective in the manner desired.

A time of "about" a certain number of nanoseconds includes times within a tolerance of ±1%, 2%, 3%, 4%, 5%, 7.5%, 10%, 15%, 20%, 25% or other percentages, or fixed tolerances, such as ±0.1, ±0.2, ±0.3, ±0.4, ±0.5, ±0.7, ±1.0, ±2.0, ±3.0, ±4.0 ±5.0, ±7.0, ±10, ±15, ±20, ±25, ±30, ±40, ±50, ±75 ns, or other tolerances as acceptable in the art in conformance with the effectivity of the time period.

Immune system biomarkers can be measured before and/or after nsPEF treatment in order to confirm that the immune response has been triggered in a patient. Further, nsPEF treatment can be paired with a CD47-blocking antibody treatment to better train CD8+T cells (i.e., cytotoxic T cells) for attacking the cancer.

Figure 1:
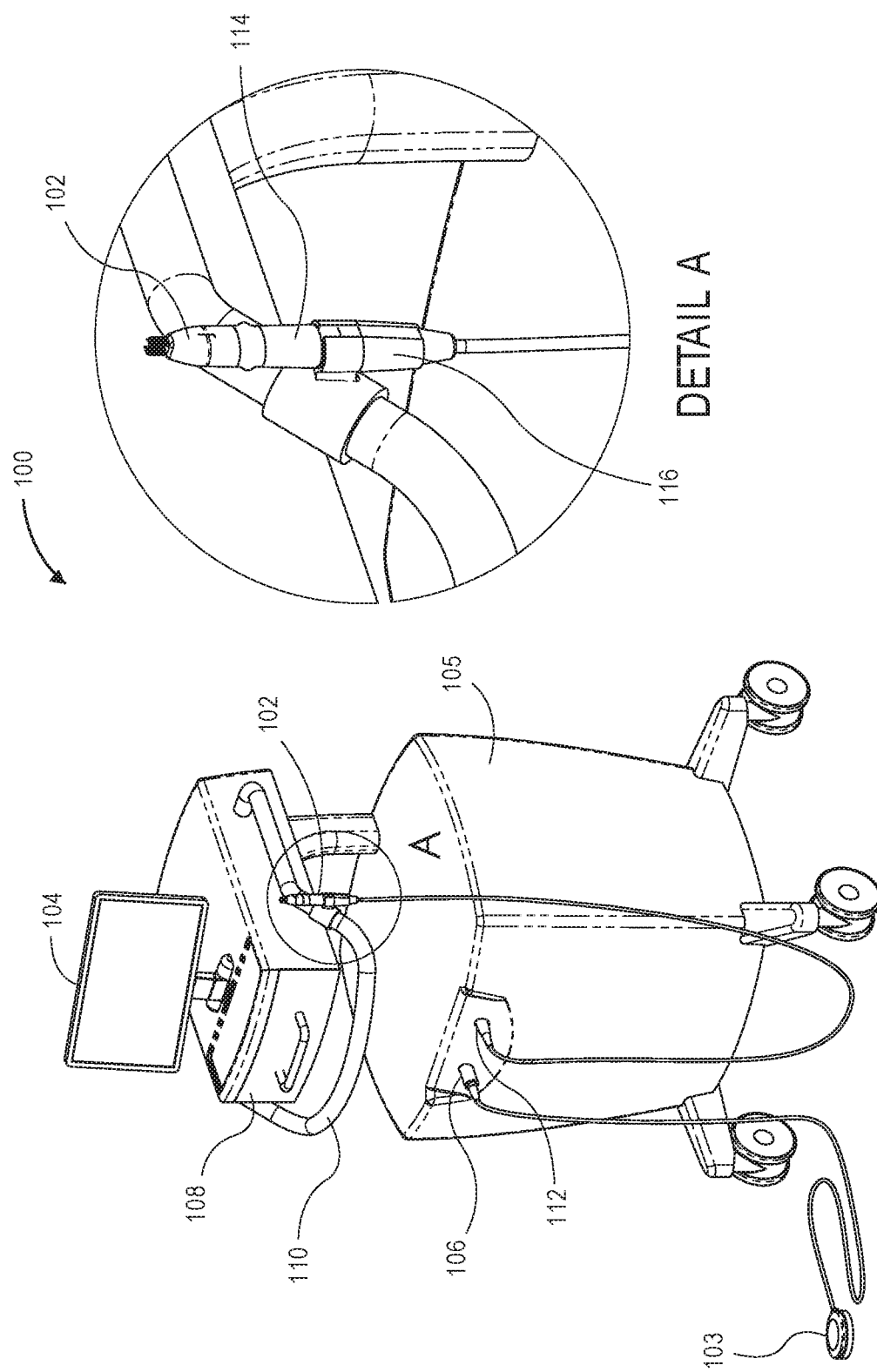
FIG. 1 illustrates a nanosecond pulse generator apparatus in accordance with an embodiment.

FIG. 1 illustrates a nanosecond pulse generator system in accordance with an embodiment. NsPEF system 100 includes electrode 102, footswitch 103, and interface 104. Footswitch 103 is connected to housing 105 and the electronic components therein through connector 106. Electrode 102 is connected to housing 105 and the electronic components therein through high voltage connector 112. NsPEF system 100 also includes a handle 110 and storage drawer 108. As shown in DETAIL A portion of FIG. 1, nsPEF system 100 also includes holster 116, which is configured to hold electrode 102 at its handle portion 114.

A human operator inputs a number of pulses, amplitude, pulse duration, and frequency information, for example, into a numeric keypad or a touch screen of interface 104. In some embodiments, the pulse width can be varied. A microcontroller sends signals to pulse control elements within nsPEF system 100. In some embodiments, fiber optic cables allow control signaling while also electrically isolating the contents of the metal cabinet with nsPEF generation system 100, the high voltage circuit, from the outside. In order to further isolate the system, system 100 may be battery powered instead of from a wall outlet.

Figure 2:
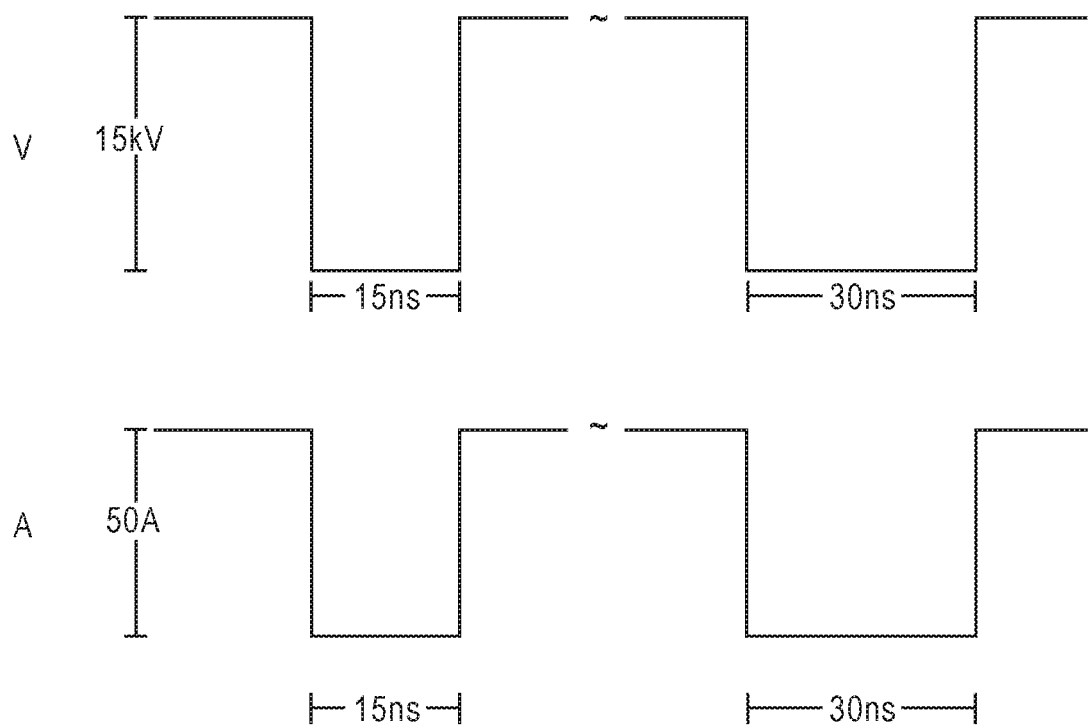
FIG. 2 illustrates a pulse profile for both voltage and current in accordance with an embodiment.

FIG. 2 illustrates a pulse profile for both voltage and current in accordance with an embodiment. Output from the nsPEF system 100 with voltage on the top of the figure and current on the bottom for a first and second pulses. The first pulse has an amplitude of about 15 kV, a current of about 50 A, and a duration of about 15 ns. The second pulse has an amplitude of about 15 kV, a current of about 50 A, and a duration of about 30 ns. Thus, 15 kV may be applied to suction electrodes having 4 mm between the plates so that the tumors experience 47.5 kV/cm, and current between 12 and 50 A. Given a voltage, current depends heavily on the electrode type and tissue resistance.

While FIG. 2 illustrates a specific example, other pulse profiles may also be generated. For example, in some embodiments, rise and/or fall times for pulses may be less than 20 ns, about 20 ns, about 25 ns, about 30 ns, about 40 ns, about 50 ns, about 60 ns, about 75 ns, or greater than 75 ns. In some embodiments, the pulse voltage may be less than 5 kV, about 5 kV, about 10 kV, about 15 kV, about 20 kV, about 25 kV, about 30 kV, or greater than 30 kV. In some embodiments, the current may be less than 10 A, about 10 A, about 25 A, about 40 A, about 50 A, about 60 A, about 75 A, about 100 A, about 125 A, about 150 A, about 175 A, about 200 A, or more than 200 A. In some embodiments, the pulse duration may be less than 10 ns, about 10 ns, about 15 ns, about 20 ns, about 25 ns, about 30 ns, about 40 ns, about 50 ns, about 60 ns, about 75 ns, about 100 ns, about 125 ns, about 150 ns, about 175 ns, about 200 ns, about 300 ns, about 400 ns, about 500 ns, about 750 ns, about 1 µs, about 2 µs, about 3 µs, about 4 µs, about 5 µs, or greater than 5 µs.

Figure 3:
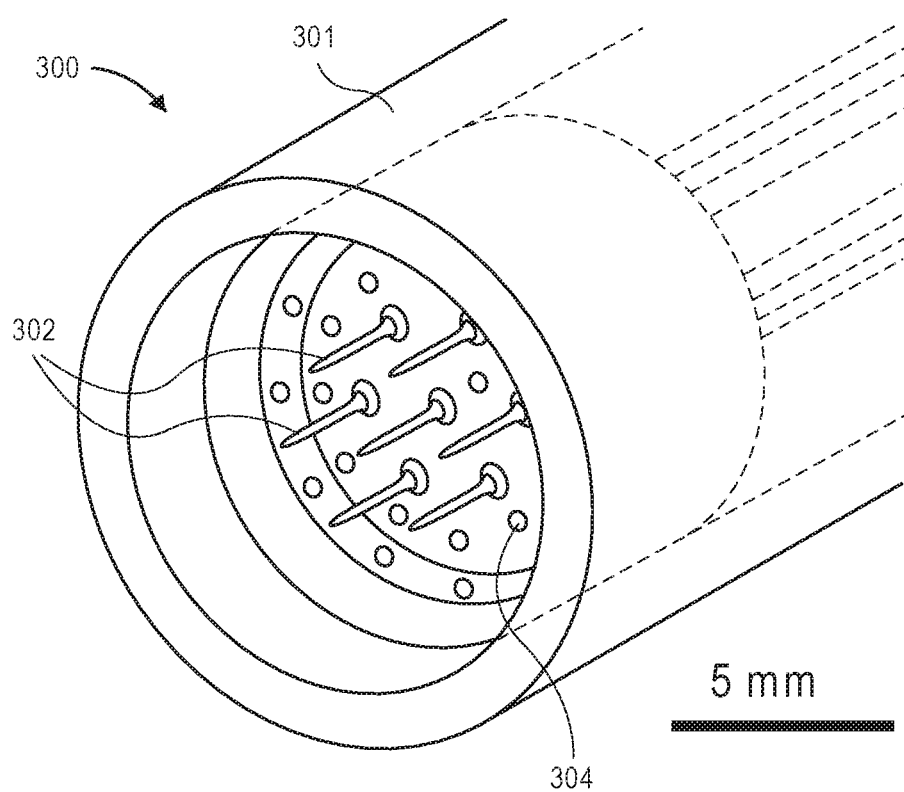
FIG. 3 illustrates a perspective view of a seven-needle electrode in accordance with an embodiment.

FIG. 3 illustrates a perspective view of a seven-needle suction electrode 300 in accordance with an embodiment. In electrode 300, sheath 301 surrounds seven sharp terminals 302 with an broad opening at a distal end. When the open end is placed against a tumor, air is evacuated from the resulting chamber through vacuum holes 304 to draw the entire tumor or a portion thereof into the chamber. The tumor is drawn so that one or more of the terminals 302 preferably penetrates the tumor. Sharp ends of the terminals 302 are configured to pierce the tumor. The center terminal 302 may be at one polarity, and the outer six terminals 302 may be at the opposite polarity. Nanopulses electric fields can then be precisely applied to the tumor using nsPEF system 100 (see FIG. 1).

The terminals 302 can be apposed, one of each positive and negative pair of terminals 302 on one side of a tumor and the other electrode of the pair on an opposing side of the tumor. Opposing sides of a tumor can include areas outside or within a tumor, such as if a needle terminal 302 pierces a portion of the tumor.

Figure 4:
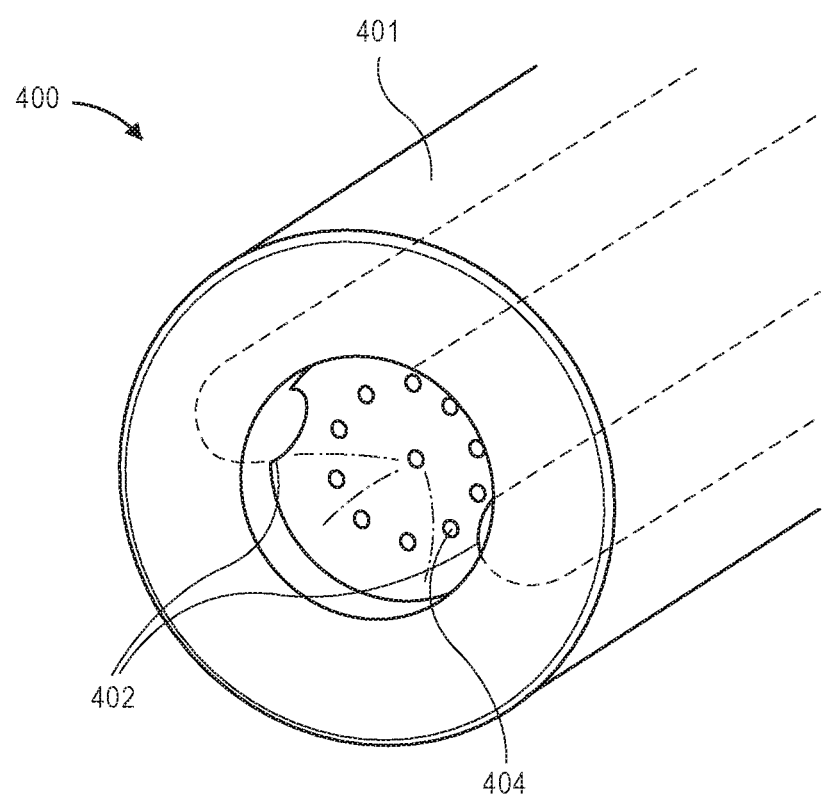
FIG. 4 illustrates a perspective view of a two-pole electrode in accordance with an embodiment.

FIG. 4 illustrates a two-pole suction electrode 400 in accordance with an embodiment. In electrode device 400, sheath 401 surrounds two broad terminals 402 on opposite sides of a chamber. When air is evacuated through vacuum holes 404 and a tumor is pulled within the chamber, the opposing terminals 402 apply nsPEF pulses to the tumor.

The nature of the electrode used mainly depends upon the shape of the tumor. Its physical size and stiffness can also be taken into account in selection of a particular electrode type.

U.S. Pat. No. 8,688,227 B2 (to Nuccitelli et al.) discloses other suction electrode-based medical instruments and systems for therapeutic electrotherapy, and it is hereby incorporated by reference.

If there are multiple tumors in a subject, a surgeon can select a single tumor to treat based on the tumor's compatibility with electrodes. For example, a tumor that is adjacent to a stomach wall may be more easily accessible than one adjacent a spine or the brain. Because a nsPEF pulse is preferably applied so that the electric field transits through as much tumor mass as possible while minimizing the mass of non-tumor cells that are affected, a clear path to two opposed 'poles' of a tumor may also be a selection criterion.

For tumors on or just underneath the skin of subject, needle terminals can be used percutaneously. For locations deeper within a subject, a retractable terminal can fit into a gastroscope, bronchoscope, colonoscope, or other endoscope or laparoscope. For example, a tumor in a patient's colon can be accessed and treated using a terminal within a colonoscope.

Barrett's esophagus, in which portions of tissue lining a patient's esophagus are damaged, may be treated using an electrode placed on an inflatable balloon.

Embodiments of nanosecond pulsed power generators produce electric pulses in the range of single nanoseconds to single microseconds. The pulses are created by rapid release of energy stored in, for example, a capacitive or inductive energy reservoir to a load in a period that is generally much shorter than the charging time of the energy reservoir.

Conventional capacitive-type pulsed generators include pulse forming networks, which provide fixed pulse duration and impedance. With prior knowledge of a load's resistance, a pulse forming network with impedance that matches the load can be used. But for broader applications, especially when the load resistance is unknown, it is desirable to have a pulse generator with a flexibility of impedance matching and variation of pulse duration. Such flexibility can be implemented by switching a capacitor with a controllable switch. In this case, the capacitor can be regarded as a "voltage source" and can adapt to various load resistance. The switched pulse amplitude can then have the same voltage as the voltage of the capacitor. The pulse width is accordingly determined by the switch "on" time.

The selection of switches in nanosecond pulse generators is limited because of the high voltages, high currents, and fast switching times involved.

Spark gap switches, typically used in pulsed power technology, are capable of switching high voltages and conducting high currents. But they can only be turned on, and stopping the current flow in the middle of conduction is impossible. Besides spark gaps, other types of high voltage, high power switches are available, such as: magnetic switches, vacuum switches (Thyratrons for example), and certain high-voltage semiconductor switches.

Magnetic switches, relying on the saturation of magnetic core, change from high impedance to low impedance in the circuit. They can be turned on above a certain current threshold but will not be turned off until all the current is depleted by the load.

Vacuum switches are a good option for high voltage and high repletion rate operation, but similar to magnetic switches, they also can be only turned on, but cannot be turned off at a predetermined time.

Some types of high-voltage semi-conductor switches may also be considered. Thyristors and insulated gate bipolar transistors (IGBTs) may, in some embodiments be used. However, the turn-on times of Thyristors and IGBTs limit their usefulness.

Metal-oxide-semiconductor field-effect transistors (MOSFETs) have insufficient maximum drain to source voltage ratings (e.g. <1 kV) and insufficient maximum drain to source current ratings (e.g. <50 A) to be used in conventional pulse generator architectures to produce the voltage and current necessary for the applications discussed herein. If they were used, a large number of stages would be needed in order to produce high-amplitude output voltages. However, in conventional Marx generator architectures with a large number of stages, the Marx generator goes into an underdamped mode instead of a critically damped mode, resulting in loss in overshoot. As a result, the overall voltage efficiency decreases. For example, a voltage efficiency of a Marx generator may be 80% at 5 stages but decrease to 50% at 20 stages.

Furthermore, as the number of stages is increased, the impedance of the Marx generator also increases. This reduces the total energy deliverable to the load. This is particularly unfavorable for driving low impedance loads and long pulses.

In addition, the charging losses in the charging resistors also increases with the increased number of stages. As a result, such Marx generators are unsuitable for high repetition rate operation.

Therefore, in order to produce high voltage pulses, simply increasing the number of stages will cause a series of problems, including low efficiency, high impedance, etc. Because there is a tradeoff between the number of the stages and the actual output voltage, using conventional Marx generators cannot produce high voltage pulses which are sufficient for the applications discussed herein.

Some embodiments of this disclosure include a tunable, high voltage, nanosecond pulse generator. The switches may be power MOSFETs, which may, for example, be rated for a voltage of 1 kV and current of up to 30 A. Voltage is scaled up by a Marx-switch stack hybrid circuit. In each Marx generator stage, a particularly configured stack of MOSFETs is used. As a result, the charging voltage for each stage is greater than the rated maximum for a single switch.

A technical advantage of the configuration is that the overall output voltage can be increased with just a few stages (e.g. <=5). As a result, the problems discussed above with Marx generators having a large number of stages are avoided and high efficiency, low impedance, and large variability in the pulse duration can be achieved.

Such an architecture also allows much easier control as only one trigger circuit may be needed for each stage. One additional benefit is that the pulse generator has low impedance, so it will be able to drive various loads with high current and extended pulse duration. The scaling up of the current is implemented by combining multiple Marx-switch stack circuits in parallel. The pulse duration is controlled by the closing and opening of the switch stack switches.

Figure 5:
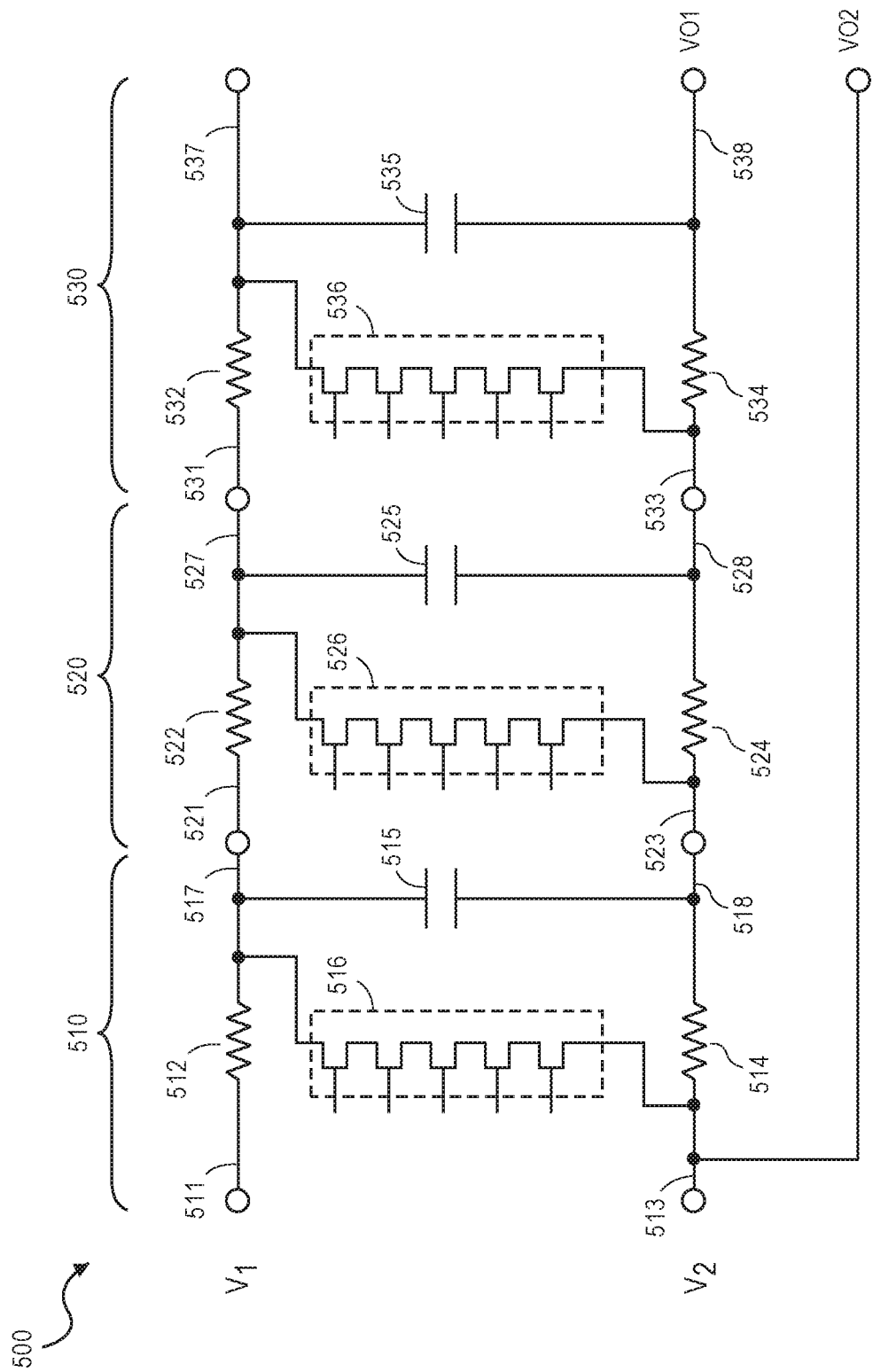
FIG. 5 is an electrical schematic of a pulse generator in accordance with an embodiment.

FIG. 5 illustrates a pulse generator circuit 500 which may be used inside nsPEF system 100 of FIG. 1. Pulse generator circuit 500 illustrates a panel comprising a Marx generator switched by three switch stacks. The nsPEF system can have a single pulse generator circuit panel. In some embodiments, a nsPEF system includes multiple panels in parallel.

Circuit 500 includes three stages—510, 520, and 530. In some embodiments, another number of stages is used. For example, in some embodiments, 2, 4, 5, 6, 7, 8, 9, or 10 stages are used. Stage 510 includes resistors 512 and 514, capacitor 515, and switch stack 516. Likewise, stage 520 includes resistors 522 and 524, capacitor 525, and switch stack 526, and stage 530 includes resistors 532 and 534, capacitor 535, and switch stack 536. Each of these elements have structure and functionality which is similar to the corresponding elements of stage 510.

Stage 510 has first and second input voltage input terminals 511 and 513 and first and second voltage output terminals 517 and 518. Stage 520 has first and second input voltage input terminals 521 and 523, and first and second voltage output terminals 527 and 528. Stage 530 has first and second input voltage input terminals 531 and 533, and first and second voltage output terminals 537 and 538.

The first and second voltage input terminals 511 and 513 of stage 510 are respectively connected to first and second power supply input terminals V1 and V2. The first and second voltage output terminals 517 and 518 of stage 510 are respectively connected to the first and second voltage input terminals 521 and 523 of stage 520. The first and second voltage output terminals 527 and 528 of stage 520 are respectively connected to the first and second voltage input terminals 531 and 533 of stage 530. The second voltage output terminal 538 of stage 530 and second voltage input terminal 513 of stage 510 are respectively connected to first and second power output terminals VO1 and VO2.

Pulse generator circuit 500 operates in a charge mode, and in a discharge mode. During the charge mode, described below with reference to FIG. 6A in more detail, capacitors 515, 525, and 535 are charged by current received from the first and second power supply input terminals V1 and V2. During the discharge mode, described below with reference to FIG. 6B in more detail, capacitors 515, 525, and 535 are discharged to provide a current to a load (not shown) connected across first and second power output terminals VO1 and VO2.

Figure 6A:
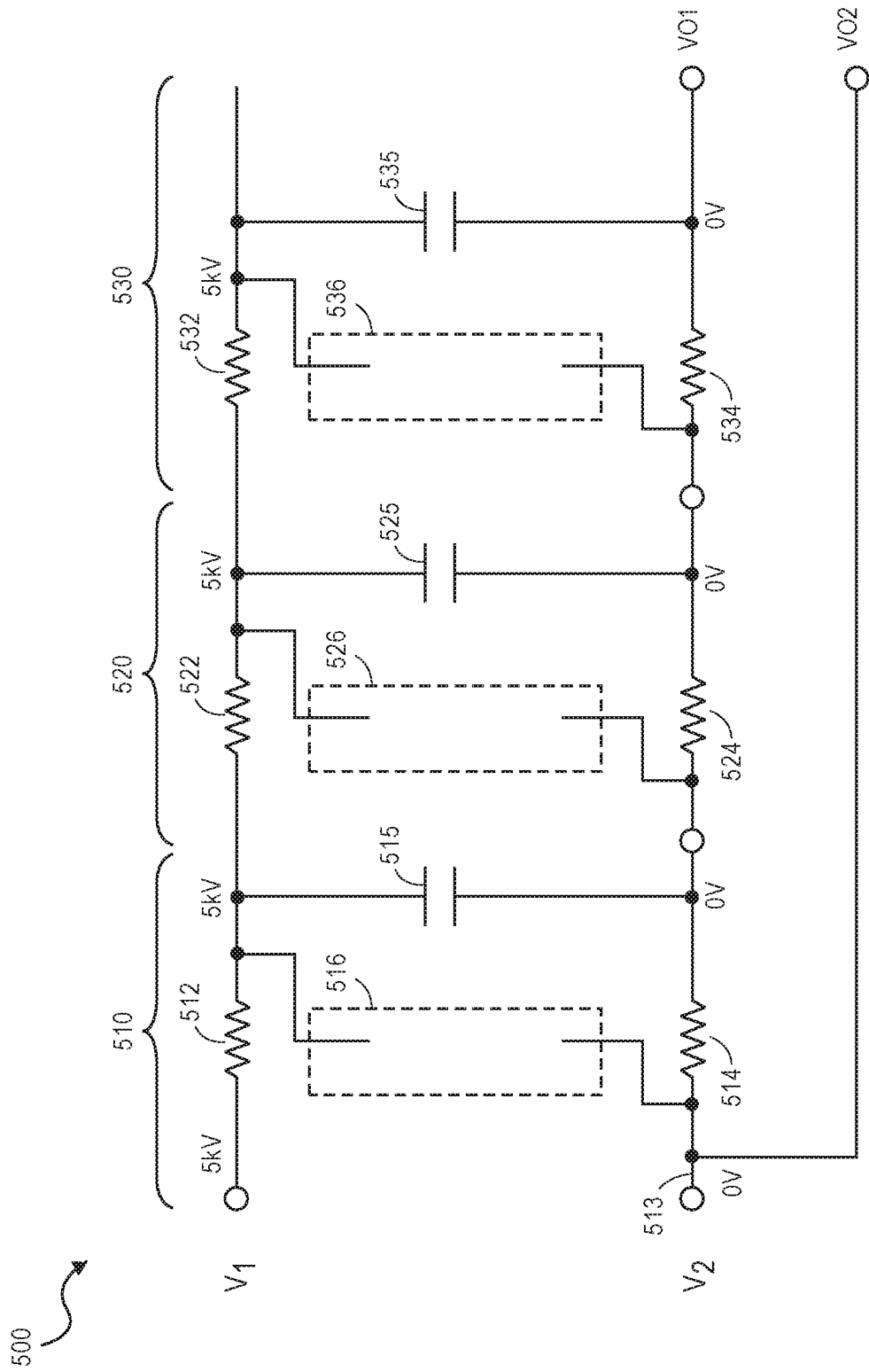
FIG. 6A is a schematic illustrating the pulse generator shown in FIG. 5 during charge mode.

FIG. 6A illustrates pulse generator circuit 500 during charge mode. First and second input voltages are respectively applied to first and second power supply input terminals V1 and V2 while each of switch stacks 516, 526, and 536 are nonconductive or open, and while first and second power output terminals may be disconnected from the load (not shown). Because each of switch stacks 516, 526, and 536 are open, substantially no current flows therethrough, and they are represented as open circuits in FIG. 6A. During the charge mode, each of capacitors 515, 525, and 535 are charged by current flowing through resistors 512, 522, 532, 534, 524, and 514 to or toward a voltage equal to the difference between the first and second input voltages.

Each of the switches of switch stacks 516, 526, and 536 has a breakdown voltage rating which should not be exceeded. However, because the switches are serially connected, the capacitors 515, 525, and 535 may be charged to a voltage significantly greater than the breakdown voltage of the individual switches. For example, the breakdown voltage of the switches may be 1 kV, and the capacitors 515, 525, and 535 may be charged to a voltage of 5 kV, when 5 or more switches are used in each switch stack.

For example, the first and second input voltages may respectively be 5 kV and 0V. In such an example, each of the capacitors 515, 525, and 535 is charged to or toward a voltage equal to 5 kV. In some embodiments, the difference between the first and second input voltages is limited to be less than 10 kV.

Figure 6B:
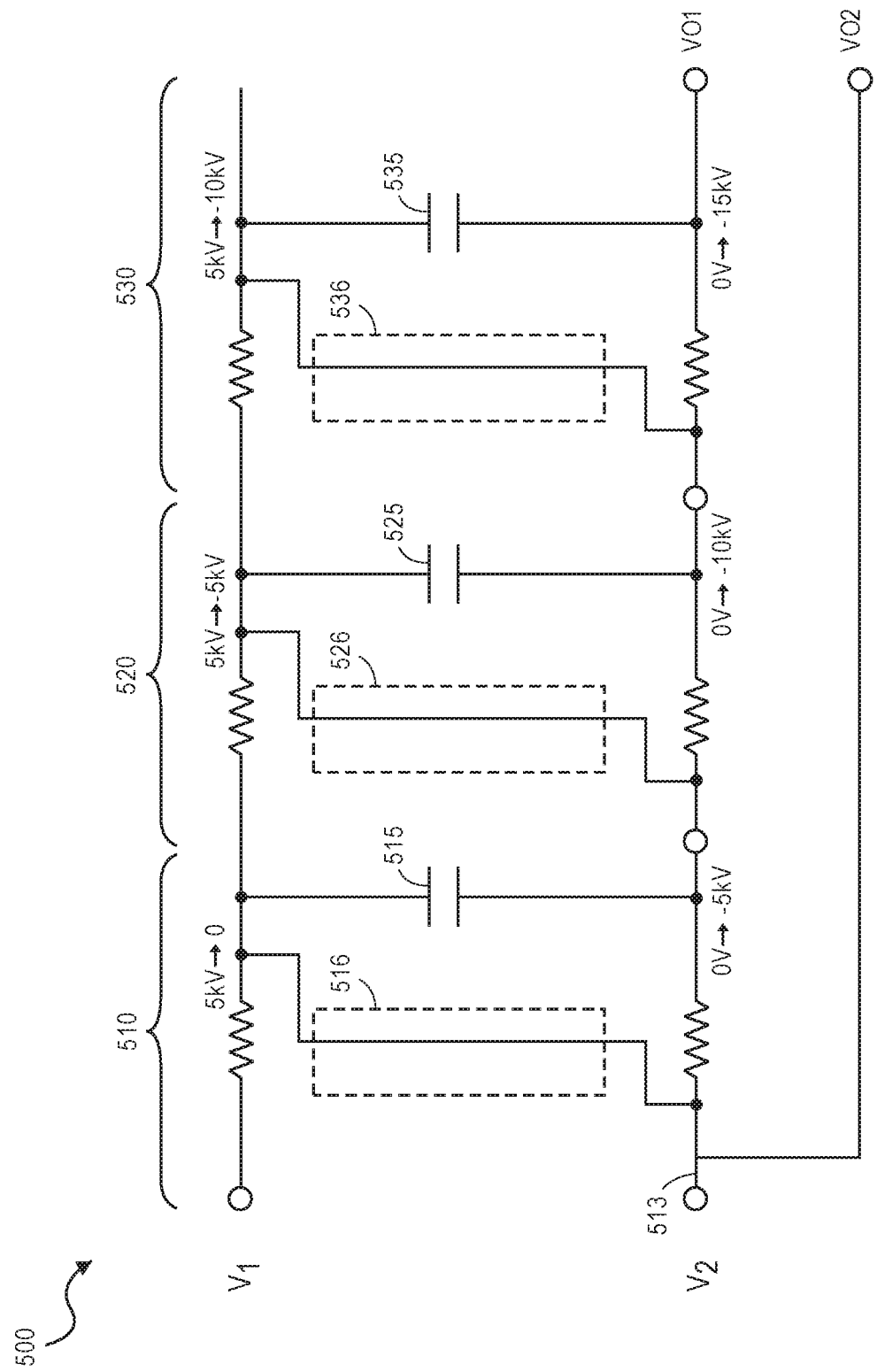
FIG. 6B is a schematic illustrating the pulse generator shown in FIG. 5 during discharge mode.

FIG. 6B illustrates pulse generator circuit 500 during discharge mode. First power supply input terminal V1 may be disconnected from the first input voltage. In some embodiments, first power supply input terminal V1 remains connected to the first input voltage. Second power supply input terminal V2 remains connected to the second input voltage. In addition, each of switch stacks 516, 526, and 536 are conductive or closed. Because each of switch stacks 516, 526, and 536 are closed, current flows therethrough, and they are represented as conductive wires in FIG. 6B. As a result, a low impedance electrical path from power supply input terminal V2 to power output terminal VO1 is formed by switch stack 516, capacitor 515, switch stack 526, capacitor 525, switch stack 536, and capacitor 535. Consequently, the difference between the voltages at the power output terminals VO1 and VO2 is equal to the number of stages (in this example, 3) times the difference between the first and second input voltages.

Where the first and second input voltages are respectively 5 kV and 0V, a voltage difference of 15 kV is developed across the power output terminals VO1 and VO2.

Figure 7:
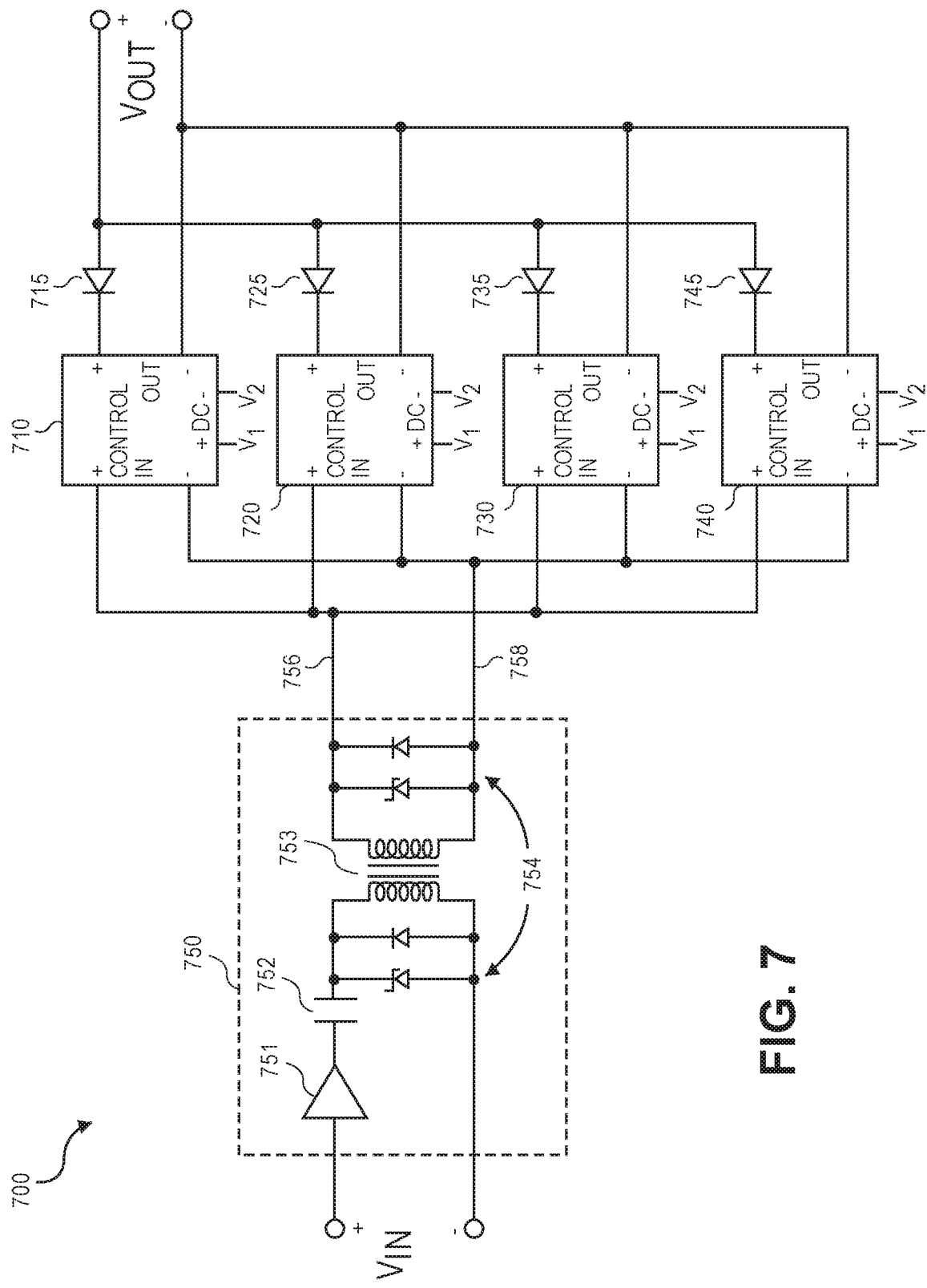
FIG. 7 is an electrical schematic of an assembly of pulse generator circuits.

FIG. 7 illustrates an alternative pulse generator circuit 700 which may be used inside nsPEF system 100 of FIG. 1. This pulse generator includes panels in parallel. The number of panels can be adjusted to allow the system to generate different amounts of current and power.

Pulse generator circuit 700 receives input pulses across input port Vin, and generates output pulses across output port Vout in response to the received input pulses.

Pulse generator circuit 700 includes multiple panels or pulse generator circuits 710, 720, 730, and 740. Pulse generator circuit 700 also includes driver 750. In this embodiment, four pulse generator circuits are used. An alternative embodiments, fewer or more pulse generator circuits are used. For example, in some embodiments, 2, 3, 5, 6, 7, 8, 9, 10 or another number of pulse generator circuits are used.

Each of the pulse generator circuits 710, 720, 730, and 740 may have characteristics similar to other pulse generator circuits discussed herein. For example, each the pulse generator circuits 710, 720, 730, and 740 may have characteristics similar to pulse generator circuit 500 discussed above with reference to FIGS. 5, 6A, and 6B.

Each of pulse generator circuits 710, 720, 730, and 740 has positive and negative DC input terminals, positive and negative control input terminals, and positive and negative output terminals, and is configured to generate output voltage pulses across the positive and negative output terminals in response to driving signal pulses applied across the positive and negative control input terminals. The output voltage pulses are also based on power voltages received across positive and negative DC power input terminals.

The driving signal pulses are generated across conductors 756 and 758 by driver 750, which includes amplifier circuit 751, capacitor 752, and transformer 753. In some embodiments, driver 750 also includes clamp circuits 754.

Driver 750 receives an input signal pulse at input port Vin and generates a driving signal pulse across conductors 756 and 758 in response to the input signal pulse. Amplifier circuit 751 receives the input signal pulse and drives transformer 753 through capacitor 752, which blocks low frequency and DC signals. In response to being driven by amplifier circuit 751, transformer 753 generates an output voltage pulse across conductors 756 and 758, such that the duration of the output voltage pulse is equal to or substantially equal (e.g. within 10% or 1%) to the duration of the input signal pulse at input port Vin.

In some embodiments, clamp circuits 754 are included at least to dampen potential signals, which may otherwise be caused by resonance. Clamp circuits 754 include parallel diodes, which provide a short-circuit path for any current reversal, and also clamp the maximum voltage across the components connected to the clamp circuits 754.

In some embodiments, transformer 753 has a 1:1 turns ratio. In alternative embodiments, a different turns ratio is used.

Each of pulse generator circuits 710, 720, 730, and 740 receives the voltage pulses from driver 750 across the positive and negative control input terminals and generates corresponding voltage pulses across the positive and negative output terminals in response to the received voltage pulses from driver 750. The voltage pulses generated across the positive and negative output terminals have durations which are equal to or substantially equal (e.g. within 10% or 1%) to the durations of the voltage pulses received from driver 750.

In this embodiment, the negative output terminals of pulse generator circuits 710, 720, 730, and 740 are directly connected to the negative Vout terminal of the output port Vout of pulse generator circuit 700. In addition, in this embodiment, the positive output terminals of pulse generator circuits 710, 720, 730, and 740 are respectively connected to the positive Vout terminal of the output port Vout of pulse generator circuit 700 through diodes 715, 725, 735, and 745. Diodes 715, 725, 735, and 745 decouple pulse generator circuits 710, 720, 730, and 740 from one another. As a consequence, interference and the associated pulse distortion that would otherwise occur is substantially eliminated. For example, diodes 715, 725, 735, and 745 prevent current from one of pulse generator circuits 710, 720, 730, and 740 to another of pulse generator circuits 710, 720, 730, and 740 if the switching is not perfectly synchronous. Diodes 715, 725, 735, and 745 also prevent current from flowing from the pulse generator circuits 710, 720, 730, and 740 while they are charging.

In this embodiment, diodes 715, 725, 735, and 745 each include a single diode. In alternative embodiments, diodes 715, 725, 735, and 745 each include multiple diodes connected serially based at least upon voltage ratings of the serially connected diodes. Additionally or alternatively, in some embodiments, diodes 715, 725, 735, and 745 each include multiple diodes connected in parallel based at least upon the current ratings of the parallel connected diodes.

In this embodiment, diodes 715, 725, 735, and 745 are connected so as to conduct current from the positive terminal of output port Vout toward pulse generator circuits 710, 720, 730, and 740, as pulse generator circuits 710, 720, 730, and 740 in this embodiment are configured to generate negative pulses. In alternative embodiments, where pulse generator circuits are configured to generate positive pulses, diodes may be similarly connected so as to conduct current from the pulse generator circuits to the positive terminal of the output port.

Figure 8:
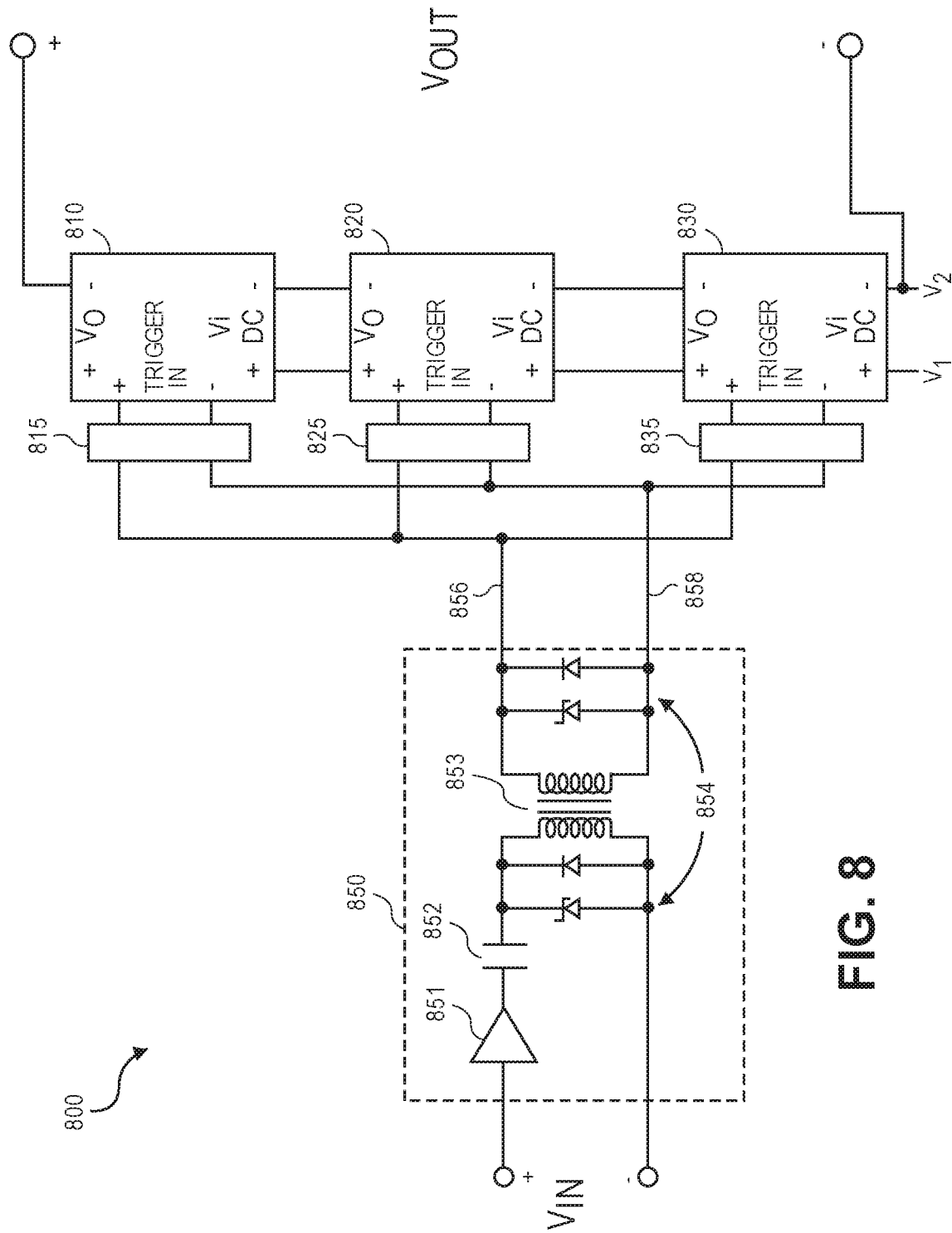
FIG. 8 is an electrical schematic of one of the pulse generator circuits shown in FIG. 7.

FIG. 8 illustrates a pulse generator circuit 800 which may be used for pulse generator circuits 710, 720, 730, and 740 of pulse generator circuit 1000 of FIG. 7.

Pulse generator circuit 800 receives input pulses across input port Vin, and generates output pulses across output port Vout in response to the received input pulses.

Pulse generator circuit 800 includes multiple pulse generator stages 810, 820, and 830. In this embodiment, pulse generator circuit 700 also includes driver 850, and optional common mode chokes 815, 825, and 835.

Each of the pulse generator stages 810, 820, and 830 may have characteristics similar to other pulse generator stages discussed herein. For example, each the pulse generator stages 810, 820, and 830 may have characteristics similar to stages 510, 520, and 530 of pulse generator circuit 500 discussed above with reference to FIGS. 5, 6A, and 6B. In some embodiments, fewer or more pulse generator stages may be used.

Each of pulse generator stages 810, 820, and 830 has positive and negative trigger input terminals, power positive and negative DC input terminals, and positive and negative Vo output terminals, and is configured to generate output voltage pulses across the positive and negative Vo output terminals in response to driving signal pulses applied across the positive and negative trigger input terminals. The output voltage pulses are also based on power voltages V1 and V2 respectively received at power positive and negative DC input terminals.

In this embodiment, the negative Vi input terminal of pulse generator stage 830 is connected with the negative terminal of the output port Vout of pulse generator circuit 800. In addition, in this embodiment, the negative Vo output terminal of pulse generator stage 810 is connected with the positive terminal of the output port Vout of pulse generator circuit 800.

In addition, as shown, the positive Vo output terminal of pulse generator 830 is connected with the positive Vi input terminal of pulse generator 820, and the negative Vo output terminal of pulse generator 830 is connected with the negative Vi input terminal of pulse generator 820. Furthermore, the positive Vo output terminal of pulse generator 820 is connected with the positive Vi input terminal of pulse generator 810, and the negative Vo output terminal of pulse generator 820 is connected with the negative Vi input terminal of pulse generator 810.

The driving signal pulses for pulse generator stages 810, 820, and 830 are generated across conductors 856 and 858 by driver 850, which includes amplifier circuit 851, capacitor 852, and transformer 853. In some embodiments, driver 850 also includes clamp circuits 854.

Driver 850 receives an input signal pulse at input port Vin, which is connected to conductors 756 and 758, as shown in FIG. 7 discussed above. Driver 850 generates a driving signal pulse across conductors 856 and 858 in response to the input signal pulse. Amplifier circuit 851 receives the input signal pulse, and drives transformer 853 through capacitor 852, which reduces or blocks low frequency and DC signals. In response to being driven by amplifier circuit 851, transformer 853 generates an output voltage pulse across conductors 756 and 758, such that the duration of the output voltage pulse is equal to or substantially equal (e.g. within 10% or 1%) to the duration of the input signal pulse at input port Vin.

In some embodiments, clamp circuits 854 are included at least to dampen potential signals, which may otherwise be caused by resonance. Clamp circuits 854 include parallel diodes, which provide a short-circuit path for any current reversal, and also clamp the maximum voltage across the components connected to the clamp circuits 854.

In some embodiments, transformer 853 has a 1:1 turns ratio. In alternative embodiments, a different turns ratio is used.

Each of pulse generator stages 810, 820, and 830 receives the voltage pulses from driver 850 through a corresponding choke 815, 825, or 835, which blocks high frequency signals, for example, from coupling from the high voltage pulse generator stages 810, 820, and 830. The voltage pulses are received at the positive and negative trigger input terminals and the pulse generator stages 810, 820, and 830 each generate corresponding voltage pulses across the positive and negative Vo output terminals in response to the received voltage pulses from driver 850. The voltage pulses generated across the positive and negative Vo output terminals have durations which are equal to or substantially equal (e.g. within 10% or 1%) to the durations of the voltage pulses received from driver 850.

Figure 9:
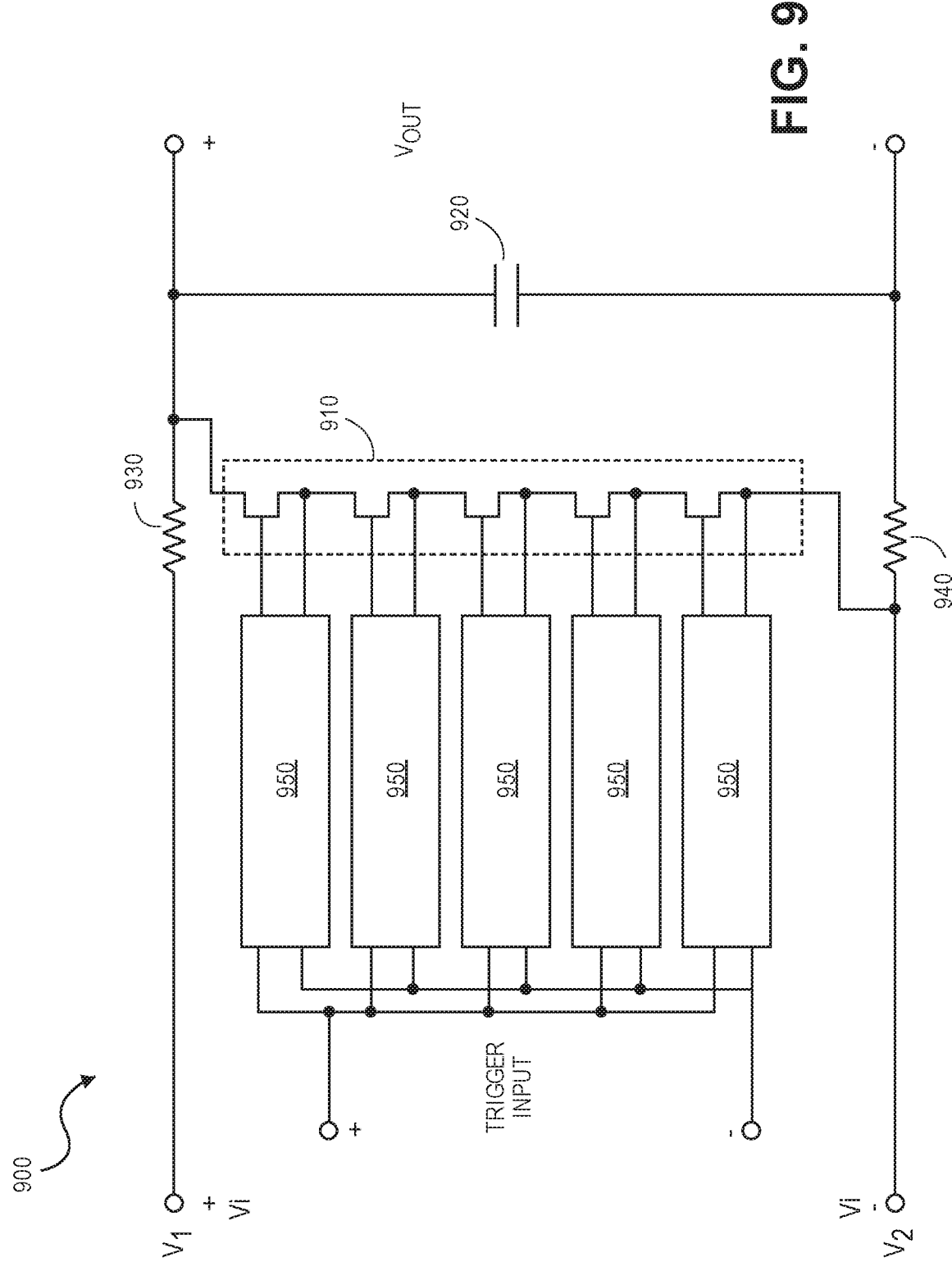
FIG. 9 is an electrical schematic of one of the pulse generator stages shown in FIG. 8.

FIG. 9 illustrates a pulse generator stage 900 which may be used as one of the pulse generator stages 810, 820, and 830 of pulse generator circuit 800 shown in FIG. 8.

Pulse generator stage 900 receives trigger pulses across input port trigger input, and generates output voltages at output port Vout in response to the received trigger pulses. The output voltages are also generated based on power voltages received at power input terminals V1 and V2. Pulse generator stage 900 includes multiple switch drivers 950. Pulse generator stage 900 also includes switch stack 910, capacitor 920, and resistors 930 and 940.

Switch drivers 950 are configured to receive the trigger pulses, and to generate control signals for the switches of switch stack 910 in response to the received trigger pulses, as discussed in further detail below. Each of the control signals is referenced to a voltage specific to the switch being driven. Accordingly, a first switch receives a control signal pulse between first and second voltages, and a second switch receives a control signal pulse between third and fourth voltages, where each of the first, second, third, and fourth voltages are different. In some embodiments, the difference between the first and second voltages is substantially the same as the difference between the third and fourth voltages.

Switch stack 910, capacitor 920, and resistors 930 and 940 cooperatively function with corresponding elements in the other pulse generator stages of pulse generator circuit 800, discussed above with reference to FIG. 8, to generate the voltage pulses across the positive and negative Vo output terminals of pulse generator circuit 800. These elements may, for example, cooperatively function as the corresponding elements discussed above with reference to pulse generator circuit 500 shown in FIGS. 5, 6A, and 6B. For example, these elements may cooperate to generate the voltage pulses across the positive and negative Vo output terminals of pulse generator circuit 800 in response to the power voltages applied to power input terminals V1 and V2 and to the control signals applied to the switches of switch stack 910.

Because the control signals are generated in response to the input pulses received across input port Vin of pulse generator circuit 700 illustrated in FIG. 7 through multiple stages of driving, the control signals cause all of the switches of the switch stacks of pulse generator circuit 700 to be turned on and to be turned off substantially simultaneously. For example, a 15V input pulse having a duration of, for example 100 ns, received at input port Vin of pulse generator circuit 700 may cause the pulse generator circuit 700 to generate a high-voltage (e.g. ~15 kV) output pulse having a duration of about 100 ns. Similarly, a 15V input pulse having a duration of, for example 5 μs, received at input port Vin of pulse generator circuit 700 may cause the pulse generator circuit 700 to generate a high-voltage (e.g. ~15 kV) output pulse having a duration of about 5 μs. Accordingly, the duration of the high-voltage output pulse is substantially the same as a selected duration of an input pulse.

Figure 10:
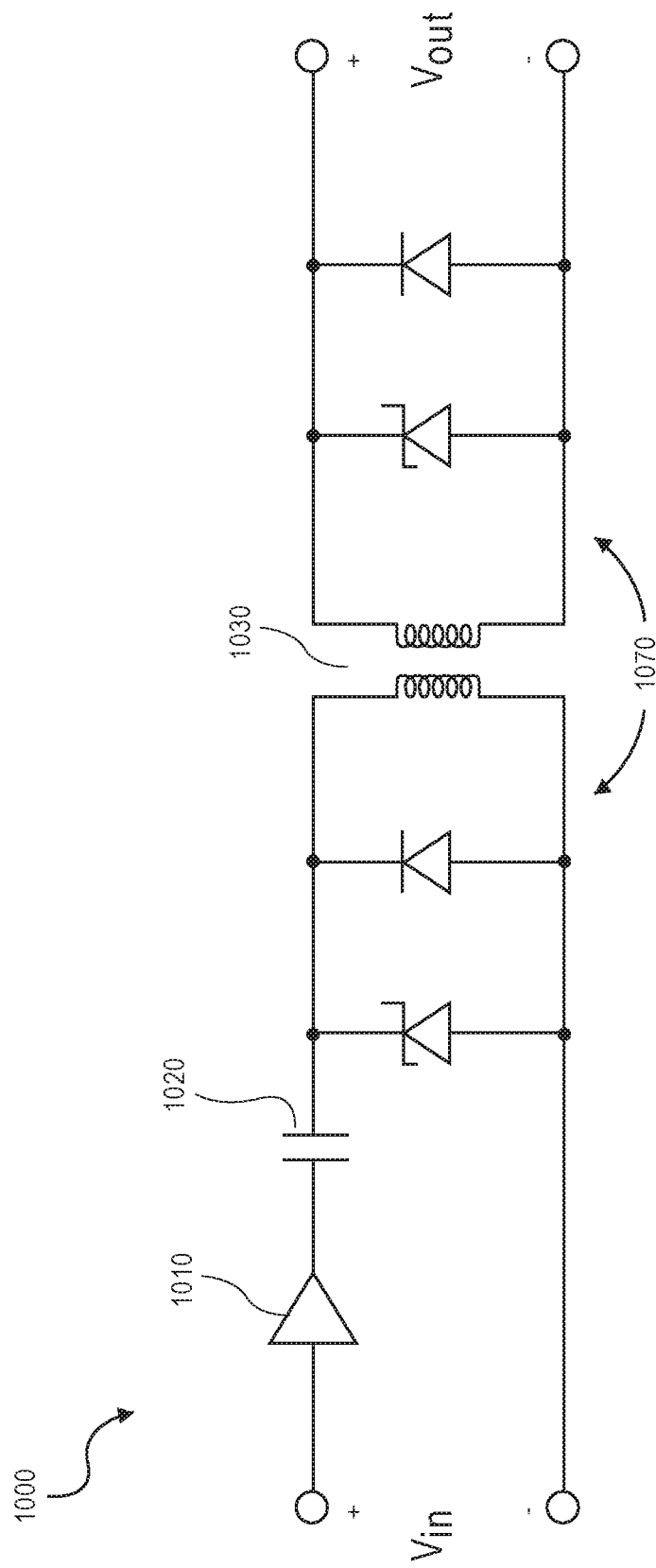
FIG. 10 is an electrical schematic of one of the switch drivers shown in FIG. 9.

FIG. 10 illustrates a switch driver 1000 which may be used as one of the switch drivers shown in FIG. 9.

Switch driver 1000 receives trigger pulses across input port Vin, and generates control signal pulses at output port Vout in response to the received trigger pulses. Switch driver 1000 includes amplifier circuit 1010, capacitor 1020, and transformer 1030. In some embodiments, switch driver 1000 also includes clamps circuits 1070.

Amplifier circuit 1010 receives the trigger pulses, and drives transformer 1030 through capacitor 1020, which reduces or blocks low frequency and DC signals. In response to being driven by amplifier circuit 1010, transformer 1030 generates control signal pulses across resistor 1070 at output port Vout, such that the duration of the control signal pulses is equal to or substantially equal (e.g. within 10% or 1%) to the duration of the trigger pulses at input port Vin.

In some embodiments, amplifier circuit 1010 includes multiple amplifier integrated circuits. For example, for increased current driving capability, multiple amplifier integrated circuits may be connected in parallel to form amplifier circuit 1010. For example, 2, 3, 4, 5, 6, 7, 8 or another number of amplifier integrated circuits may be used.

In some embodiments, clamp circuits 1070 are included at least to dampen potential signals, which may otherwise be caused by resonance. Clamp circuits 1070 include parallel diodes, which provide a short-circuit path for any current reversal, and also clamp the maximum voltage across the components connected to the clamp circuits 1070.

In some embodiments, the drivers 750, 850, and 1000 receive power from a DC-DC power module which is isolated from the power supply for the Marx generator. This ensures the cutoff of ground coupling.

In some embodiments, transformer 1030 has a 1:1 turns ratio. In alternative embodiments, a different turns ratio is used.

In some embodiments, in order to obtain very fast switching, the transformers 1030 has fewer than 5 turns in the primary winding and fewer than 5 turns in the secondary winding. For example, in some embodiments, the transformer 1030 has 1, 2, 3, or 4 turns in each of the primary and secondary windings. In some embodiments, the transformer 1030 has less than a complete turn, for example, ½ turn in the primary and secondary windings. The low number of turns in each of the primary and secondary windings allows for a low inductance loop and increases the current risetime in the secondary winding, which charges the input capacitance of the MOSFET switches.

Transformers for triggering MOSFETs in conventional applications require high coupling, high permeability, and a low-loss core in order to ensure current transfer efficiency. From pulse to pulse, the residual flux in the core needs to be cleared in order to avoid saturation when the transformer is operated at high frequency. Conventionally, a resetting circuit, which involves a third winding, to dissipate the core energy is used.

In some embodiments, lossy transformers, such as that typically used as an electromagnetic interference (EMI) choke to confine high frequency signals and dissipate their energy as heat are used to trigger the switches. For example, the transformers may have a voltage time constant less than 100Vμs. In some embodiments, the Transformers have a voltage time constant less than 50Vμs, 30Vμs, 20Vμs, 10Vμs, or 5Vμs. The use of the lossy transformer is contrary to the common practice in power electronics.

Although the high frequency flux is dampened due to the loss of the core (eddy loss, hysteresis loss, and resistive loss), the lossy transformers still allow sufficient confinement of the magnetic flux and provides sufficient coupling. In addition, the flux also decreases quickly enough. The flux decay process usually takes approximately several microseconds.

Having such a transformer conventionally seems disadvantageous, but for coupling nanosecond to a few microsecond pulses, such a transformer is preferably used. Consequently, the following benefits are achieved: 1) high voltage, high frequency transient coupling from the high-voltage Marx generators to the low-voltage drivers is suppressed; 2) because of the loss in the transformer cores, the residual flux from previous pulses are dissipated faster than common low-loss transformer cores, such that the resetting winding is not needed and is not present.

A benefit of the switch driver 1000 is that it limits the output pulse duration. Because the switch control signals are generated by transformer 1030, even if circuitry generating the input trigger signals at input port Vin were to generate a pulse of indefinite length, the transformer would saturate, causing the control signals to turn off the switches.

Figure 11:
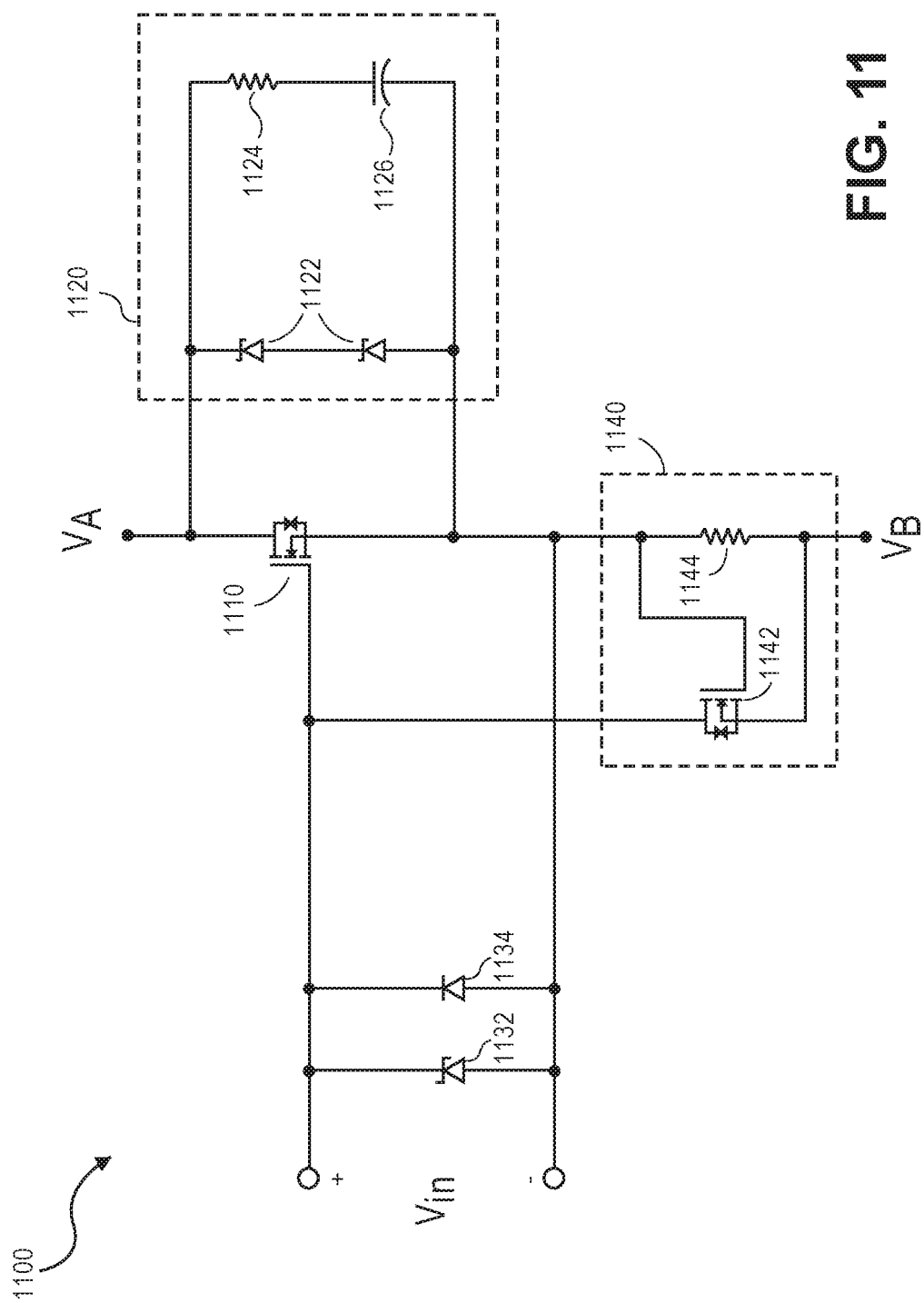
FIG. 11 is an electrical schematic of an alternative switch element.

FIG. 11 illustrates an example of a switch element 1100 comprising components which may be used in the switch stacks discussed here. Switch element 1100 includes switch 1110, and selectively forms a conductive or low resistance path between terminals VA and VB in response to a control voltage applied to input port Vin.

In some embodiments, switch 1110 is a transistor, such as a MOSFET. In some embodiments, switch 1110 is another type of switch. In some embodiments, switch 1110 has a turn on time of less than 5 ns, about 5 ns, about 10 ns, about 25 ns, about 15 ns, about 75 ns, about 100 ns, or greater than 100 ns.

In some embodiments, switch element 1100 also includes snubber circuit 1120. In some embodiments, the turn on times of the switches of the switch stacks are not identical. In order to prevent voltages greater than that which switch 1110 can tolerate, snubber circuit 1120 provides a current shunt path bypassing switch 1110. Diodes 1122 provide a low-frequency current path, and the combination of the capacitor 1126 and resistor 1124 provide a high-frequency current path.

In some embodiments, switch element 1100 also includes optional overcurrent protection circuit 1140. Overcurrent protection circuit 1140 includes switch 1142 and sense resistor 1144.

Current flowing from terminal VA to terminal VB is conducted through sense resistor 1144. Accordingly, a voltage is generated across sense resistor 1144 when the current flows from terminal VA to terminal VB. The generated voltage controls a conductive state of switch 1142. If the current flowing from terminal VA to terminal VB is greater than a threshold, the generated voltage causes the switch 1142 to conduct. As a result, switch 1142 reduces the control voltage of switch 1110. In response to the reduced control voltage, switch 1110 becomes less conductive or turns off. Consequently, the current which may be conducted from terminal VA to terminal VB is limited by overcurrent protection circuit 1140.

In the embodiments discussed herein, MOSFET switches are used. In alternative embodiments, other switches are used. For example, in some embodiments, thyristors, IGBTs or other semiconductor switches are used.

Figure 12:
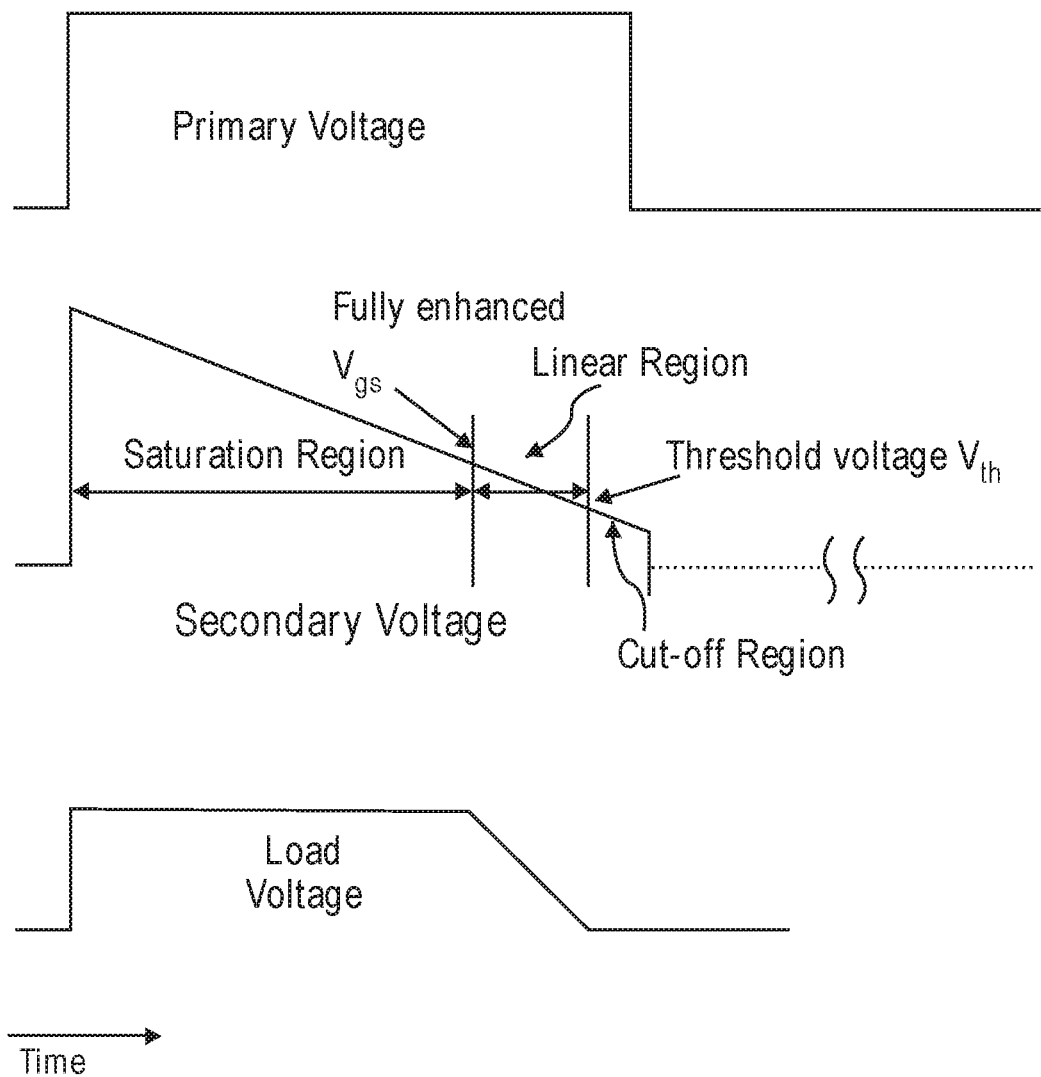
FIG. 12 is a waveform diagram illustrating the operation of a transformer and a control voltage to a MOSFET gate.

An example of the operation of the transformer is illustrated in FIG. 12. The voltage at the input primary inductor is substantially a square waveform, but the voltage at the secondary inductor, which is the MOSFET's gate-source voltage, tapers as the voltage magnitude decreases toward zero, for example, within a period of several microseconds. After a reduction in voltage at the secondary inductor, the switch receiving the voltage enters a linear region of operation from a saturation region of operation when the voltage is lower than the fully enhanced Vgs. As a result, the resistance of the switch increases and the output voltage across the load also shows a tapered profile. When the voltage at the secondary inductor decreases to a value less than the turn-on threshold of a MOSFET (Vth), the MOSFET will be shut off. Once the MOSFET is off, even if the duration of the trigger signal is extended, the voltage at the load goes to zero. The waveform of the voltage at the secondary inductor therefore limits the duration of high voltage output pulses from each panel, for example, to be several microseconds or less.

In some embodiments, the duration of the trigger signal is short enough that the switches remain in saturation because the reduction in voltage at the secondary inductor is insufficient to cause the switches to enter linear region operation. In such embodiments, the load voltage pulses do not exhibit the tapering illustrated in FIG. 12. For example, in such embodiments the load voltage pulses may be substantially square.

In some embodiments, the switch stacks discussed herein include switches, as discussed above, as well as other components.

In some embodiments, when generating pulses of a duration less than a threshold, the shape of the pulses are substantially square. In some embodiments, when generating pulses of the duration greater than a threshold, the shape of the pulses are substantially square for a duration substantially equal (e.g. within 10% or 1%) to the threshold. During the time after the threshold, the voltage of such long pulses drops toward 0 V. In some embodiments, the drop toward 0 V is substantially linear. In some embodiments, the drop toward 0 V is substantially exponential.

Figure 13:
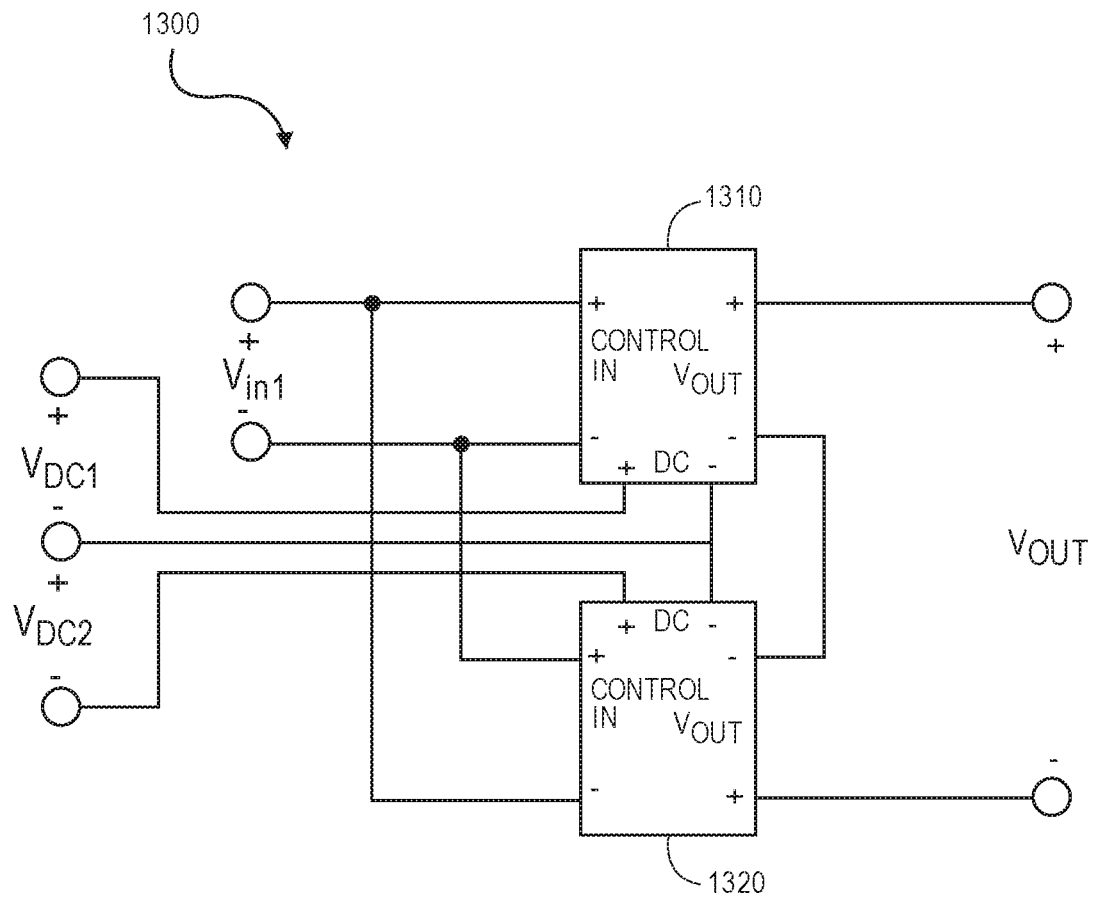
FIG. 13 is an alternative electrical schematic of a pulse generator shown in FIG. 1.

FIG. 13 illustrates an alternative pulse generator circuit 1300 which may be used inside nsPEF system 100 of FIG. 1.

Pulse generator circuit 1300 receives input pulses across input port Vin and DC voltages at input ports VDC1 and VDC2, and generates output pulses across output port Vout in response to the received input pulses and DC voltages.

Pulse generator circuit 1300 includes multiple pulse generator circuits 1310 and 1320. In this embodiment, two pulse generator circuits are used. In alternative embodiments, more pulse generator circuits are used. For example, in some embodiments, 3, 4, 5, 10 or another number of pulse generator circuits having their output ports serially connected, as discussed below with reference to pulse generator circuit 1300, are used.

Each of pulse generator circuits 1310 and 1320 may be similar to the other pulse generator circuits discussed herein. For example pulse generator circuits 1310 and 1320 may be similar to or may be substantially identical to pulse generator circuit 700 discussed above with reference to FIG. 7.

Each of pulse generator circuits 1310 and 1320 receive the same input pulse signal across their respective Control In input ports. In response, each of pulse generator circuits 1310 and 1320 generate high voltage pulses across their respective Vout output ports. Because the Vout output ports of pulse generator circuits 1310 1320 are serially connected, the voltage pulse generated by pulse generator circuits 1310 and 1320 across output port Vout of pulse generator circuit 1300 is substantially equal (e.g. within 10% or 1%) to the sum of the voltages of the pulses respectively generated by pulse generator circuits 1310 and 1320.

Figure 14:
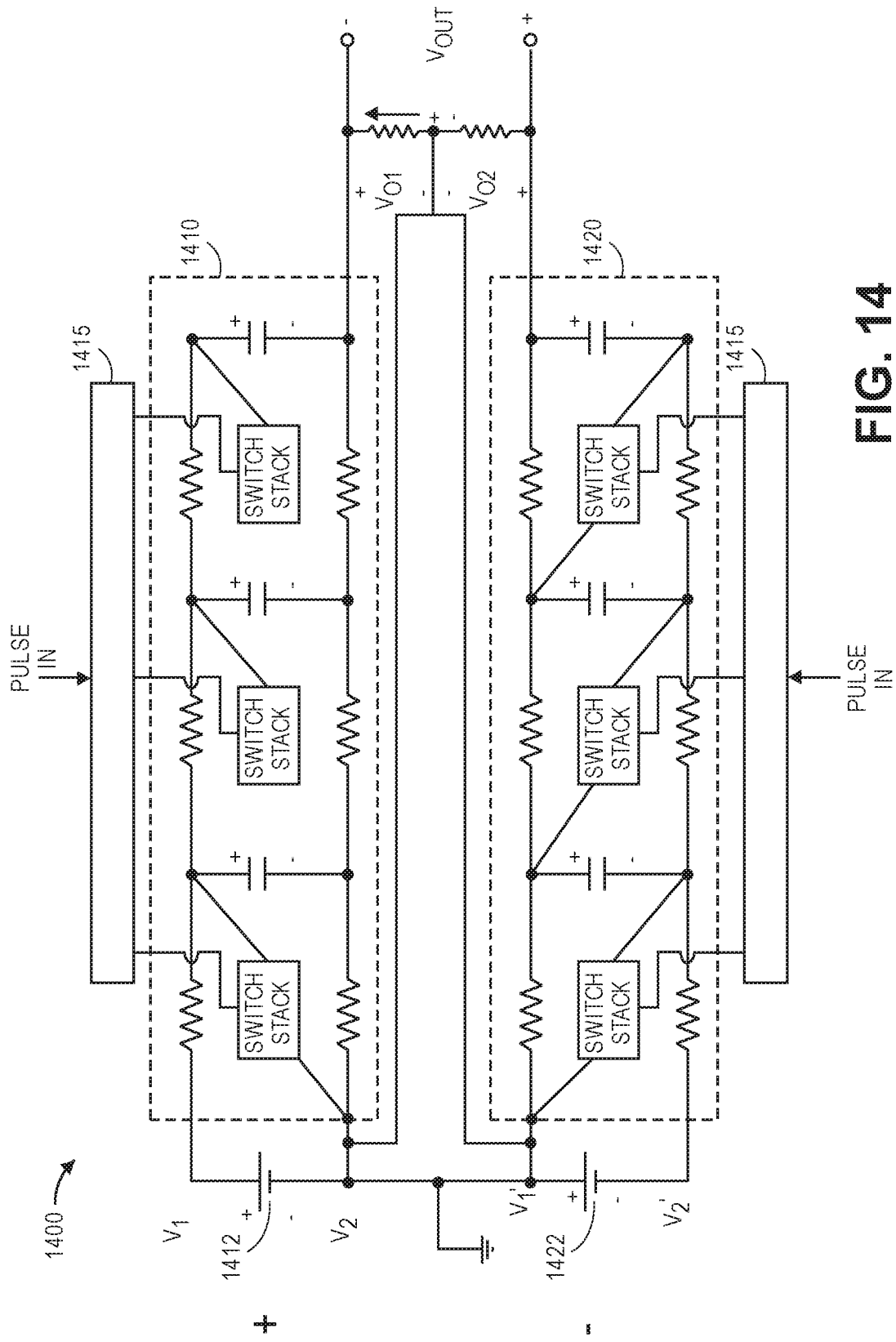
FIG. 14 is an alternative electrical schematic of a pulse generator shown in FIG. 1.

FIG. 14 illustrates an alternative pulse generator circuit 1400 which may be used inside nsPEF system 100 of FIG. 1, and which has characteristics similar to the pulse generator 1300 of FIG. 13. Pulse generator circuit 1400 includes pulse generators 1410 and 1420, drivers 1415 and 1425, and power supplies 1412 and 1422.

Pulse generator circuit 1400 includes multiple pulse generator circuits 1410 and 1420. In this embodiment, two pulse generator circuits are used. In alternative embodiments, more pulse generator circuits are used. Each of pulse generator circuits 1410 and 1420 may be similar to the other pulse generator circuits discussed herein.

Pulse generator circuit 1400 receives input pulses at each of drivers 1415 and 1425, which may be similar to driver 850 discussed above with reference to FIG. 8. Pulse generator circuit 1400 generates output pulses across output port Vout in response to the received input pulses. The output voltage pulses are also based on power voltages received from power supplies 1412 and 1422.

Each of drivers 1415 and 1425 receive an input pulse signal. In response to the received input signals, drivers 1415 and 1425 respectively generate driving signal pulses for pulse generator circuits 1410 and 1420. In response to the driving signal pulses, each of pulse generator circuits 1410 and 1420 generate high voltage pulses across their respective output ports Vo1 and Vo2. Because the Vo1 and Vo2 output ports of pulse generator circuits 1410 and 1420 are serially connected, the voltage pulse generated by pulse generator circuits 1410 and 1420 across output port Vout of pulse generator circuit 1400 is substantially equal (e.g. within 10% or 1%) to the sum of the voltages of the pulses respectively generated by pulse generator circuits 1410 and 1420.

In this embodiment, pulse generator circuit 1410 generates a high voltage pulse across its output port Vo1 which is substantially equal (e.g. within 10% or 1%) to three times the voltage of power supply 1412, $(-3\times[V1-V2])$. In addition, pulse generator circuit 1420 generates a high voltage pulse across its output port Vo2 which is substantially equal (e.g. within 10% or 1%) to three times the voltage of power supply 1414 $(3\times[V'1-V'2])$. As a result, pulse generator circuit 1400 generates a voltage of $(3\times[V'1-V'2])-(-3\times[V1-V2])$ across its output port Vout.

In some embodiments, a single driver circuit connected to both pulse generator circuit 1410 and 1420 is used instead of drivers 1415 and 1425. In such embodiments, the single driver circuit generates driving signal pulses for both pulse generator circuits 1410 and 1420 in response to an input pulse signal.

Figure 15:
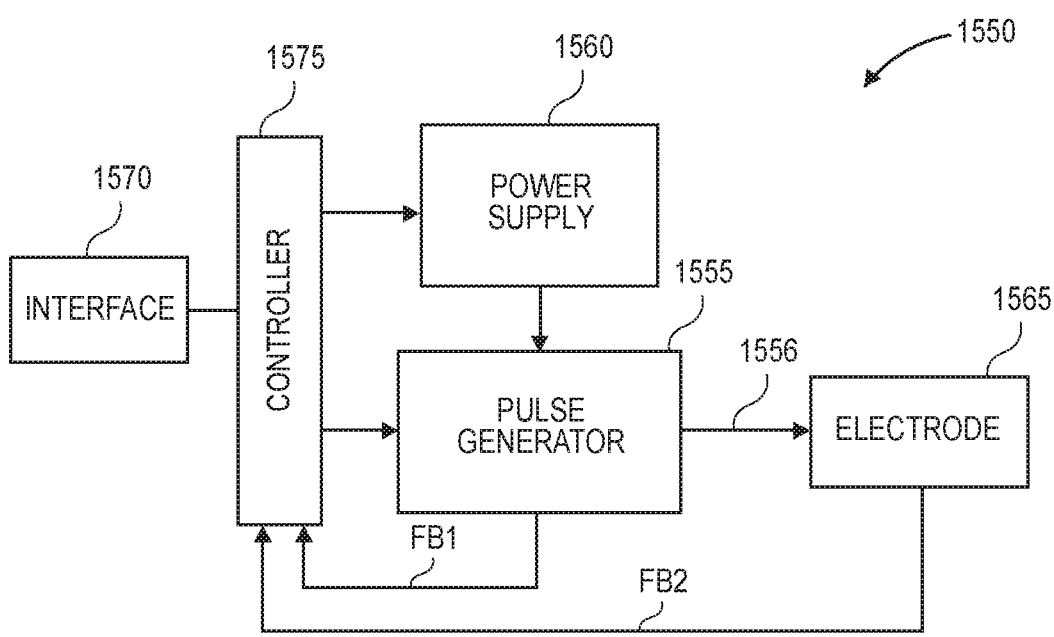
FIG. 15 is a block diagram of a nsPEF treatment system.

FIG. 15 is a block diagram of a nsPEF treatment system 1550, which has characteristics similar to or identical to those of nsPEF system 100 illustrated in FIG. 1. NsPEF treatment system 1550 includes pulse generator 1555, power supply 1560, electrode 1565, interface 1570, and controller 1575.

Pulse generator 1555 may be similar or identical to any of the pulse generator circuits discussed herein. For example, pulse generator 1555 may be configured to generate pulses having a voltage magnitude corresponding with power voltages received from power supply 1560 and having pulse widths and other characteristics corresponding with control signals received from controller 1575. In alternative embodiments, other pulse generator circuits may be used.

Electrode 1565 may be similar or identical to any of the electrodes discussed herein. For example, electrode 1565 may be similar or identical to electrodes 300 and 400 discussed above with reference to FIGS. 3 and 4. Electrode 1565 is configured to receive nsPEF pulses generated by pulse generator 1555 from conductor 1556 and is configured to deliver nsPEF pulses to a patient undergoing therapeutic nsPEF treatment. In alternative embodiments, other therapeutic electrodes may be used.

Power supply 1560 is configured to provide power voltages to pulse generator 1555. For example, in embodiments where pulse generator 1555 is similar to pulse generator circuit 700 illustrated in FIG. 7, power supply 1560 may be configured to provide power voltages corresponding with power voltages V1 and V2 of pulse generator circuit 700. In some embodiments, power supply 1560 generates and provides power voltages which have a voltage level corresponding with a control signal from controller 1575.

Interface 1570 is configured to receive input from a user identifying various parameters and characteristics of the nsPEF pulses to be applied to the patient. For example, interface 1570 may be configured to receive input identifying or specifying values for one or more characteristics of one or more nsPEF pulses to be applied to the patient. For example, the characteristics may include one or more of an amplitude, a polarity, a width, a rise time, and a fall time of one or more nsPEF pulses to be applied to the patient. Additionally or alternatively, the characteristics may include one or more of a frequency and a pulse quantity of a sequence of nsPEF pulses to be applied to the patient. Furthermore, the characteristics may additionally or alternatively include a result of the nsPEF pulses to be applied to the patient, such as a maximum temperature for the treated tissue of the patient. Other characteristics may additionally or alternatively be identified or specified by the received input.

In addition, interface 1570 is configured to communicate the characteristics identified or specified by the received input to controller 1575.

Controller 1575 is configured to generate and provide one or more control signals to pulse generator 1555 and to power supply 1560 based at least partly on the communicated characteristics received from interface 1570. Additionally, pulse generator 1555, power supply 1560, and electrode 1565 are collectively configured to, in response to the control signals from controller 1575, generate nsPEF pulses having characteristics corresponding with the control signals.

In this embodiment, one or both of pulse generator 1555 and electrode 1565 are configured to generate feedback signals FB1 and FB2 corresponding with or representing measured parametric characteristics of the nsPEF pulses applied to the patient. In some embodiments, the parametric characteristics of the nsPEF pulses represented by the feedback signals FB1 and FB2 include one or more of an amplitude, a polarity, a width, a rise time, and a fall time of the nsPEF pulses. Additionally or alternatively, the parametric characteristics may include a frequency of a sequence of nsPEF pulses. Furthermore, the parametric characteristics may additionally or alternatively include a temperature of the treated tissue of the patient. The feedback signals FB1 and FB2 may correspond or represent other measured parametric characteristics of one or more of the nsPEF pulses applied to the patient, the patient, the environment, and the nsPEF treatment system 1550.

In some embodiments, controller 1575, power supply 1560, pulse generator 1555, and electrode 1565 collectively form a feedback loop which causes one or more parametric characteristics of the nsPEF pulses applied to the patient to have measured values substantially equal (e.g. within 10% or 1%) to the values of corresponding characteristics identified in the input received by interface 1570.

For example, interface 1570 may receive input specifying a value of 15 kV for an amplitude of the nsPEF pulses applied to the patient. In addition, the controller 1575 may be configured to, in response to a feedback signal FB2 from electrode 1565 or a feedback signal FB1 from pulse generator 1555 indicating that the measured amplitude of the nsPEF pulses applied to the patient is less than (or greater than) 15 kV, change a control signal provided to power supply 1560. In response to the changed control signal, power supply 1560 may be configured to increase (or decrease) the voltage of power signals provided to pulse generator 1555 such that the amplitude of the nsPEF pulses generated and applied to the patient increases (or decreases) to or toward 15 kV.

Similarly, interface 1570 may receive input specifying a value of 150 ns for a pulse width of the nsPEF pulses applied to the patient. The controller 1575 may be configured to, in response to a feedback signal FB2 from electrode 1565 or a feedback signal FB1 from pulse generator 1555 indicating that the measured pulse width of the nsPEF pulses applied to the patient is greater than (or less than) 150 ns, change a control signal provided to pulse generator 1555. In response to the changed control signal, pulse generator 1555 may be configured to generate and apply to the patient nsPEF pulses having decreased (or increased) pulse width. As a result, the feedback signal FB1 or FB2 causes the controller 1575 to generate control signals which cause the pulse generator 1555 to generate and apply nsPEF pulses having pulse widths decreased (or increased) to or toward 150 ns.

In some embodiments, the feedback loop is controlled using a Proportional-Integral-Derivative (PID) method. For example, controller 1575 may be configured to continuously or substantially continuously calculate an error value as the difference between a desired value perceived at interface 1570 and a corresponding measured parameter. In addition, controller 1575 may be configured to continuously or substantially continuously calculate the control signals as a sum of one or more of: a first constant times the error signal, a second constant times an integral of the error signal, and a third constant times a derivative of the error signal.

In some embodiments, the feedback loop is controlled using a lookup table to determine a next value based on a measured value. In some embodiments, the feedback loop is controlled by reducing or increasing a value by a fixed amount or step size based on a determination of whether a measured value is greater than or less than a threshold.

Figure 16:
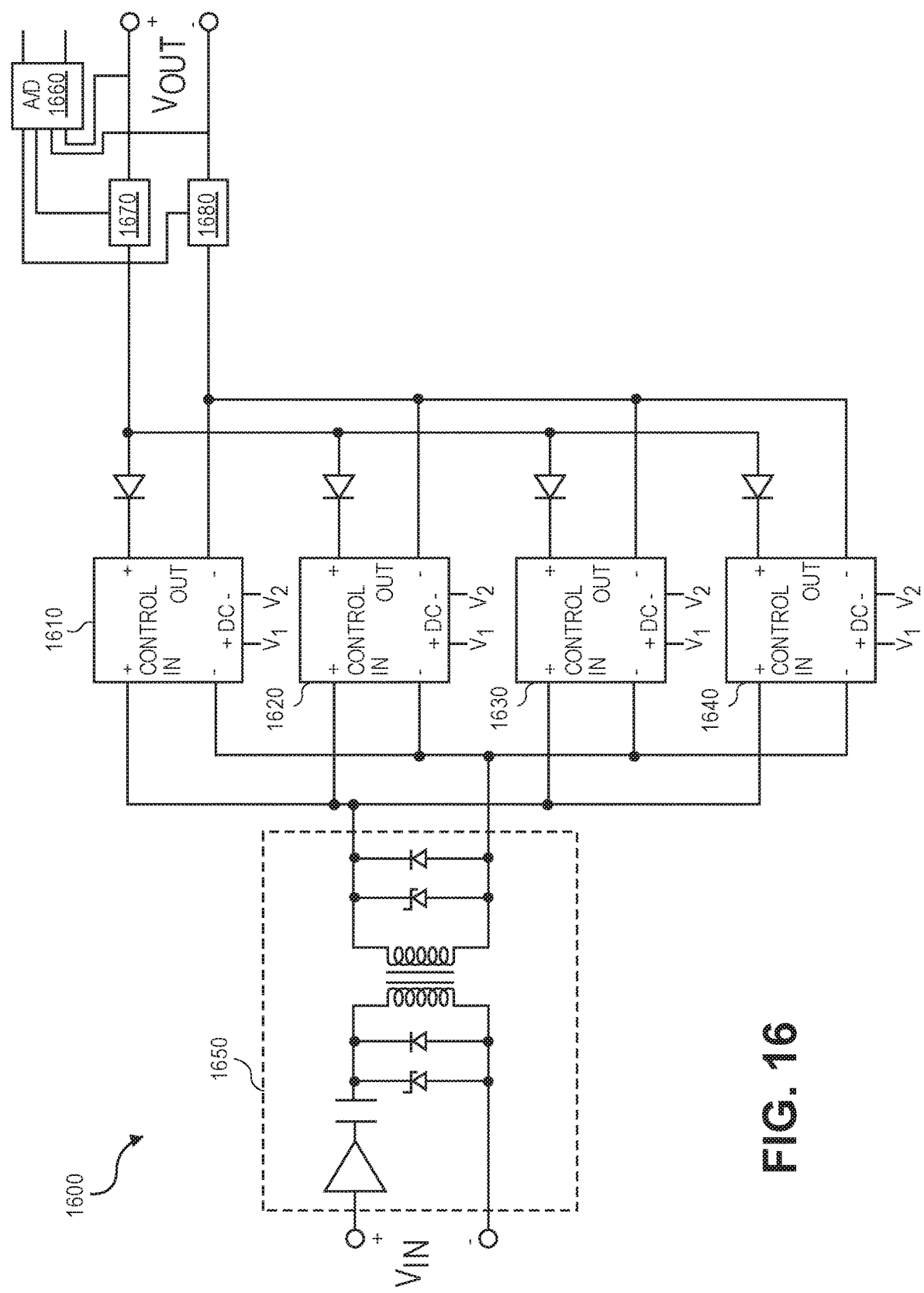
FIG. 16 is a schematic illustration of an alternative pulse generator.

FIG. 16 illustrates an alternative pulse generator 1600 which may be used as pulse generator 1555 of nsPEF treatment system 1550 illustrated in FIG. 15. Pulse generator 1600 may have features similar to or identical to other pulse generator circuits discussed herein. For example, pulse generator circuit 1600 may have features similar to or identical to pulse generator circuit 700 of FIG. 7.

For example, pulse generator 1600 includes the driver circuit 1650 which may be similar to or identical to driver 750 of pulse generator circuit 700. In addition, pulse generator 1600 includes pulse generator circuits 1610, 1620, 1630, and 1640, which may respectively be similar or identical to pulse generator circuits 710, 720, 730, and 740.

Pulse generator 1600 also includes, or in some embodiments is connected to, analog-to-digital converter 1660. Furthermore, pulse generator 1600 additionally or alternatively includes, or in some embodiments is connected to, current monitors 1670 and 1680.

In this embodiment, analog-to-digital (A/D) converter 1660 includes a first channel having inputs which are respectively connected to the positive (+) and negative (−) voltage output terminals of pulse generator 1600. In some embodiments, a first low input impedance differential buffer (not shown) is connected to the positive (+) and negative (−) voltage output terminals of pulse generator 1600, and drives the inputs of analog-to-digital converter 1660. In some embodiments, a probe, such as a Tektronix P6015A Passive High Voltage Probe (not shown) is connected to the positive (+) and negative (−) voltage output terminals of pulse generator 1600, and drives the inputs of analog-to-digital converter 1660.

In addition, analog-to-digital converter 1660 is configured to generate a first digital output representing the voltage difference between the positive (+) and negative (−) voltage output terminals of pulse generator 1600. When used in the nsPEF treatment system 1650 of FIG. 15, the first digital output may be used as a feedback signal for controller 1675.

In some embodiments, analog-to-digital converter 1660 generates the first digital output based on either, but not both, of the voltages at the positive (+) and negative (−) voltage output terminals.

In this embodiment, analog-to-digital converter 1660 also includes a second channel having inputs which are respectively connected to the current monitors 1670 and 1680, and the current monitors 1670 and 1680 are respectively connected to the positive (+) and negative (−) voltage output terminals of pulse generator 1600. In some embodiments, a second low input impedance differential buffer (not shown) is connected to the current monitors 1670 and 1680, and drives the inputs of analog-to-digital converter 1660.

In addition, analog-to-digital converter 1660 is configured to generate a second digital output representing the current difference between the currents flowing through positive (+) and negative (−) voltage output terminals of pulse generator 1600. When used in the nsPEF treatment system 1550 of FIG. 15, the second digital output may be used as a feedback signal for controller 1575. In some embodiments, analog-to-digital converter 1660 generates the second digital output based on either, but not both, of inputs from the current monitors 1670 and 1680.

In some embodiments, current monitors 1670 and 1680 each include a sense resistor and an amplifier. The sense resistor is configured to generate a voltage response of the current flowing therethrough, and the amplifier generates an input for the analog-to-digital converter based on the voltage across the sense resistor.

In some embodiments, current monitors 1670 and 1680 include a current monitor, such as Pearson Current Monitor 2878, which generates a voltage in response to a sensed current.

In some embodiments, pulse generator 1600 generates either, but not both, of the first and second digital outputs. In some embodiments, one or more single channel analog-to-digital converters are used instead of or in addition to analog-to-digital converter 1660.

Figure 17:
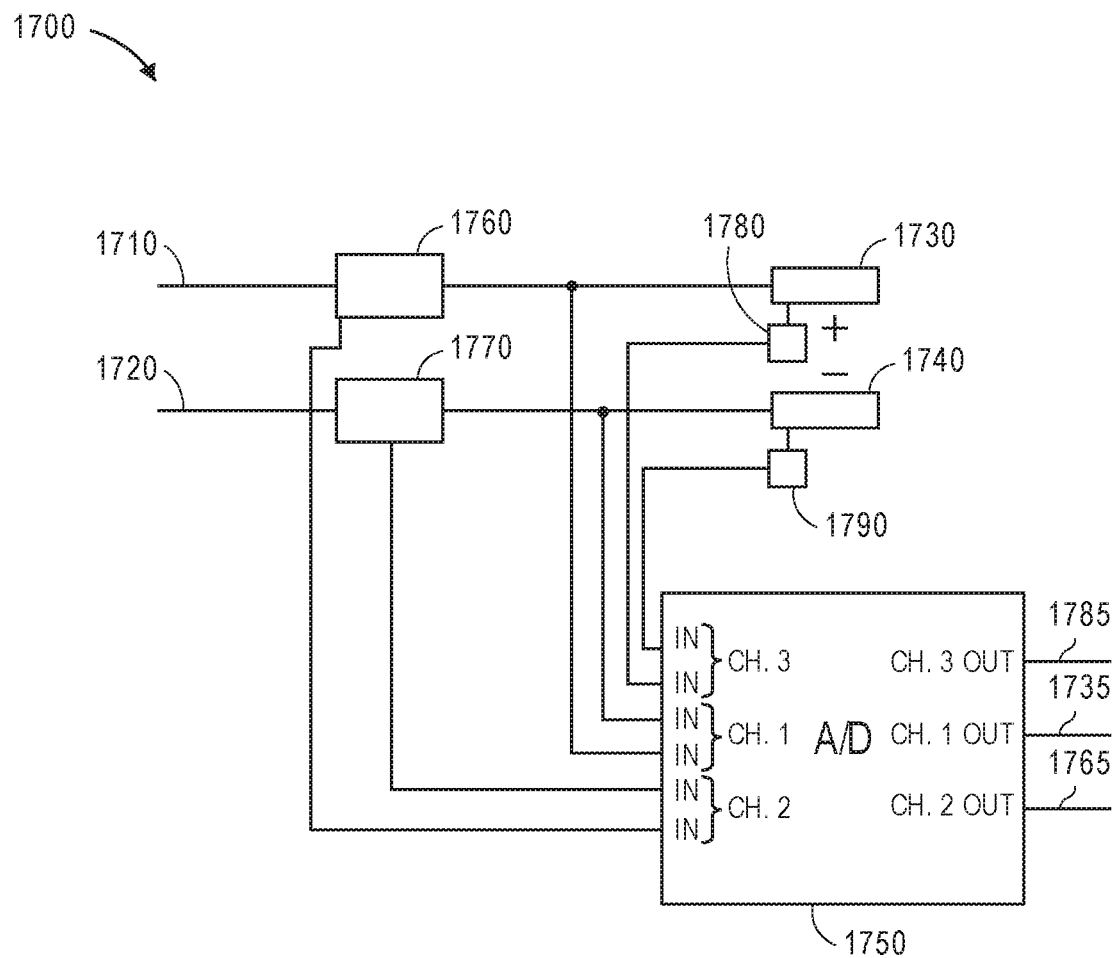
FIG. 17 is a schematic illustration of an electrode which may be used in the nsPEF treatment system of FIG. 15.

FIG. 17 is a schematic illustration of an electrode 1700 which may, for example, be used as electrode 1565 in nsPEF treatment system 1550 of FIG. 15. Electrode 1700 may be similar or identical to any of the electrodes discussed herein. For example, electrode 1700 may be similar or identical to electrodes 300 and 400 discussed above with reference to FIGS. 3 and 4.

Electrode 1700 is configured to receive nsPEF pulses across input terminals 1710 and 1720 and to deliver nsPEF pulses to a patient undergoing therapeutic nsPEF treatment through positive (+) and negative (−) output therapeutic electrode terminals 1730 and 1740.

Electrode 1700 includes, or in some embodiments is connected to, analog-to-digital converter 1750. Furthermore, electrode 1700 additionally or alternatively includes, or in some embodiments is connected to, current monitors 1760 and 1770. In addition, electrode 1700 includes thermal sensors 1780 and 1790. In some embodiments, electrode 1700 includes either but not both of thermal sensors 1780 and 1790.

In this embodiment, analog-to-digital converter 1750 includes a first channel having inputs which are respectively connected to the positive (+) and negative (−) voltage output therapeutic electrode terminals 1730 and 1740. In some embodiments, a first low input impedance differential buffer (not shown) is connected to the positive (+) and negative (−) voltage output therapeutic electrode terminals 1730 and 1740 and drives the inputs of the first channel of analog-to-digital converter 1750. In some embodiments, a probe, such as a Tektronix P6015A Passive High Voltage Probe (not shown) is connected to the positive (+) and negative (−) voltage output therapeutic electrode terminals 1730 and 1740, and drives the inputs of analog-to-digital converter 1750.

In addition, analog-to-digital converter 1750 is configured to generate a first digital output at output terminal 1735 representing the voltage difference between the positive (+) and negative (−) voltage output therapeutic electrode terminals 1730 and 1740. When used in the nsPEF treatment system 1650 of FIG. 15, the first digital output may be used as a feedback signal for controller 1575. In some embodiments, analog-to-digital converter 1750 generates the first digital output based on either, but not both, of the voltages at the positive (+) and negative (−) voltage output therapeutic electrode terminals 1730 and 1740.

In this embodiment, analog-to-digital converter 1750 also includes a second channel having inputs which are respectively connected to the current monitors 1760 and 1770, and the current monitors 1760 and 1770 are respectively connected to the positive (+) and negative (−) voltage output therapeutic electrode terminals 1730 and 1740. In some embodiments, a second low input impedance differential buffer (not shown) is connected to the current monitors 1760 and 1770 and drives the inputs of the second channel of analog-to-digital converter 1750.

In addition, analog-to-digital converter 1750 is configured to generate a second digital output at output terminal 1765 representing the current difference between the currents flowing through positive (+) and negative (−) voltage output therapeutic electrode terminals 1730 and 1740. When used in the nsPEF treatment system 1550 of FIG. 15, the second digital output may be used as a feedback signal for controller 1575. In some embodiments, analog-to-digital converter 1750 generates the second digital output based on either, but not both, of inputs from the current monitors 1760 and 1770.

In this embodiment, analog-to-digital converter 1750 also includes a third channel having inputs which are respectively connected to the thermal sensors 1780 and 1790, and the thermal sensors 1780 and 1790 are respectively thermally coupled to the positive (+) and negative (−) voltage output therapeutic electrode terminals 1730 and 1740. In some embodiments, a third low input impedance differential buffer (not shown) is connected to the thermal sensors 1780 and 1790, and drives the inputs of the third channel of analog-to-digital converter 1750.

In addition, analog-to-digital converter 1750 is configured to generate a third digital output at output terminal 1785 representing a temperature of at least one of positive (+) and negative (−) voltage output therapeutic electrode terminals 1730 and 1740. When used in the nsPEF treatment system 1550 of FIG. 15, the third digital output may be used as a feedback signal for controller 1575. In some embodiments, analog-to-digital converter 1750 generates the third digital output based on either, but not both, of inputs from the thermal sensors 1780 and 1790.

In various embodiments, pulse generator 1700 generates any one, two, or all of the first, second, and third digital outputs. In some embodiments, one or more single channel analog-to-digital converters are used instead of or in addition to analog-to-digital converter 1750.

Figure 18:
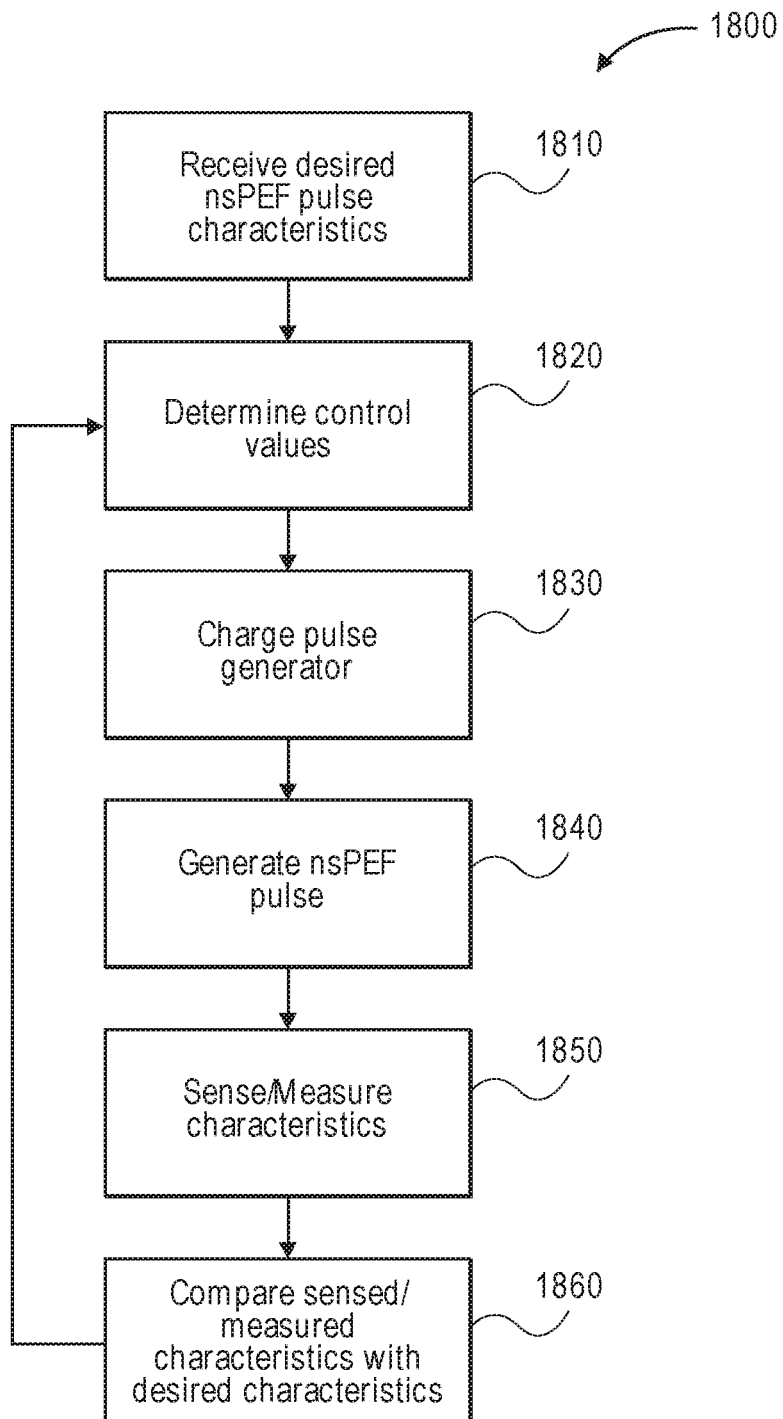
FIG. 18 is a flowchart illustration of methods of using an nsPEF treatment system.

FIG. 18 is a flowchart illustration of a method 1800 of using an nsPEF treatment system, such as nsPEF treatment system 1550 of FIG. 15. In the method, the nsPEF treatment system implements a feedback loop to control a parameter of the treatment. Because of one or more factors including, but not limited to, manufacturing variation, temperature, and system age, realized or measured parameters during treatment tend to have values somewhat different from the corresponding values with which the system was programmed. To increase accuracy of the system, the feedback loop actively measures and controls realized parameters so that the measured parameters more closely match the desired or programmed values.

At 1810, information representing one or more desired characteristics of a patient or of nsPEF pulses to be applied to the patient is received at an interface, such as interface 1570 of nsPEF treatment system 1550.

At 1820, a controller, such as controller 1575 of nsPEF treatment system 1550, generates control values corresponding with the values of the desired characteristics received at the interface.

At 1830, a power supply, such as power supply 1560 of nsPEF treatment system 1550, charges a pulse generator, such as pulse generator 1555 of nsPEF treatment system 1550. The power supply charges the pulse generator with a voltage value determined based on one or more control signals received from the controller, where the received one or more control signals correspond with one or more control values generated at 1820.

At 1840, at least one nsPEF pulse is generated. In some embodiments, the at least one generated nsPEF pulse is applied to the patient. For example, in response to one or more control signals from the controller, the pulse generator may generate the nsPEF pulse. In addition, an electrode, such as electrode 1565, may apply the nsPEF pulse to the patient. In some embodiments, the nsPEF pulse is applied to the patient as part of a treatment regimen. In some embodiments, the nsPEF pulse is applied to the patient as part of a characterization, set up, or calibration of the nsPEF treatment system. In some embodiments, the nsPEF pulse is not applied to the patient.

At 1850, one or more electrical characteristics of the nsPEF pulse or of the patient are measured or sensed, for example, while the nsPEF pulse is applied to the patient.

At 1860, a value of the measured or sensed characteristic is compared with the value of a corresponding desired characteristic as represented by the received information at 1810.

Returning to 1820, the controller modifies the control values corresponding with the values of the desired characteristics received at the interface according to the results of the comparison performed at 1860. The controller is configured to modify the control values so that, because of the modification to the control value, the value of a next measured or sensed characteristic is expected to be closer to the desired value of the characteristic than the value of the previously measured or sensed characteristic.

Figure 19:
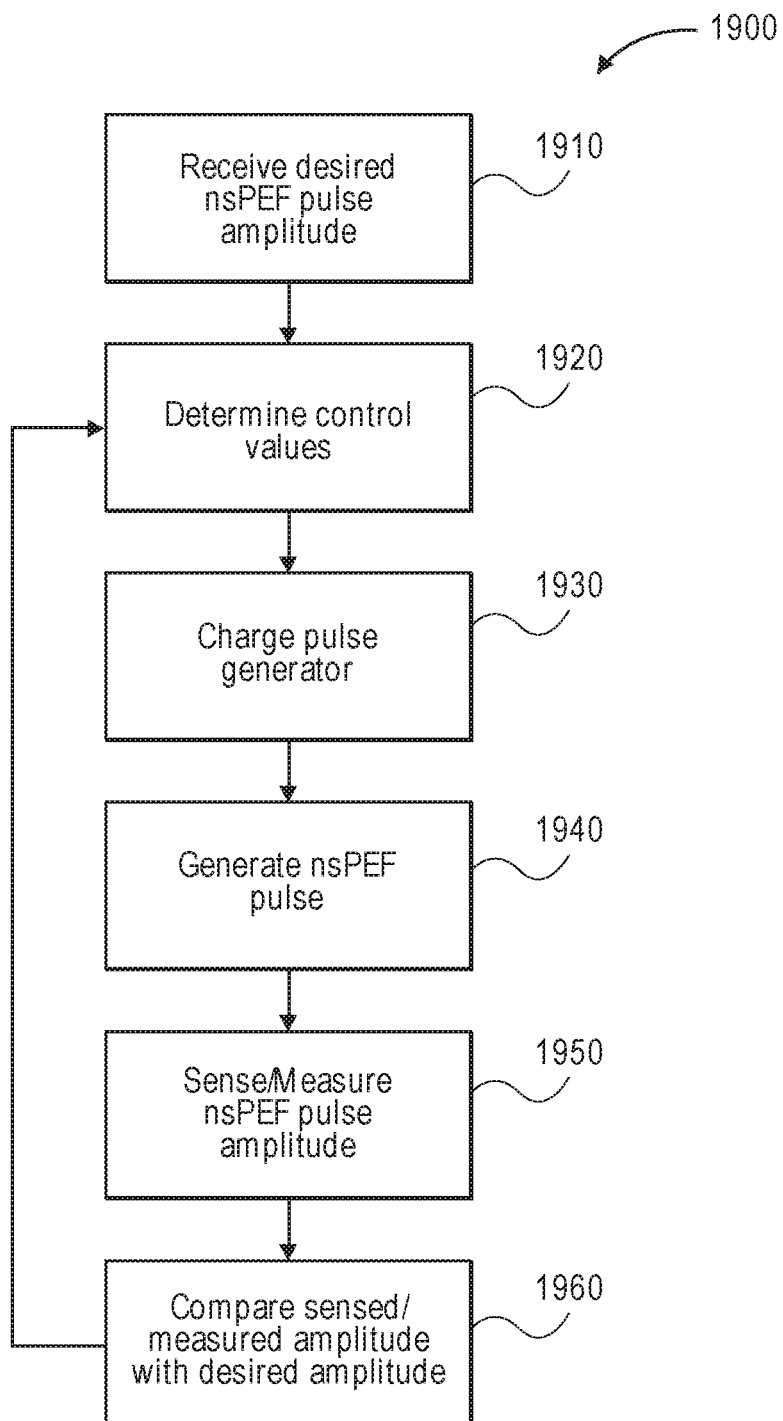
FIG. 19 is a flowchart illustration of methods of using an nsPEF treatment system.

FIG. 19 is a flowchart illustration of a method 1900 of using an nsPEF treatment system, such as nsPEF treatment system 1550 of FIG. 15.

At 1910, information representing a current or voltage amplitude of nsPEF pulses to be applied to the patient is received at an interface, such as interface 1570 of nsPEF treatment system 1550.

At 1920, a controller, such as controller 1575 of nsPEF treatment system 1550, generates control values corresponding with the desired amplitude.

At 1930, a power supply, such as power supply 1560 of nsPEF treatment system 1550, charges a pulse generator, such as pulse generator 1555 of nsPEF treatment system 1550. The power supply charges the pulse generator with a voltage value determined based on one or more control signals received from the controller, where the received one or more control signals correspond with one or more control values generated at 1920.

At 1940, at least one nsPEF pulse is generated. In some embodiments, the at least one generated nsPEF pulse is applied to the patient. For example, in response to one or more control signals from the controller, the pulse generator may generate an nsPEF pulse. In addition, an electrode, such as electrode 1565, may apply the nsPEF pulse to the patient. In some embodiments, the nsPEF pulse is applied to the patient as part of a treatment regimen. In some embodiments, the nsPEF pulse is applied to the patient as part of a characterization, set up, or calibration of the nsPEF treatment system. In some embodiments, the nsPEF pulse is not applied to the patient.

At 1950, the amplitude of the nsPEF pulse is measured or sensed, for example, while the nsPEF pulse is applied to the patient.

At 1960, a value of the measured or sensed amplitude is compared with the amplitude as represented by the received information at 1910.

Returning to 1920, the controller modifies the control values corresponding with the values of the desired amplitude received at the interface according to the results of the comparison performed at 1960. The controller is configured to modify the control values so that if the measured or sensed value of the amplitude is less than the desired amplitude, the modified control values will cause the power supply to charge the pulse generator with a voltage of greater value than previously used. Likewise, the controller is additionally configured to modify the control values so that if the measured or sensed value of the amplitude is greater than the desired amplitude, the modified control values will cause the power supply to charge the pulse generator with a voltage of less value than previously used.

Figure 20:
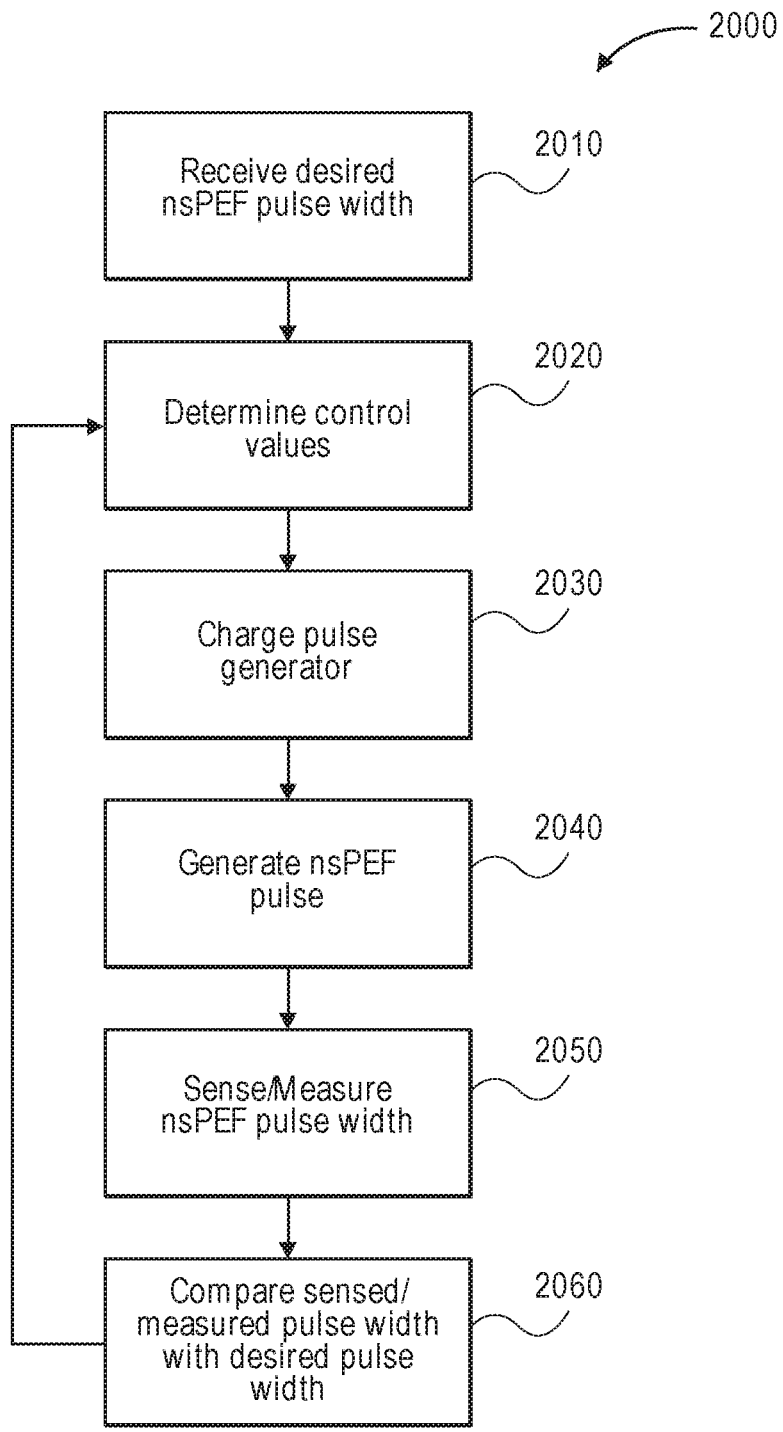
FIG. 20 is a flowchart illustration of methods of using an nsPEF treatment system.

FIG. 20 is a flowchart illustration of a method 2000 of using an nsPEF treatment system, such as nsPEF treatment system 1550 of FIG. 15.

At 2010, information representing a pulse width of nsPEF pulses to be applied to the patient is received at an interface, such as interface 1570 of nsPEF treatment system 1550.

At 2020, a controller, such as controller 1575 of nsPEF treatment system 1550, generates control values corresponding with the desired pulse width.

At 2030, a power supply, such as power supply 1560 of nsPEF treatment system 1550, charges a pulse generator, such as pulse generator 1555 of nsPEF treatment system 1550. The power supply charges the pulse generator with a voltage value determined based on one or more control signals received from the controller.

At 2040, at least one nsPEF pulse is generated. In some embodiments, the at least one generated nsPEF pulse is applied to the patient. For example, in response to one or more control signals from the controller, the pulse generator may generate an nsPEF pulse. In addition, an electrode, such as electrode 1565, may apply the nsPEF pulse to the patient. In some embodiments, the nsPEF pulse is applied to the patient as part of a treatment regimen. In some embodiments, the nsPEF pulse is applied to the patient as part of a characterization, set up, or calibration of the nsPEF treatment system. In some embodiments, the nsPEF pulse is not applied to the patient.

At 2050, the pulse width of the nsPEF pulse is measured or sensed, for example, while the nsPEF pulse is applied to the patient.

At 2060, a value of the measured or sensed pulse width is compared with the pulse width as represented by the received information at 2010.

Returning to 2020, the controller modifies the control values corresponding with the values of the desired pulse width received at the interface according to the results of the comparison performed at 2060. The controller is configured to modify the control values so that if the measured or sensed value of the pulse width is less than the desired pulse width, the modified control values will cause the pulse generator to generate further nsPEF pulses with a pulse width of greater value than previously generated. Likewise, the controller is configured to modify the control values so that if the measured or sensed value of the pulse width is greater than the desired pulse width, the modified control values will cause the pulse generator to generate further nsPEF pulses having a pulse width of less value than previously generated.

Figure 21:
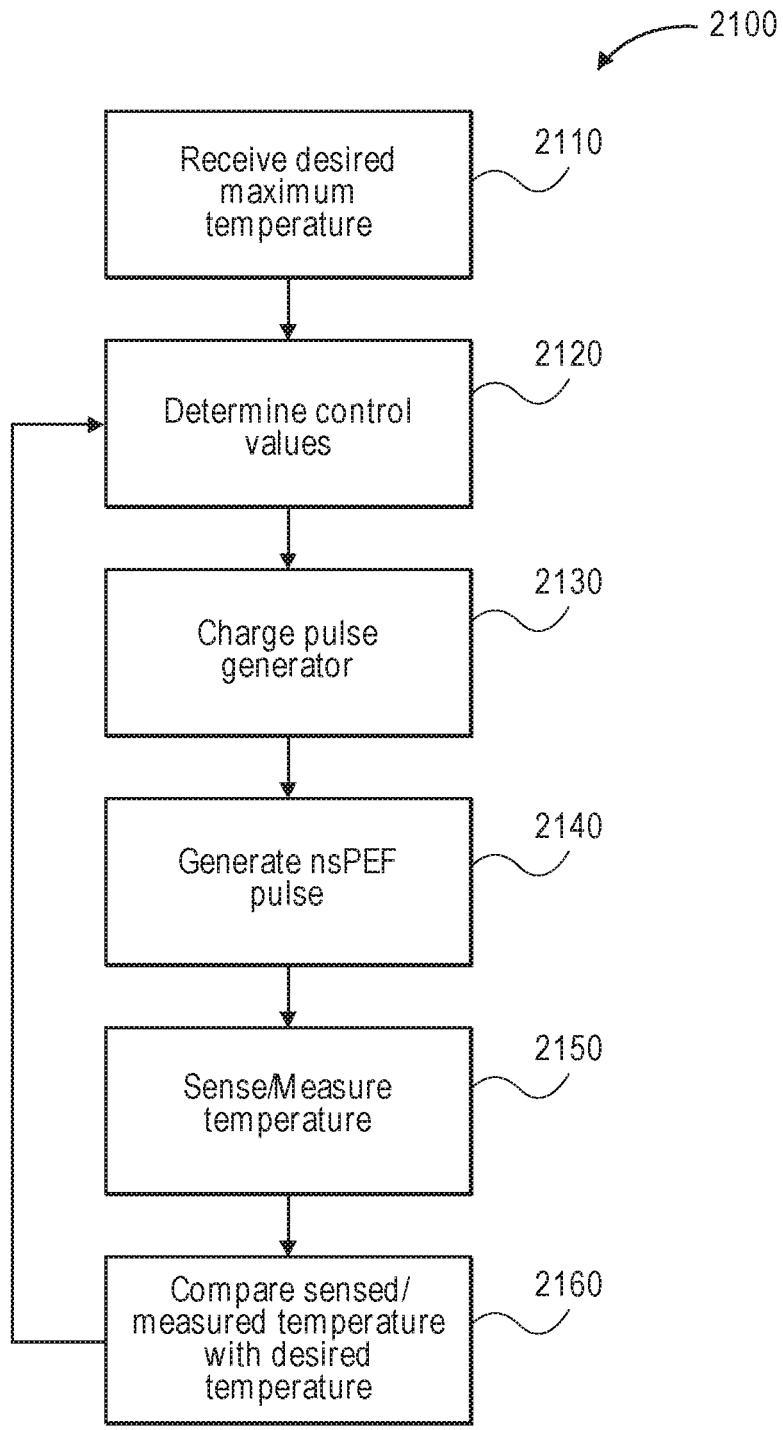
FIG. 21 is a flowchart illustration of methods of using an nsPEF treatment system.

FIG. 21 is a flowchart illustration of a method 2100 of using an nsPEF treatment system, such as nsPEF treatment system 1550 of FIG. 15.

At 2110, information representing a maximum tissue temperature of the patient being treated with nsPEF pulses is received at an interface, such as interface 1570 of nsPEF treatment system 1550.

At 2120, a controller, such as controller 1575 of nsPEF treatment system 1550, generates control values corresponding with the desired maximum tissue temperature.

At 2130, a power supply, such as power supply 1560 of nsPEF treatment system 1550, charges a pulse generator, such as pulse generator 1555 of nsPEF treatment system 1550. The power supply charges the pulse generator with a voltage value determined based on one or more control signals received from the controller.

At 2140, one or more nsPEF pulses are generated. In some embodiments, the generated nsPEF pulses are applied to the patient. For example, in response to one or more control signals from the controller, the pulse generator may generate the nsPEF pulses. In addition, an electrode, such as electrode 1565, may apply the nsPEF pulses to the patient. In some embodiments, the nsPEF pulses are applied to the patient as part of a treatment regimen. In some embodiments, the nsPEF pulses are applied to the patient as part of a characterization, set up, or calibration of the nsPEF treatment system. In some embodiments, the nsPEF pulses are not applied to the patient.

At 2150, the temperature of the patient is measured or sensed with a temperature sensor, for example, while the nsPEF pulses are applied to the patient.

At 2160, a value of the measured or sensed temperature is compared with the maximum temperature as represented by the received information at 2110.

Returning to 2120, the controller modifies the control values corresponding with the values of the desired maximum temperature received at the interface according to the results of the comparison performed at 2160. The controller is configured to modify the control values so that if the measured or sensed value of the temperature is greater than the maximum temperature or is greater than a threshold less than the maximum temperature, the modified control values will cause the nsPEF treatment system to deliver less power to the patient. For example, the modified control values may cause nsPEF pulses having less pulse width to be generated. Alternatively or additionally, the modified control values may cause nsPEF pulses with lower frequency to be generated.

Figure 22:
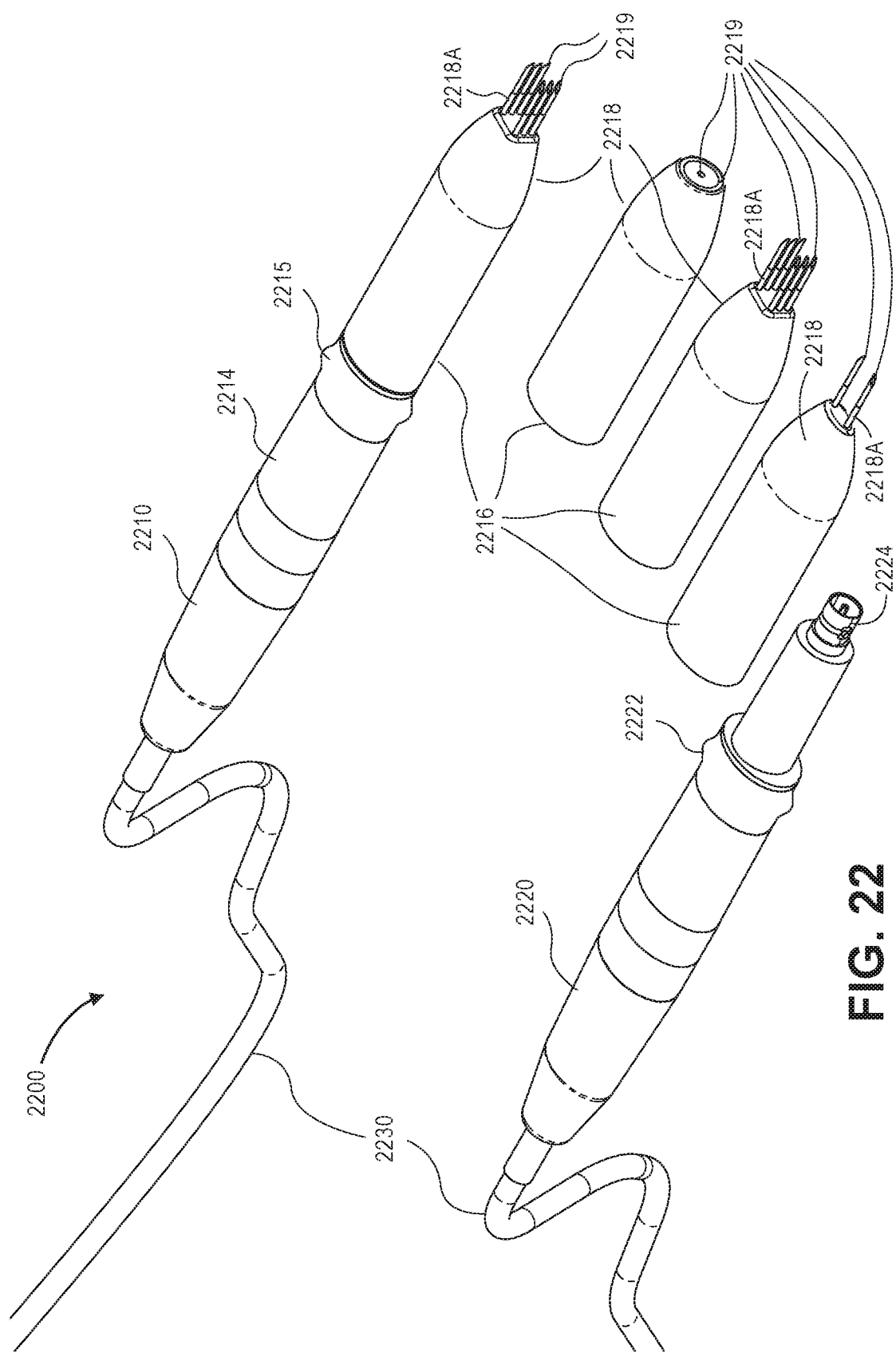
FIG. 22 is an illustration of an electrode which may be used in the nsPEF treatment systems discussed herein.

FIG. 22 is an illustration of an electrode 2200 which may be used in the nsPEF treatment systems discussed herein. For example, electrode 2200 may be used to treat a patient with nsPEF pulses. Electrode 2200 includes therapeutic electrode terminals 2219, which are electrically connected to cable 2230 through tip 2216 and handle 2214.

Electrode 2210 includes handle 2214 and removable, and in some embodiments, disposable, tip 2216. Several embodiments of tips 2216 are illustrated. Other embodiments are contemplated.

Tips 2216 include an electrically insulative portion 2218 and an electrically conductive terminals 2219 configured to contact the patient, for example by piercing tissue, and deliver nsPEF pulses to the patient at the points of contact.

In some embodiments, insulative portion 2218 includes extensions 2218A, which each surround a portion of one of the electrically conductive terminals 2219. In some embodiments, the lengths of the extensions 2218A are adjustable with respect to the surface of insulative portion 2218 from which they extend, such that the exposed portion of the electrically conductive terminals 2219 is adjustable. In some embodiments, the lengths of the electrically conductive terminals 2219 are additionally or alternatively adjustable with respect to the surface.

As shown, the handle of 2214 includes finger stop 2215, which is spaced apart from high-voltage terminals 2219 to help prevent inadvertent contact between terminals 2219 and a user's hands by keeping the user's hands spaced apart from the terminals 2219 at least a minimum distance. In some embodiments, the minimum distance is greater than 1, 1.25, 1.5, 1.75, 2, 2.5, 3, 4, 5, or more inches.

In some embodiments, the exposed electrically conductive terminals 2219, which contact the patient, are adjustable. For example, a distance the conductive terminals 2219 extend from the insulative portions 2218 may be adjustable. In some embodiments, the distance conductive electrodes 2219 extend from the insulative portion 2218 is controlled by moving conductive electrodes 2219 with respect to insulative portion 2218, which is fixed with respect to handle portion 2214. In some embodiments, the distance conductive terminals 2219 extend from the insulative portion 2218 is controlled by moving insulative portion 2218 with respect to conductive terminals 2219, which are fixed with respect to handle portion 2214.

Additionally or alternatively, a distance between adjacent conductive terminals 2219 may be adjustable.

As shown, a handle portion of connector 2220 includes finger stop 2222, which is spaced apart from high-voltage conductive portion 2224 to help prevent inadvertent contact conductive portion 2224 and a user's hands.

Figure 23:
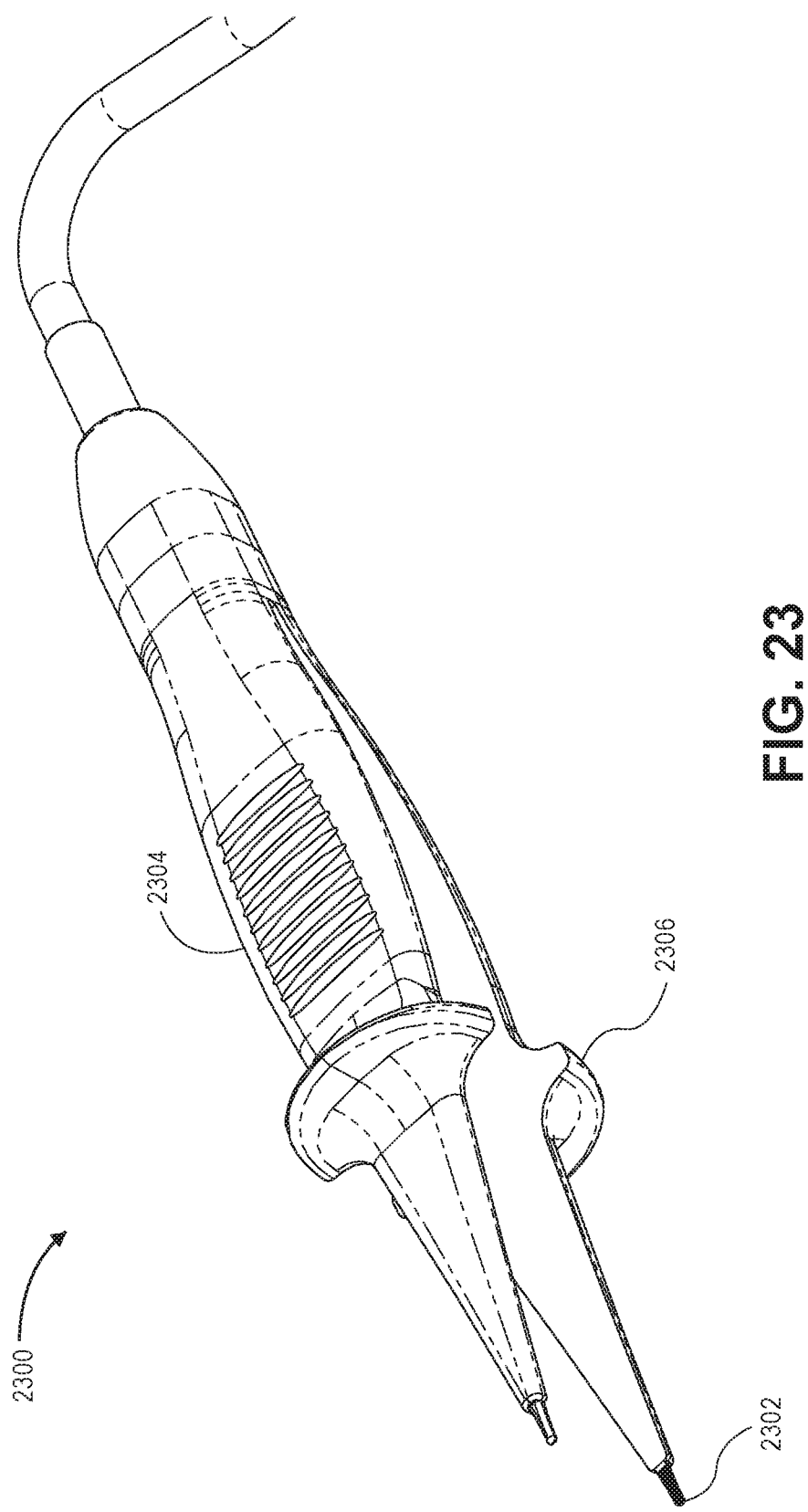
FIG. 23 is an illustration of an electrode which may be used in the nsPEF treatment systems discussed herein.

FIG. 23 is an illustration of an electrode 2300 which may be used in the nsPEF treatment systems discussed herein. For example, electrode 2300 may be used to treat a patient with nsPEF pulses. In this embodiment, electrically conductive terminals 2302 are spaced apart from one another by handle 2304, which is configured to apply a restorative force to terminals 2302 once displaced from a spaced apart neutral position. For example, handle 2304 may be configured to apply restorative force to terminals 2302 when terminals 2302 are spaced apart by a distance greater than or less than 1 mm, 2 mm, 3 mm, 4 mm, 5 mm, 7.5 mm, 1 cm, 1.5 cm, 2 cm, 2.5 cm, 3 cm, or another distance.

Handle 2304 includes handle feature 2306 to help prevent inadvertent contact between terminals 2302 and a user's hands.

Figure 24:
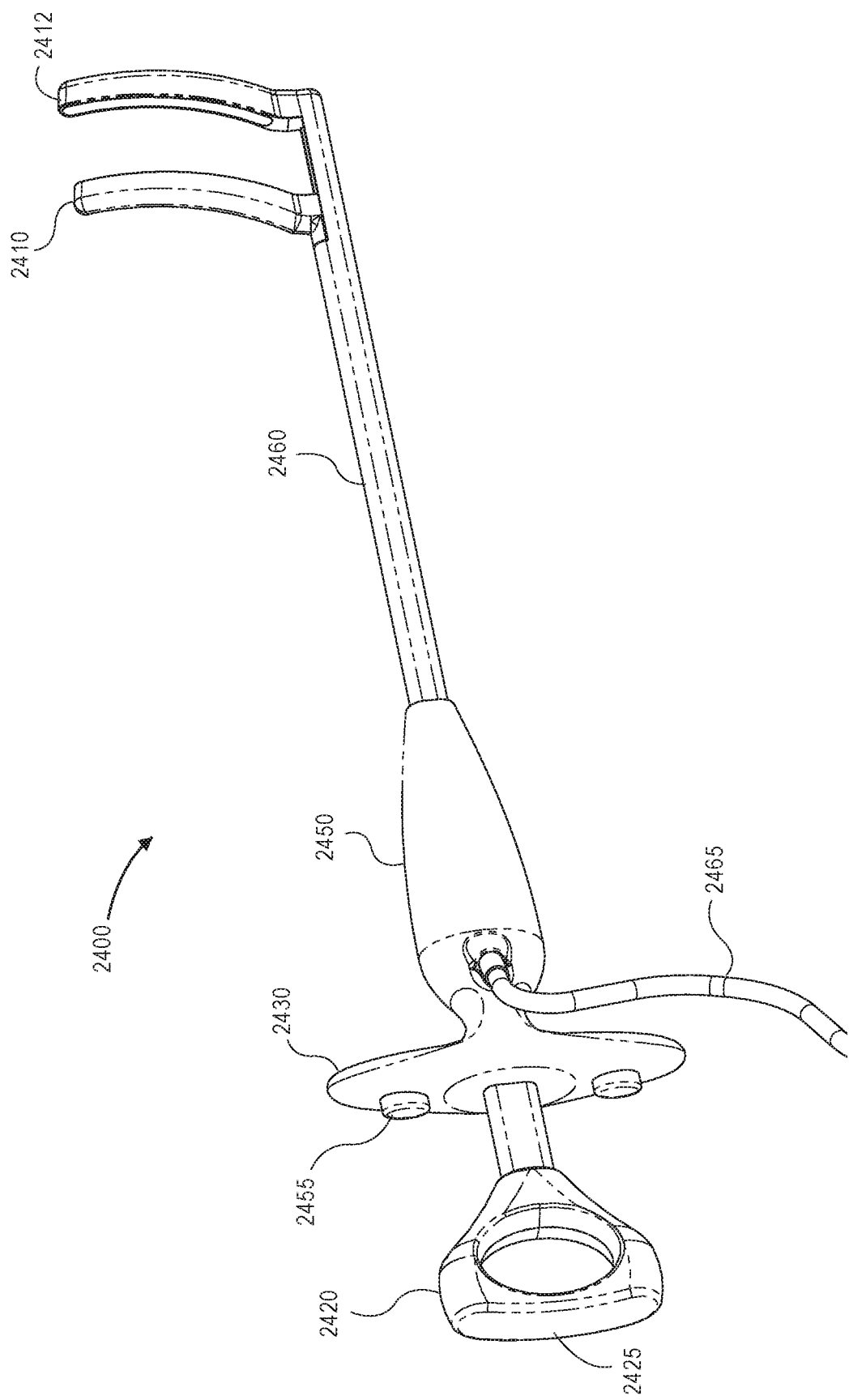
FIG. 24 is an illustration of an electrode which may be used in the nsPEF treatment systems discussed herein.

FIG. 24 is an illustration of an electrode 2400 which may be used in the nsPEF treatment systems discussed herein.

For example, electrode 2400 may be used to treat a patient suffering from atrial fibrillation. In this embodiment, electrically conductive terminals 2410 and 2412 are adjustably spaced apart from one another according to a relative distance between the thumb ring 2420 and finger grip 2430. In some embodiments, finger grip 2430 includes a ring configured to receive a finger of the user. Thumb ring 2420 includes ergonomic blunt surface 2425 for engaging a palm of the user.

Electrode 2400 includes housing 2450 connected to terminals 2410 and 2412 by shaft 2460. Housing 2450 includes a wiring channel to electrically connect terminals 2410 and 2412 with cable 2465. In some embodiments, housing 2450 includes an internal stop (not shown) configured to ensure a minimum distance between terminals 2410 and 2412. In some embodiments, housing 2450 includes a spring and ratchet mechanism configured to lock terminals 2410 and 2412 at a fixed distance. In such embodiments, housing 2450 also includes ratchet release button 2455 configured to selectively release terminals 2410 and 2412 from a locked position.

In some embodiments, terminal 2410 is configured to move with respect to housing 2450. In some embodiments, terminal 2412 is configured to additionally or alternatively move with respect to housing 2450.

In some embodiments, shaft 2460 and terminals 2410 and 2412 each include a conduit configured to conduct a substance to the distal ends of terminals 2410 and 2412. For example, an insulative gel may be extruded from the ends of terminals 2410 and 2412 through the conduits.

Figure 25:
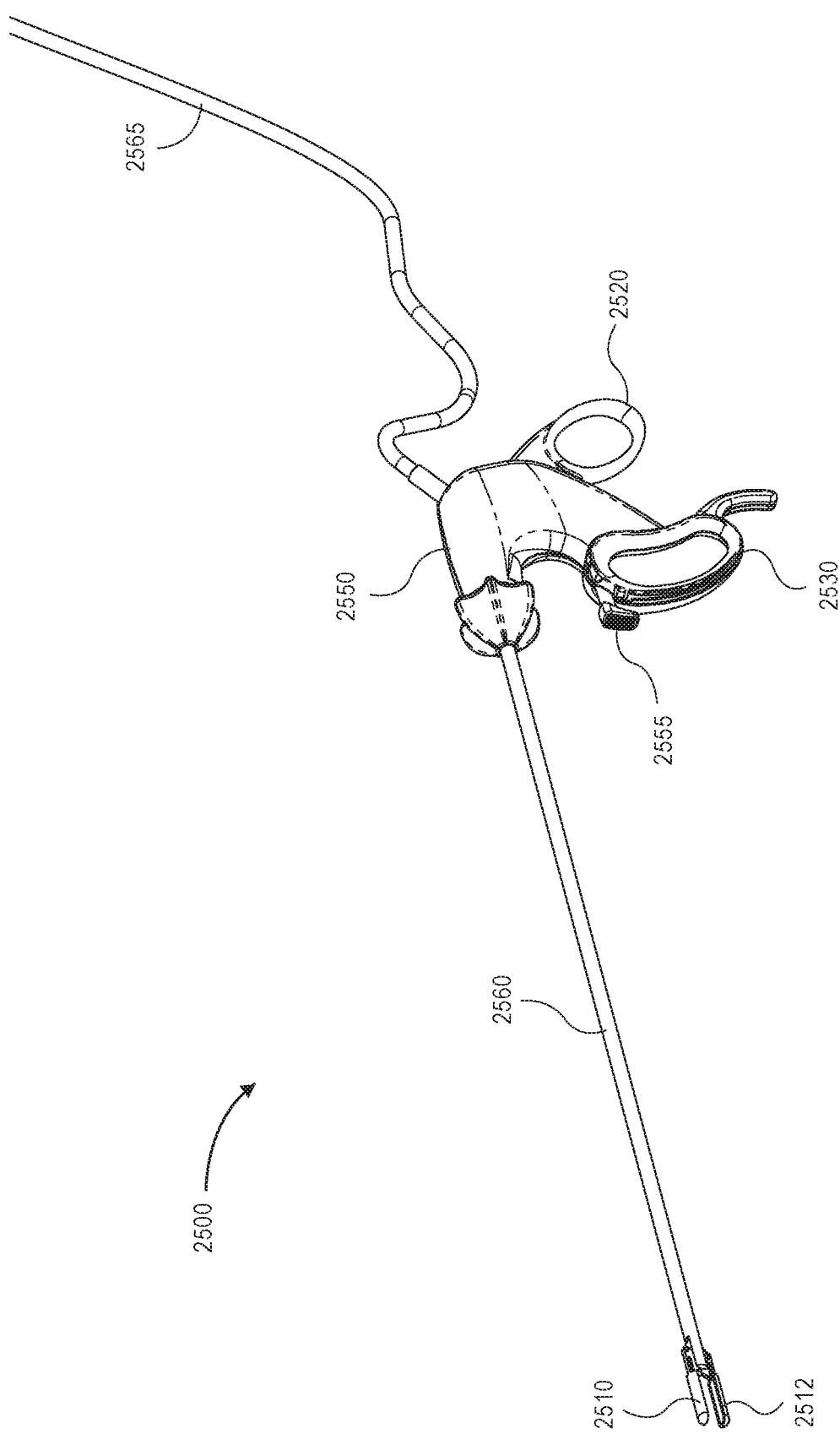
FIG. 25 is an illustration of an electrode which may be used in the nsPEF treatment systems discussed herein.

FIG. 25 is an illustration of an electrode 2500 which may be used in the nsPEF treatment systems discussed herein. For example, electrode 2500 may be used during a laproscopic procedure to treat a patient. In this embodiment, electrically conductive terminals 2510 and 2512 are adjustably spaced apart from one another according to a relative distance between the thumb ring 2520 and finger grip 2530.

Electrode 2500 includes housing 2550 connected to terminals 2510 and 2512 by shaft 2560. Housing 2550 includes a wiring channel to electrically connect terminals 2510 and 2512 with cable 2565. In some embodiments, housing 2550 includes an internal stop (not shown) configured to ensure a minimum distance between terminals 2510 and 2512. In some embodiments, housing 2550 includes a spring and ratchet mechanism configured to lock terminals 2510 and 2512 at a fixed distance. In such embodiments, housing 2550 also includes ratchet release button 2555 configured to selectively release terminals 2510 and 2512 from a locked position.

In some embodiments, terminal 2510 is configured to move or rotate with respect to shaft 2560. In some embodiments, terminal 2512 is configured to additionally or alternatively move or rotate with respect to shaft 2560. In some embodiments, terminals 2510 and 2512 are configured to move with respect to shaft 2560 and with respect to each other such that terminals 2510 and 2512 remain substantially parallel.

Figure 26:
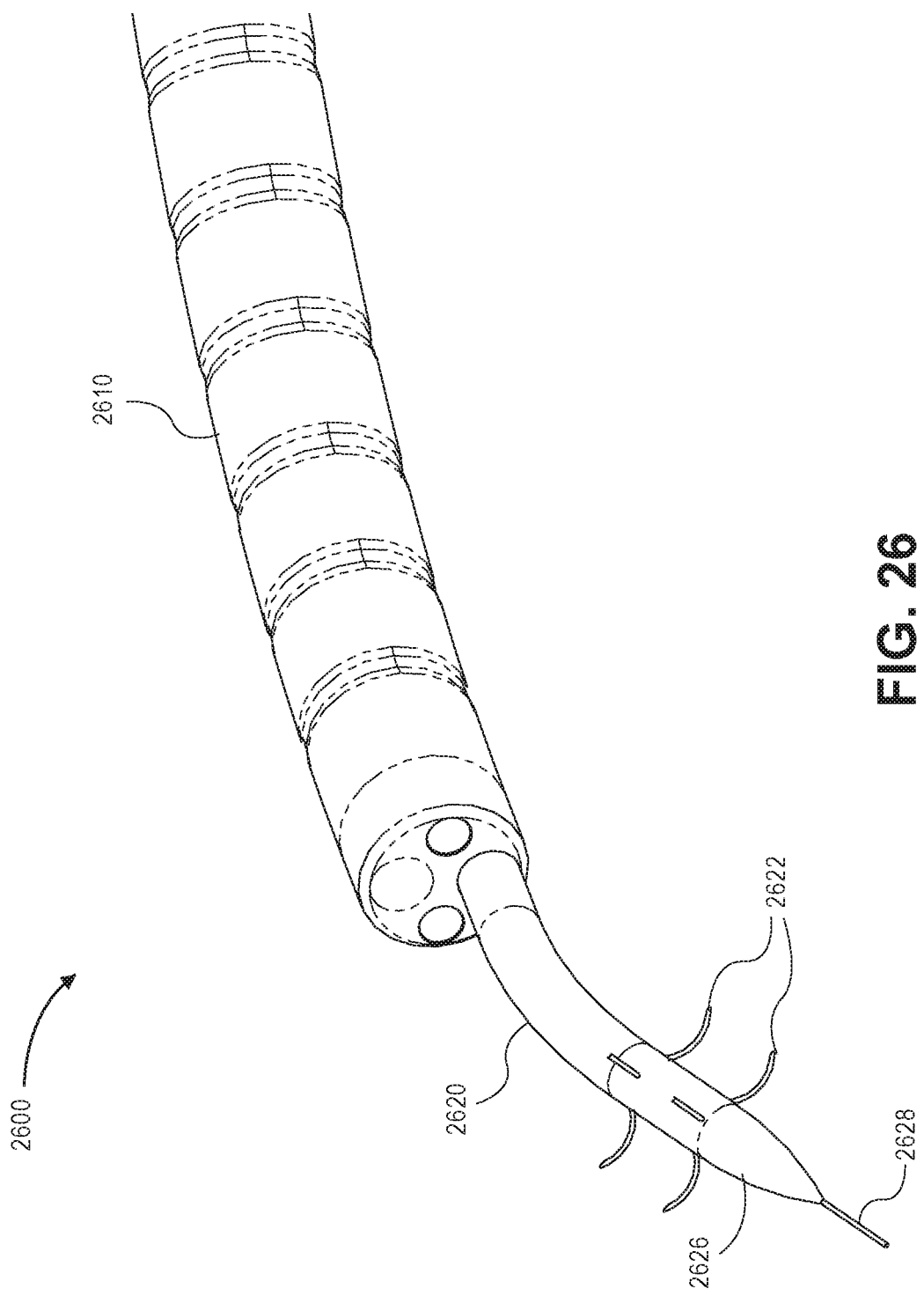
FIG. 26 is an illustration of an instrument which may be used in the nsPEF treatment systems discussed herein.

FIG. 26 is an illustration of instrument 2600 which may be used in the nsPEF treatment systems discussed herein. For example, instrument 2600 may be used, for example, as a catheter to contact the patent with terminals percutaneously or endoluminally during treatment. In this embodiment, electrode 2620 is connected to endoscope 2610. For example, electrode 2620 may be routed through a lumen in the endoscope 2610.

Electrode 2620 includes insulative portion 2626 and positive and negative electrically conductive terminals 2622. In some embodiments, electrode 2620 also includes needle 2628 to help electrode 2620 penetrate through tissue.

Any of the electrodes discussed with reference to FIGS. 22-26 may include a thermocouple thermally connected to either of its terminals.

FIGS. 27A and 27B are illustrations of a connector 2700 configured to be mated with a housing cutaway portion 2750. Connector 2700 may, for example, be used in nsPEF system 100 to connect electrode 102 to housing 105. When mated, connector 2700 electrically connects electrode 102 with the electronic components internal to housing 105, such as an nsPEF pulse generator. FIG. 27A illustrates connector 2700 and cutaway portion 2750 in an unmated position. FIG. 27B illustrates connector 2700 and cutaway portion 2750 in a mated position.

Connector 2700 includes a hole 2702 configured to receive a cable electrically contacting an electrode. Connector 2700 also includes a handle 2706 which includes internal conductors which electrically connect terminals 2704 with the cable. Handle 2706 also includes standoff skirt 2708, which is configured to provide a minimum distance along the outer surface of connector 2700 between a user's hand holding the connector 2700 by the handle 2706 and terminals 2704. In some embodiments, standoff skirt 2708 provides at least 1 inch of such distance. In some embodiments, the minimum distance is greater than 1, 1.25, 1.5, 1.75, 2, 2.5, 3, 4, 5, or more inches.

As shown, terminals 2704 are spaced apart from handle 2706 by spacers 2710, for example, by a distance greater than 1 inch.

As shown, housing cutaway portion 2750 includes terminal receptacle holes 2752, which are configured to receive terminals 2704 of connector 2700 when connector 2700 is mated with housing cutaway portion 2750. In this embodiment, housing cutaway portion 2750 also includes skirt receptacle holes 2754, which is configured to receive standoff skirt 2708 of connector 2700 when connector 2700 is mated with housing cutaway portion 2750.

To increase the distance of a shortest path along the surface of connector 2700 between electrically terminals 2704 and the user's hand, in this embodiment, standoff skirt 2708 includes two concentric ring portions. In addition, housing cutaway portion 2750 includes two skirt receptacle holes 2754. In alternative embodiments, a connector has more than two concentric ring portions and a corresponding housing cutaway portion has more than two skirt receptacle holes.

Figure 28A:
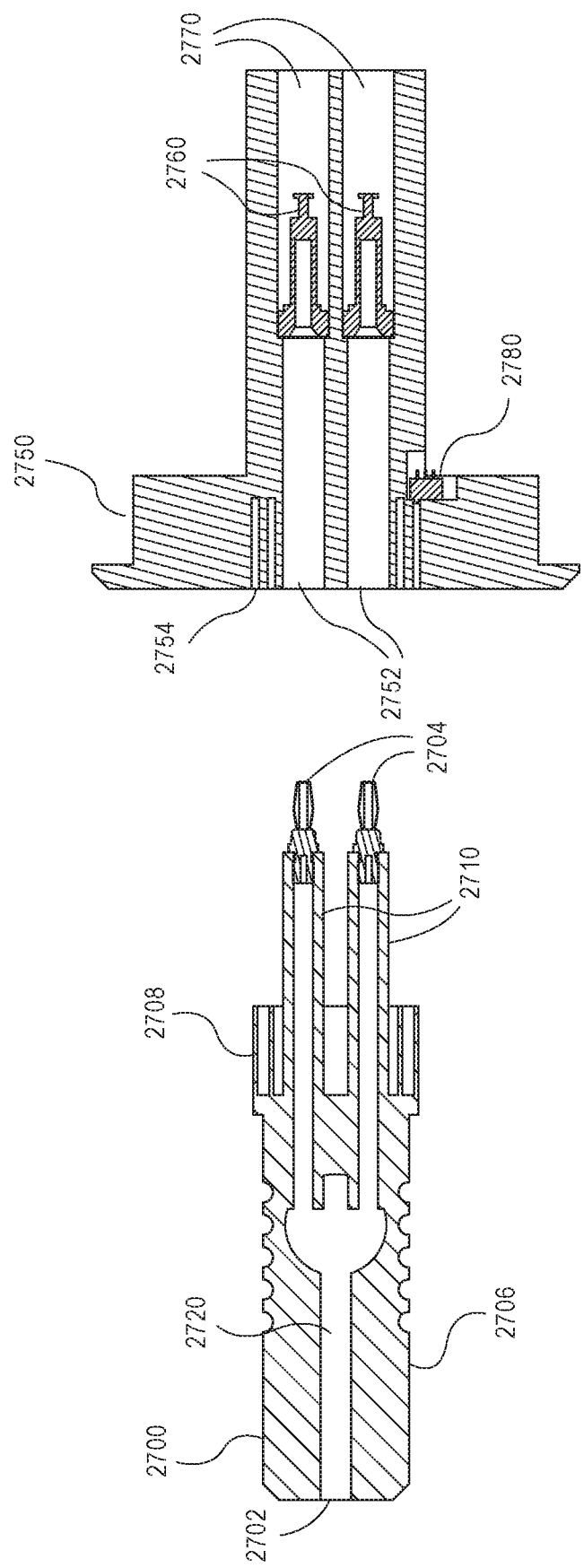
FIG. 28A is an illustration of a cross-sectional view of a connector and a housing cutaway portion.
Figure 28B:
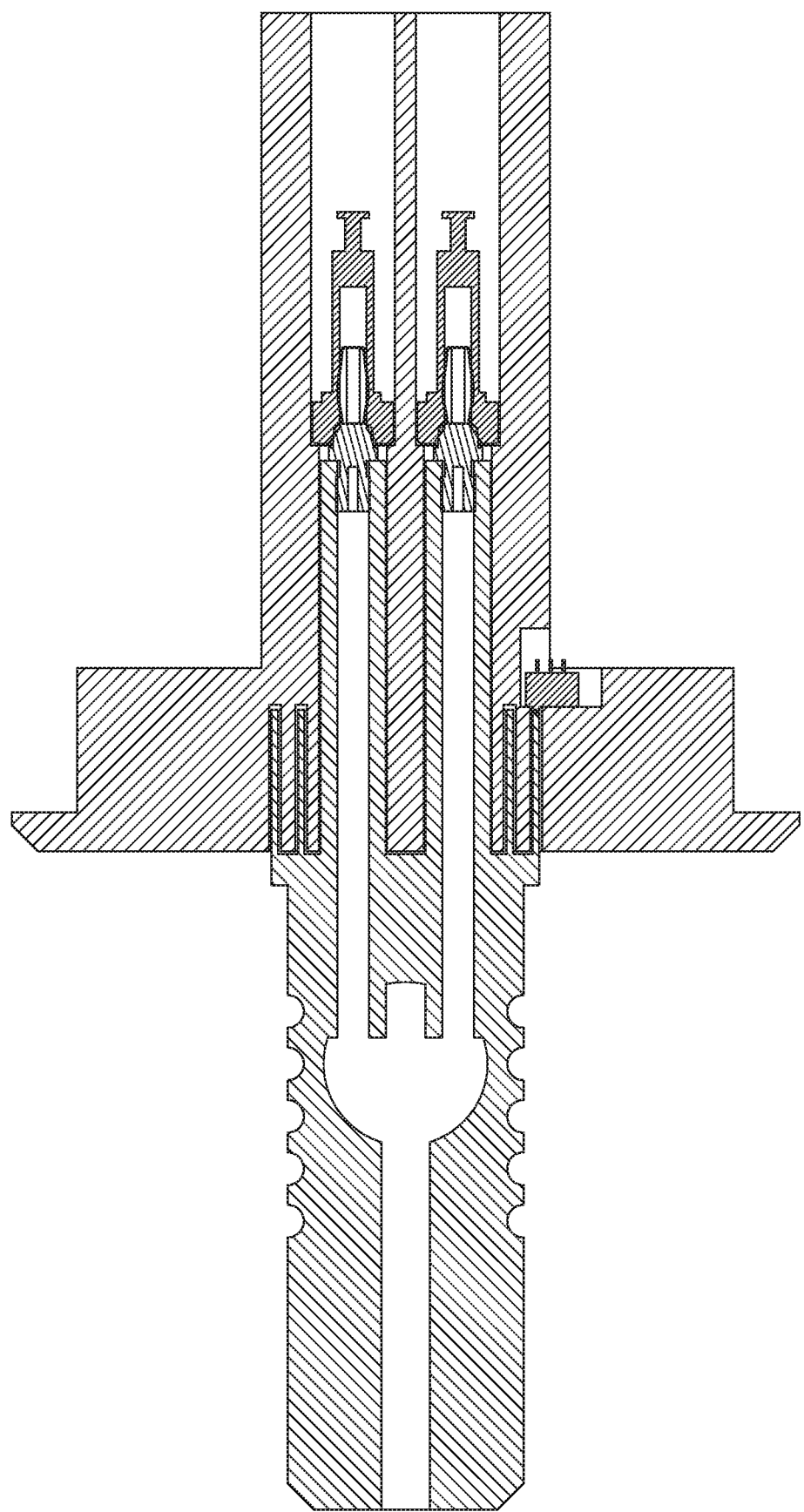
FIG. 28B is an illustration of a cross-sectional view of a connector and a housing cutaway portion.
Figure 28C:
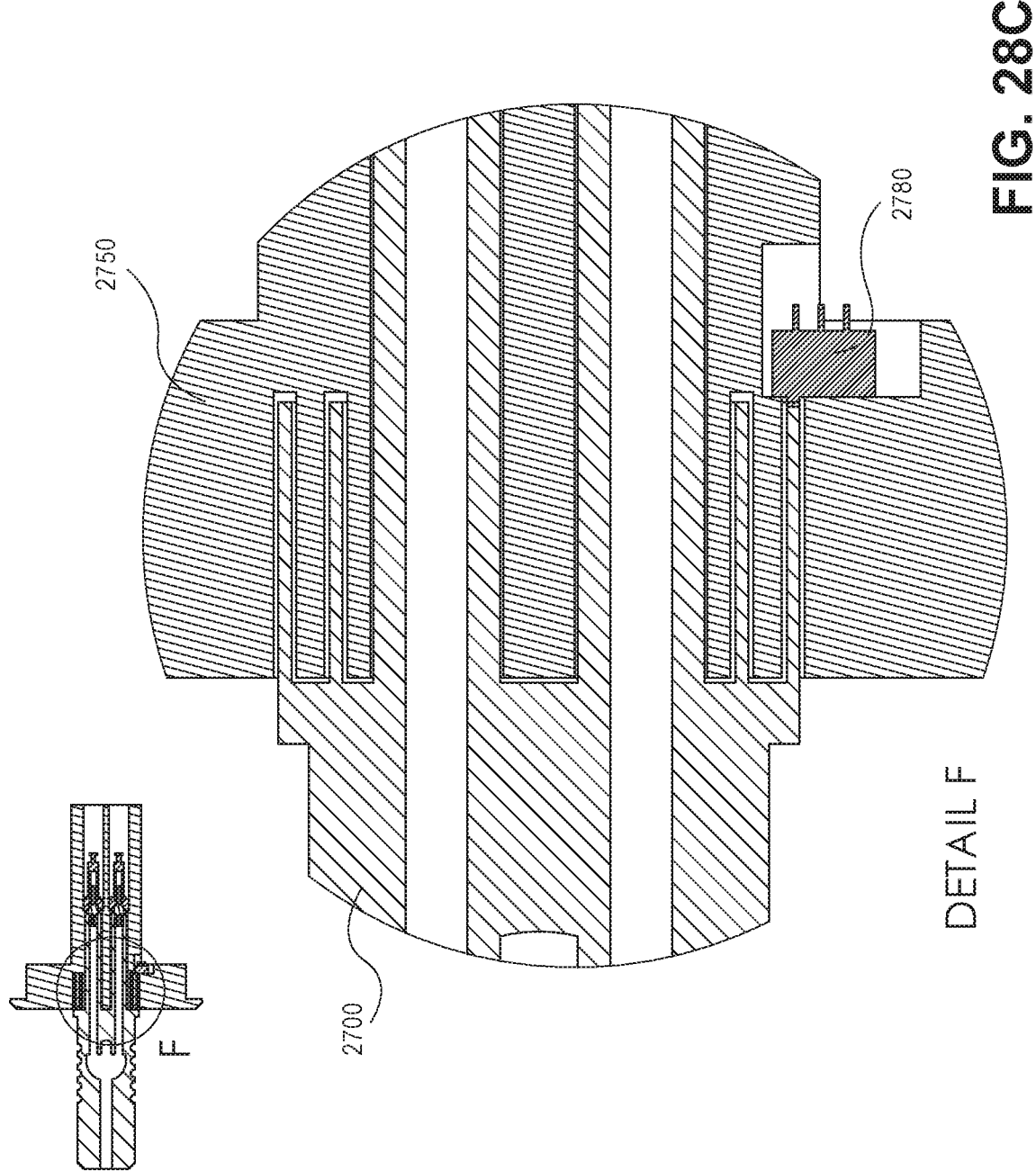
FIG. 28C is an illustration of a cross-sectional view of a connector and a housing cutaway portion.

FIGS. 28A, 28B, and 28C are illustrations of a cross-sectional view of connector 2700 and housing cutaway portion 2750. The plane of the cross-sectional view is defined by the axis of the terminal receptacle holes 2752 illustrated in FIG. 27A. FIG. 28A illustrates connector 2700 and cutaway portion 2750 in an unmated position. FIGS. 28B and 28C illustrate connector 2700 and cutaway portion 2750 in a mated position, where FIG. 28C illustrates a detailed view of portions of connector 2700 and cutaway portion 2750.

As shown in FIG. 28A, connector 2700 includes cavity 2720 configured to include wiring (not shown) which electrically connects the cable with terminals 2704. Cavity 2720 may also include wiring to connect to one or more thermocouples connected to one or more of the terminals of the electrode.

Housing cutaway portion 2750 includes terminals 2760 which are configured to receive terminals 2704 when connector 2700 and housing cutaway portion 2750 are in the mated position. Terminals 2760 are shielded from or are spaced a minimum distance apart from external portions of the housing which may be accessed by a hand or a finger of a user. The minimum distance may be determined based at least in part on an expected voltage applied to terminals 2760 to ensure that the voltage is insufficient to cause a shock to a hand or finger of the user if placed the minimum distance from the terminals 2760. In some embodiments, the minimum distance is greater than 1, 1.25, 1.5, 1.75, 2, 2.5, 3, 4, 5, or more inches.

Cutaway portion 2750 also includes cavities 2770 which are configured to include wiring (not shown) which electrically connects terminals 2760 with the electronic components internal to the housing. As a result, when in the mated position, the electronic components internal to the housing are electrically connected with a therapeutic electrode via terminals 2760, terminals 2704, wiring between terminals 2704 and a cable, and the cable, which is electrically connected to the therapeutic electrode.

Housing cutaway portion 2750 also illustrates electromechanical switch 2780. As a result of connector 2700 and housing cutaway portion 2750 being in the mated position, electromechanical switch 2780 assumes a conductive state indicating that the connector 2700 and the housing cutaway portion 2750 are mated. In addition, as a result of connector 2700 and housing cutaway portion 2750 being in an unmaintained position, electromechanical switch 2780 assumes a conductive state indicating that the connector 2700 and the housing cutaway portion 2750 are unmated. Electromechanical switch 2780 may be connected to a controller (not shown) which may be configured to prevent electronic components internal to the housing from applying electrical signals to terminals 2760 as a result of connector 2700 and housing cutaway portion 2750 being unmated, or may be configured to allow electronic components internal to the housing to apply electrical signals to terminals 2760 as a result of connector 2700 and housing cutaway portion 2750 being mated.

In some embodiments, electromechanical switch 2780 includes circuitry configured to interface with the controller. For example, the controller may identify the connector 2700 or an electrode connected to the connector 2700 as a result of the controller receiving identifying information from the circuitry. In some embodiments, the circuitry may be configured to count and store the number of nsPEF pulses delivered through the connector 2700.

Figure 29:
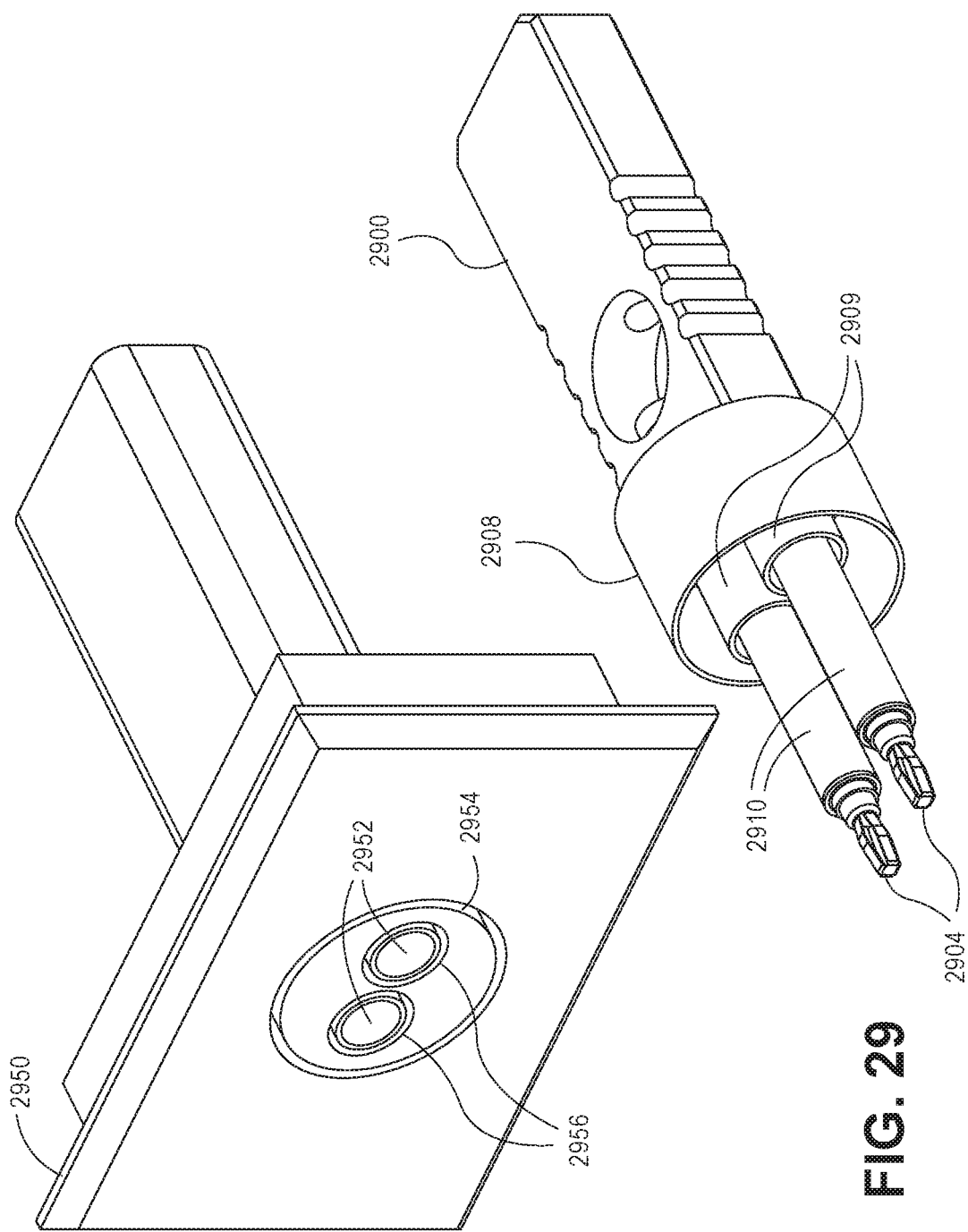
FIG. 29 is an illustration of a connector configured to be mated with a housing cutaway portion.

FIG. 29 is an illustration of connector 2900 configured to be mated with housing cutaway portion 2950. Connector 2900 may, for example, be used in nsPEF system 100 to connect electrode 102 to housing 105. When mated, connector 2900 electrically connects electrode 102 with the electronic components internal to housing 105, such as an nsPEF pulse generator. FIG. 29 illustrates connector 2900 and cutaway portion 2950 in an unmated position.

Connector 2900 includes features similar to or identical to connector 2700 illustrated above in FIGS. 27A, 27B, 28A, 28B, and 28C.

Connector 2900 includes standoff skirt 2908, which is similar to standoff skirt 2708 of connector 2700. In addition, connector 2900 includes additional standoff skirts 2909. As shown, standoff skirts 2909 each surround a portion of one of the spacers 2910. Standoff skirts 2909 maintain a desired separation between terminals 2904.

Housing cutaway portion 2950 includes features similar to or identical to housing cutaway portion 2750 illustrated above in it FIGS. 27A, 27B, 28A, 28B, and 28C.

In this embodiment, in addition to terminal receptacle holes 2952 and skirt receptacle hole 2954, housing cutaway portion 2950 also includes skirt receptacle holes 2956, which are configured to receive skirts 2909 of connector 2900 when connector 2900 is mated with housing cutaway portion 2950.

Figure 30A:
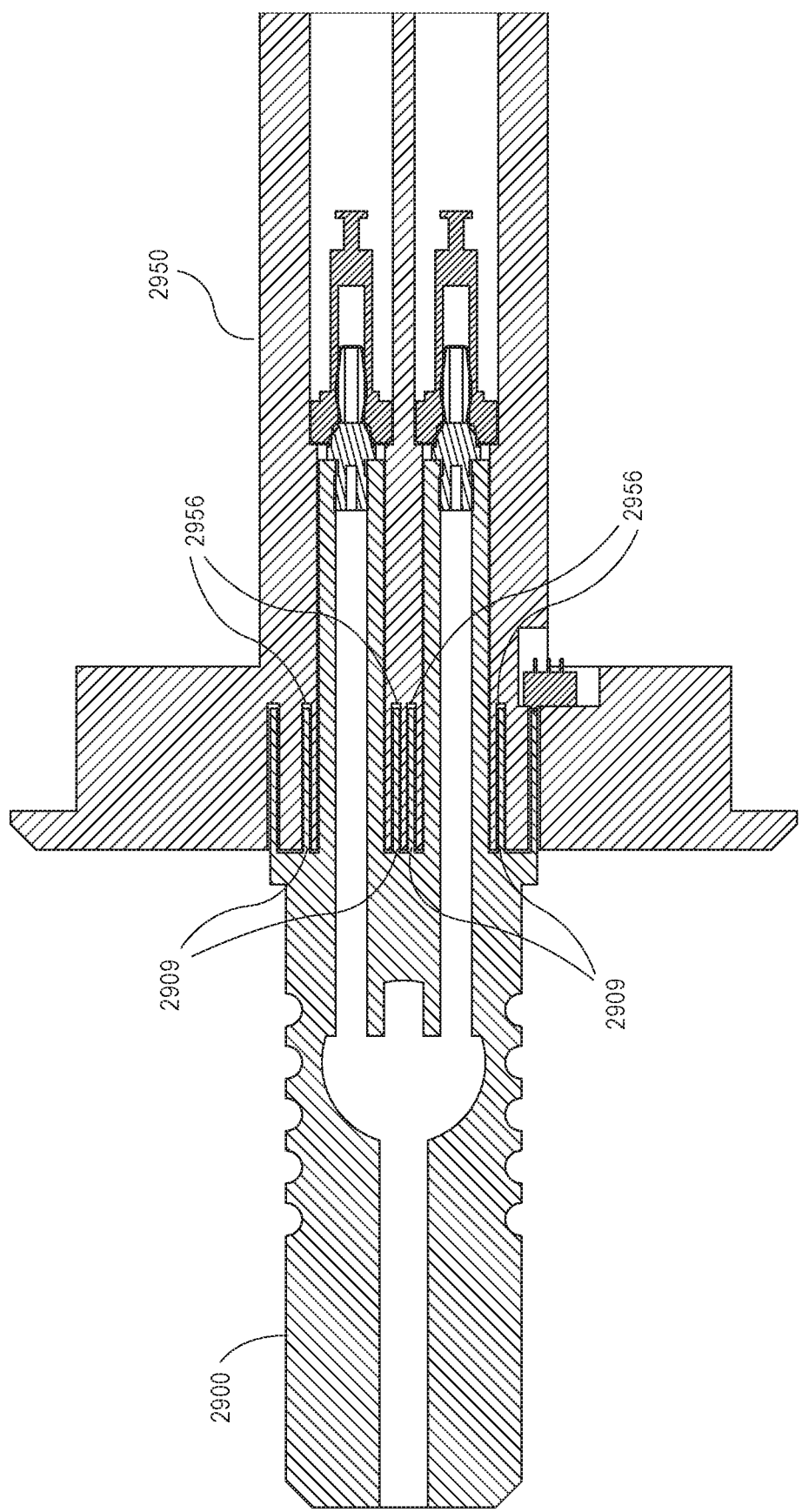
FIG. 30A is an illustration of a cross-sectional view of a connector and a housing cutaway portion.
Figure 30B:
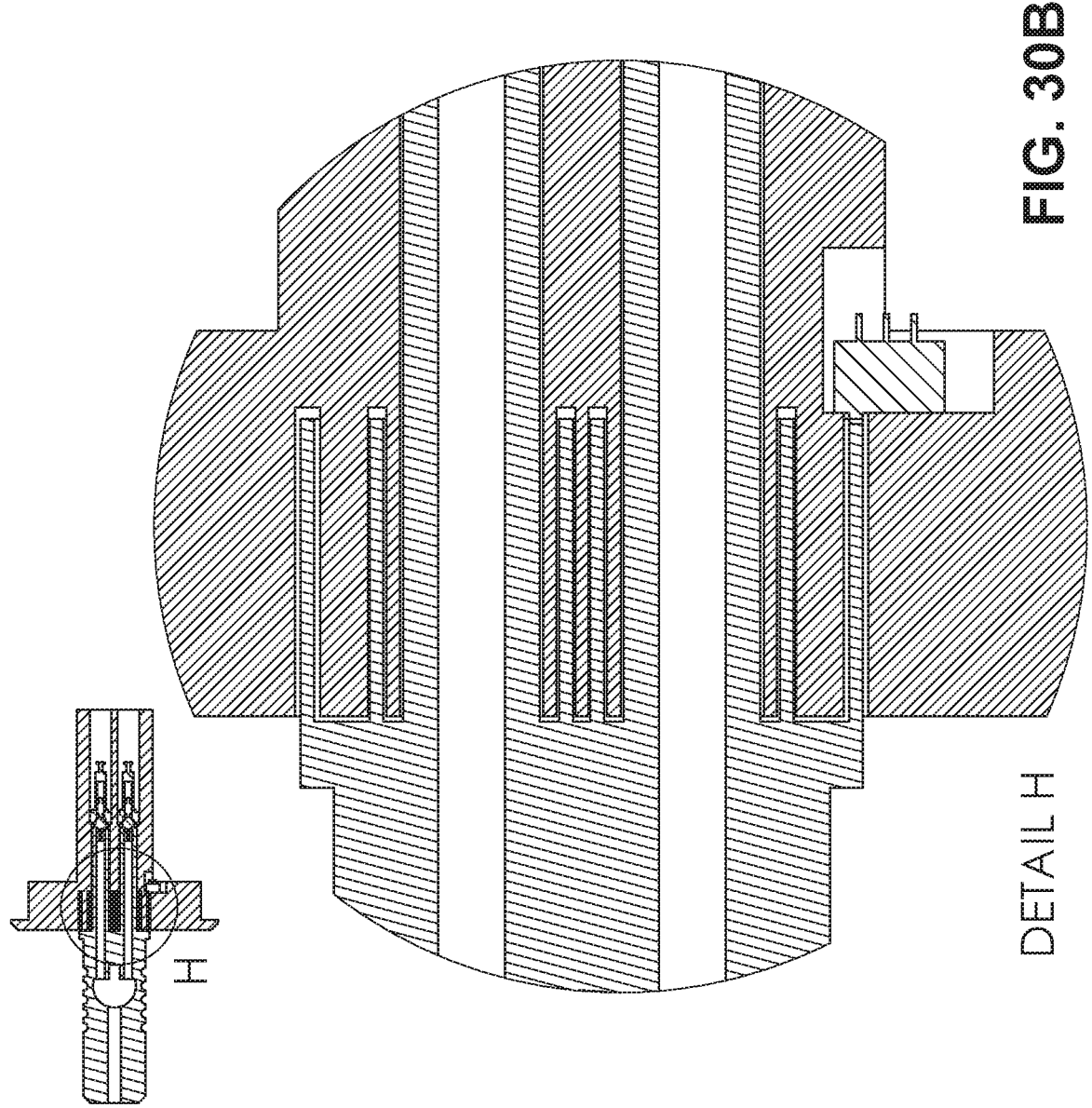
FIG. 30B is an illustration of a cross-sectional view of a connector and a housing cutaway portion.

FIGS. 30A and 30B are illustrations of a cross-sectional view of connector 2900 and housing cutaway portion 2950. FIGS. 30A and 30B illustrate connector 2900 and cutaway portion 2950 in a mated position, where FIG. 30B illustrates a detailed view of portions of connector 2900 and cutaway portion 2950.

In some embodiments, an nsPEF pulse generator may be connected with a cable to a therapeutic electrode, where the therapeutic electrode has terminals which are electrically connected to the cable by a connector/receptacle mating having characteristics similar or identical to one or more of connector 2700 and housing cutaway portion 2750 and connector 2900 and housing cutaway portion 2950.

Figure 31A:
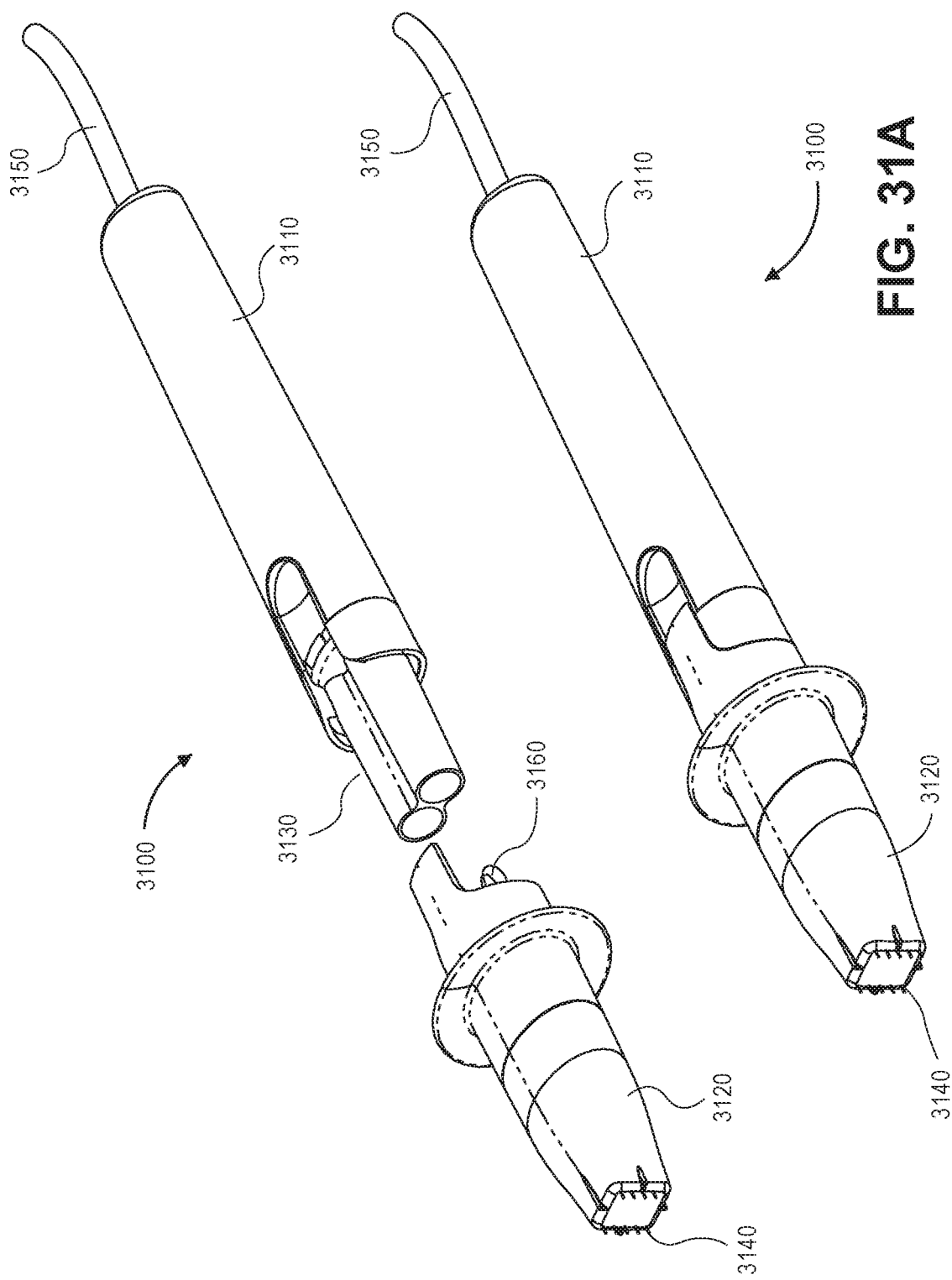
FIG. 31A illustrate an embodiment of an electrode.
Figure 31B:
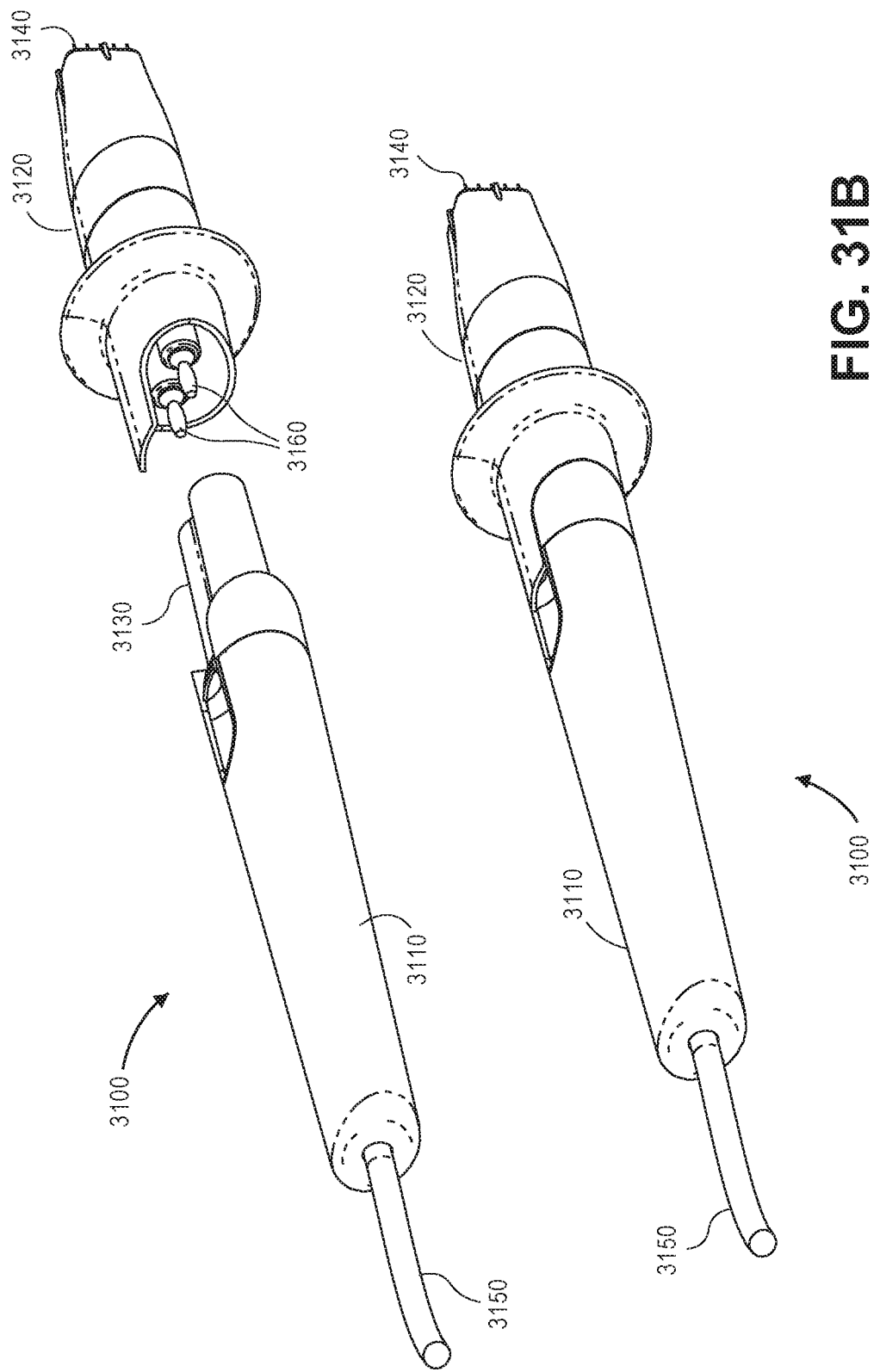
FIG. 31B illustrate an embodiment of an electrode.

For example, FIGS. 31A and 31B illustrate an electrode 3100 which has therapeutic terminals 3140 which are connected to cable 3150 through conductors which run through handle 3110 and tip 3120. Electrode 3100 may be used in the nsPEF treatment systems discussed herein. For example, cable 3150 may be connected to an nsPEF pulse generator by a connector (not shown) having features similar or identical to those of the connectors discussed elsewhere herein.

As shown, tip 3120 is removably connectable to handle 3110. To connect tip 3122 handle 3110, connection terminals 3160 are inserted into skirt 3130. In some embodiments, tip 3120 is disposable, or may be discarded or disposed of after a single use.

Figure 32A:
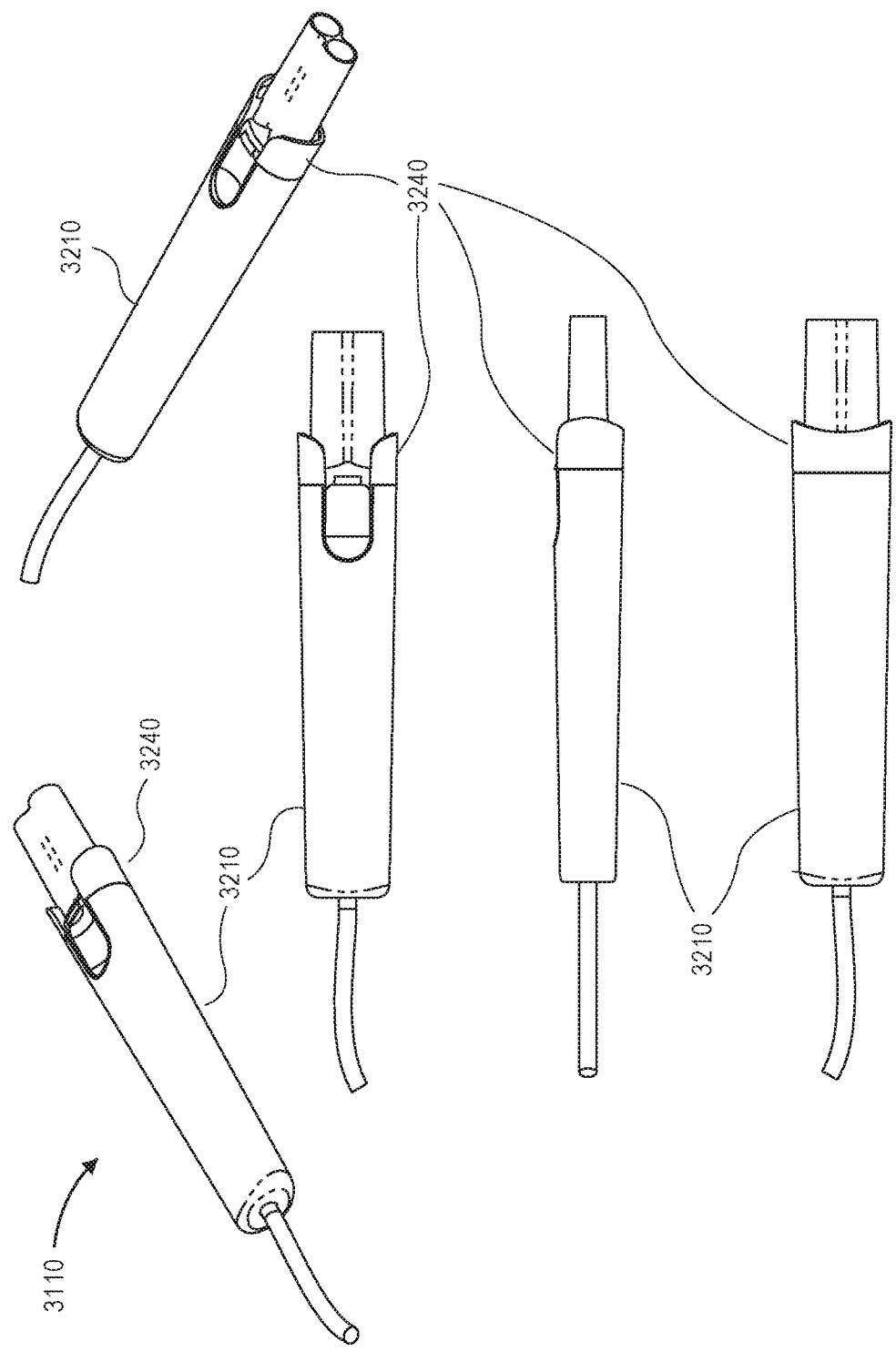
FIG. 32A illustrates an embodiment of a handle.
Figure 32B:
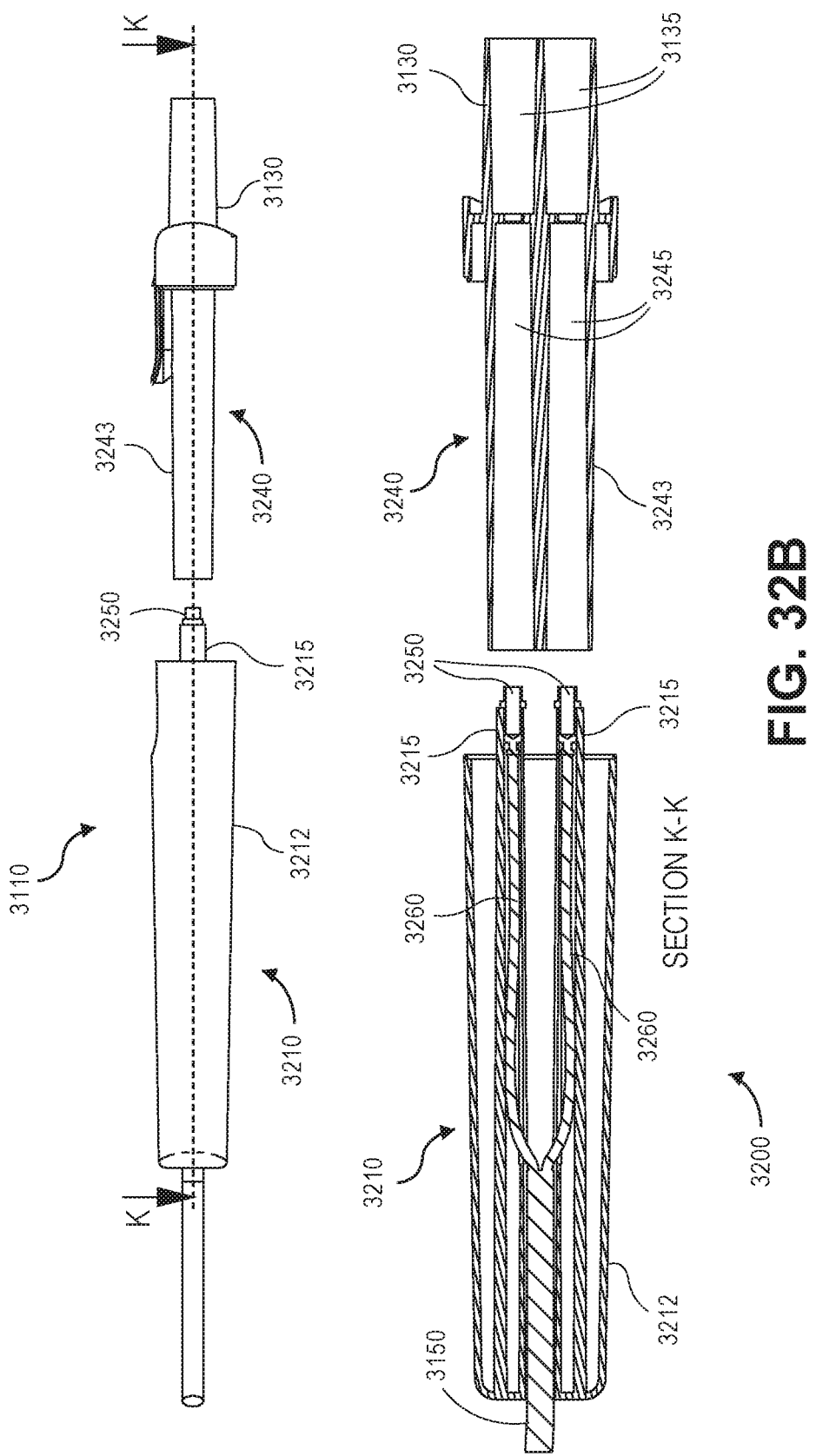
FIG. 32B illustrates an embodiment of a handle.

FIGS. 32A, 32B, and 32C illustrate handle 3110, which includes handle base 3210 and handle cap 3240. As shown in FIG. 32B, cable 3150 extends into handle base 3210. First and second wires 3260 split from cable 3150, and respectively extend through handle base 3210 within the first and second wire bosses 3215. Each of the first and second wires 3260 is connected, for example using a solder connection, with one of first and second connectors 3250 which extend from the first and second wire bosses 3215.

First and second connectors 3250 are configured to receive connection terminals 3160 from tip 3120. When tip 3120 is connected with handle 3110, connection terminals 3160 extend into first and second connectors 3250, causing a mechanical and an electrical connection to be made between connection terminals 3160 and cable 3150.

Because the voltage between connectors 3250 can be very large, leakage may occur between connectors 3250 along a path on a surface or combination of connected surfaces between connectors 3250. In some embodiments, first and second wires 3260 are surrounded by insulation. In such embodiments, at least to prevent or minimize the leakage, the distance between connectors 3250 along any path on any surface or combination of surfaces is greater than a minimum distance. In some embodiments, the minimum distance is greater than 1, 1.25, 1.5, 1.75, 2, 2.5, 3, 4, 5, or more inches.

In some embodiments, one of the first and second wires 3260 is covered by insulation, and the other of the first and second wires 3260 is not covered by insulation. In such embodiments, at least to prevent or minimize the leakage, the distance between the connector 3250 of the wire surrounded by insulation and the nearest portion of the wire without insulation along any path on any surface or combination of surfaces is greater than a minimum distance. In some embodiments, the minimum distance is greater than 1, 1.25, 1.5, 1.75, 2, 2.5, 3, 4, 5, or more inches.

As shown in FIG. 32B, handle cap 3240 includes skirt 3243, which has connector channels 3245. In addition, handle 3240 includes skirt 3130 which includes terminal channels 3135.

When the handle 3110 is assembled, as shown in FIG. 32C, first and second wires 3260 within the first and second wire bosses 3215 and first and second connectors 3250 extend through connector channels 3245 of handle cap 3240. In addition, as shown in FIG. 32C, when the handle 3110 is assembled, connectors 3250 are exposed through terminal channels 3135, such that when the handle 3110 is connected with tip 3120, the connection terminals of 3160 of the tip 3120 mechanically and electrically connect to connectors 3250.

In this embodiment, female connectors 3250 receive male connection terminals 3160. In alternative embodiments, female connection terminals 3160 receive male connectors 3250.

Figure 33A:
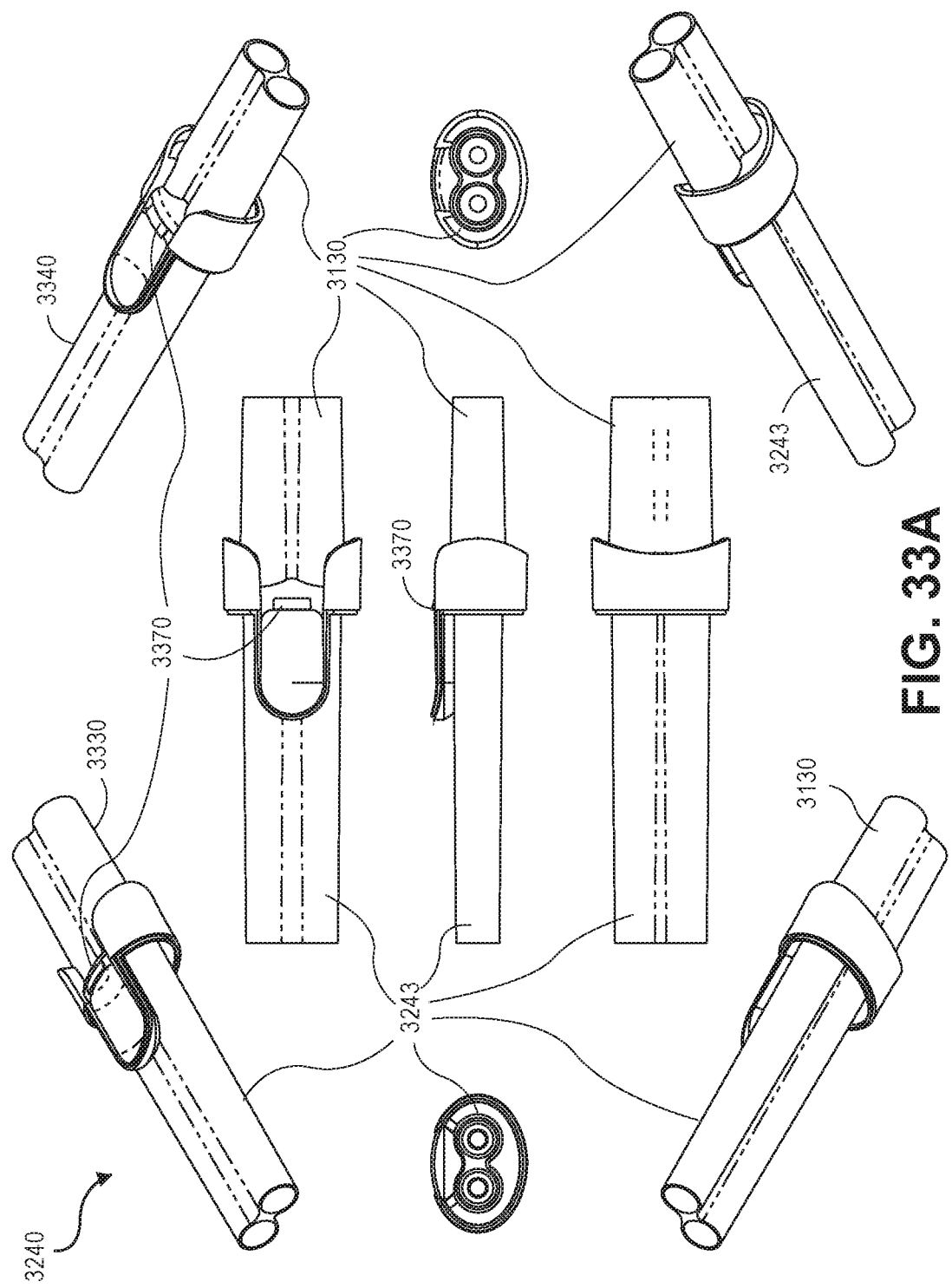
FIG. 33A illustrates an embodiment of a handle cap.
Figure 33B:
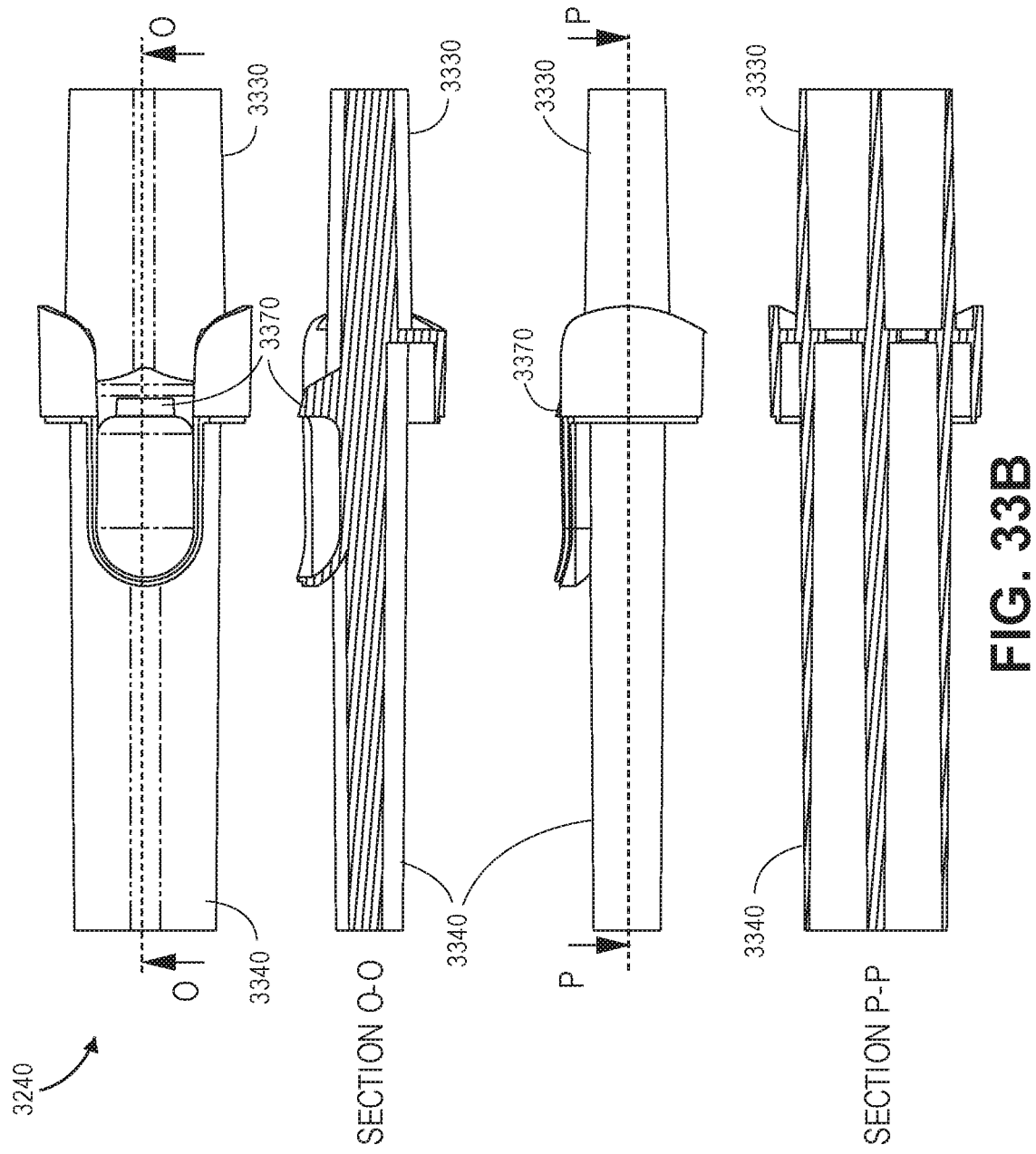
FIG. 33B illustrates an embodiment of a handle cap.

FIGS. 33A and 33B illustrate handle cap 3240. As shown, handle cap 3240 includes latch hook 3370. Latch hook 3370 is used to secure tip 3120 to handle 3110. The connection of tip 3120 and handle 3110 is discussed in further detail below.

Figure 34A:
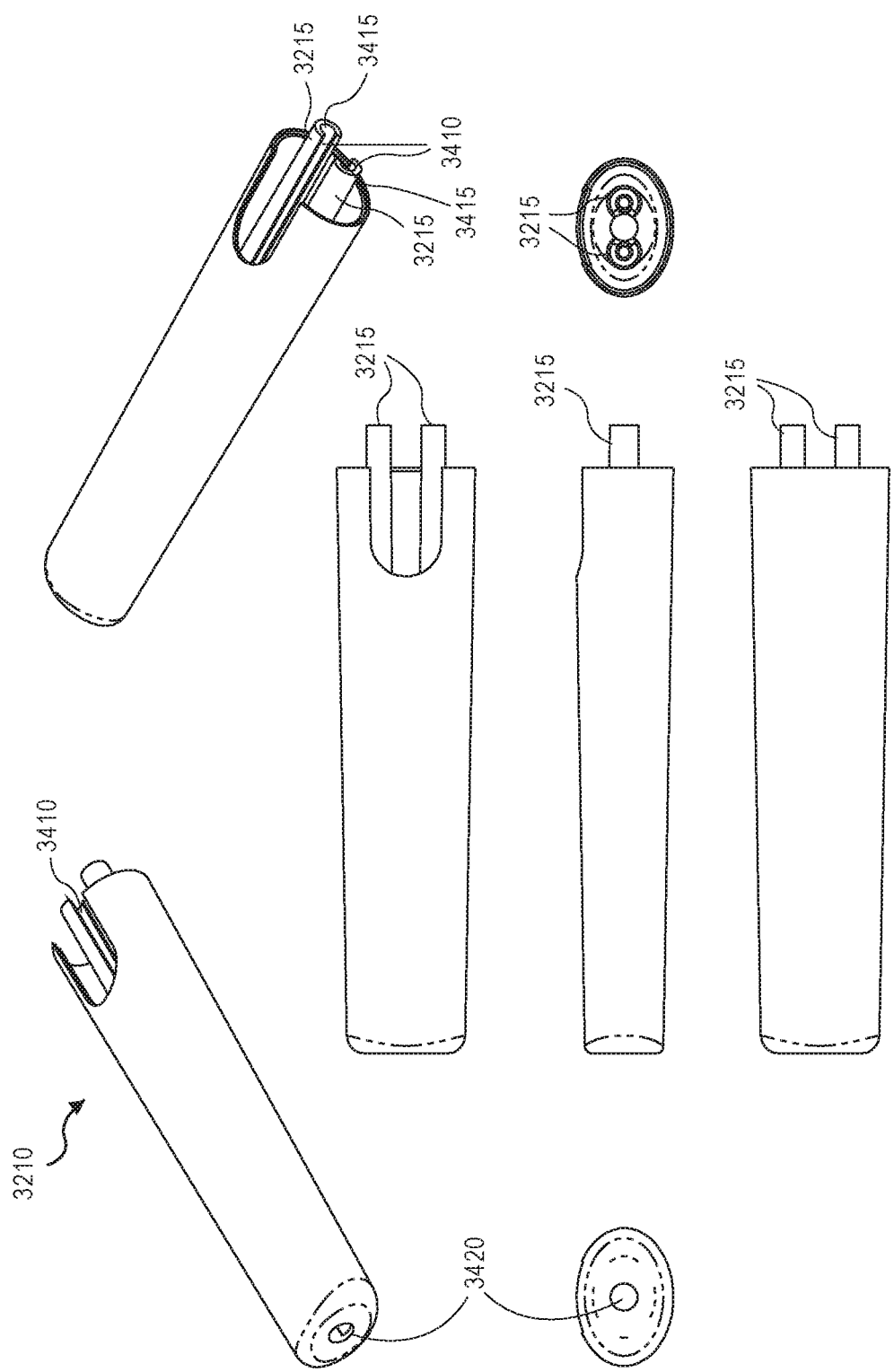
FIG. 34A illustrates an embodiment of a handle base.
Figure 34B:
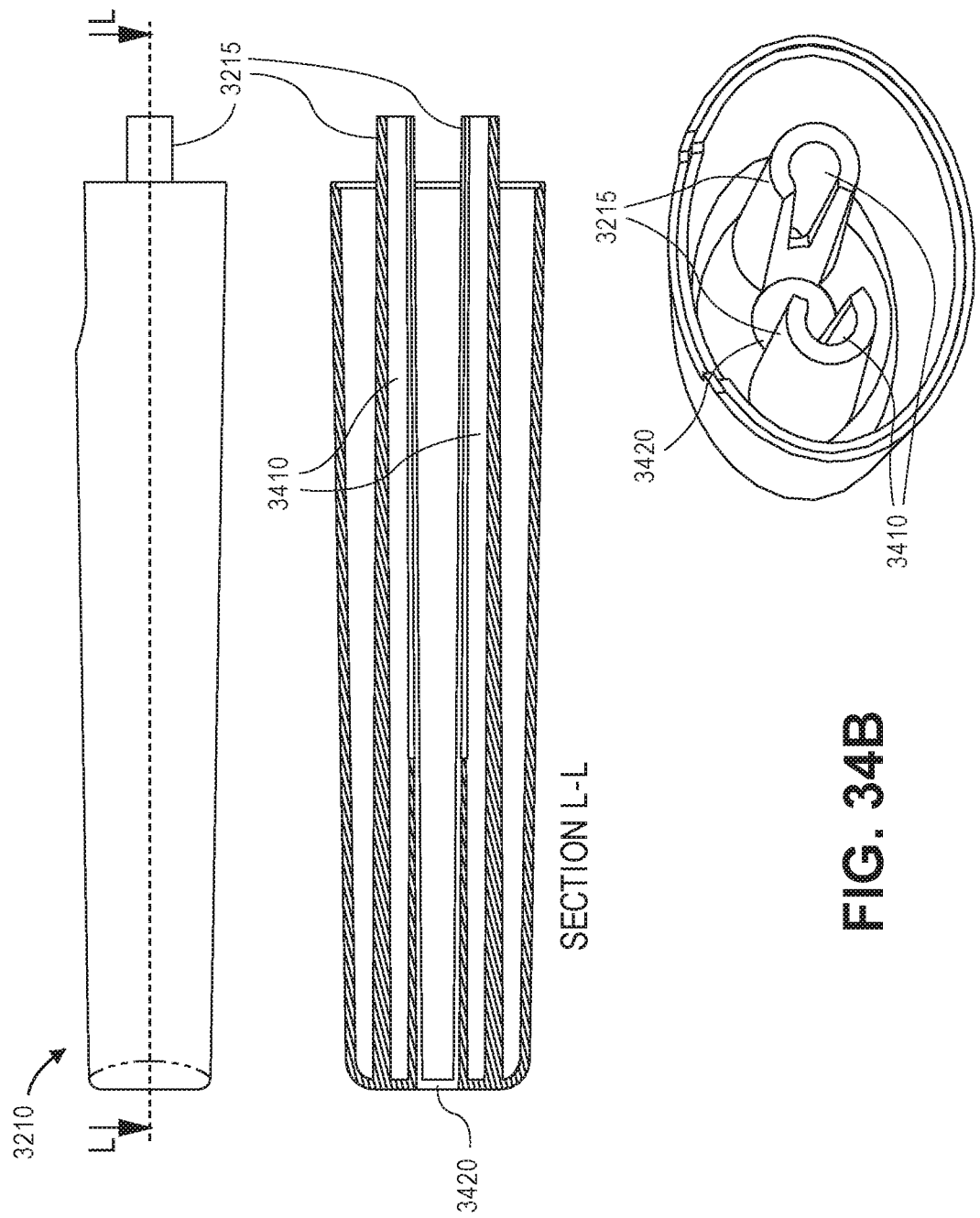
FIG. 34B illustrates an embodiment of a handle base.

FIGS. 34A and 34B illustrate handle base 3210. As shown, handle base 3210 includes wire bosses 3215. Wire bosses 3215 are generally tubular with the inner portion of the tubes each forming a wire channel 3410. The wire channels 3410 have openings 3415 at their ends which extend from handle base 3210 and are also open at slots extending along central portions or sides of the wire bosses 3215. Wire channels 3410 are particularly useful during assembly of handle 3110.

For example, during assembly a cable 3150 may be inserted into handle base 3210 through the hole 3420. See FIGS. 32B and 34B. The cable 3150 may be fed so as to extend beyond wire bosses 3215. Insulation may be stripped from cable 3150 so as to expose wires 3260. Connectors 3250 may be connected, for example by soldering, to wires 3260. The cable 3150 may be retracted from handle base 3210 such that connectors 3250 may be inserted into openings 3415 of wire bosses 3215. In addition, wires 3260 may be run through wire channels 3410 of wire bosses 3215. In some embodiments, one or more of the cable 3150, the wires 3260, and connectors 3250 may be cemented in place, for example, with epoxy. In some embodiments, as part of the assembly process for handle 3110, handle base 3210 is cemented to handle cap 3240, for example, with epoxy.

Figure 35A:
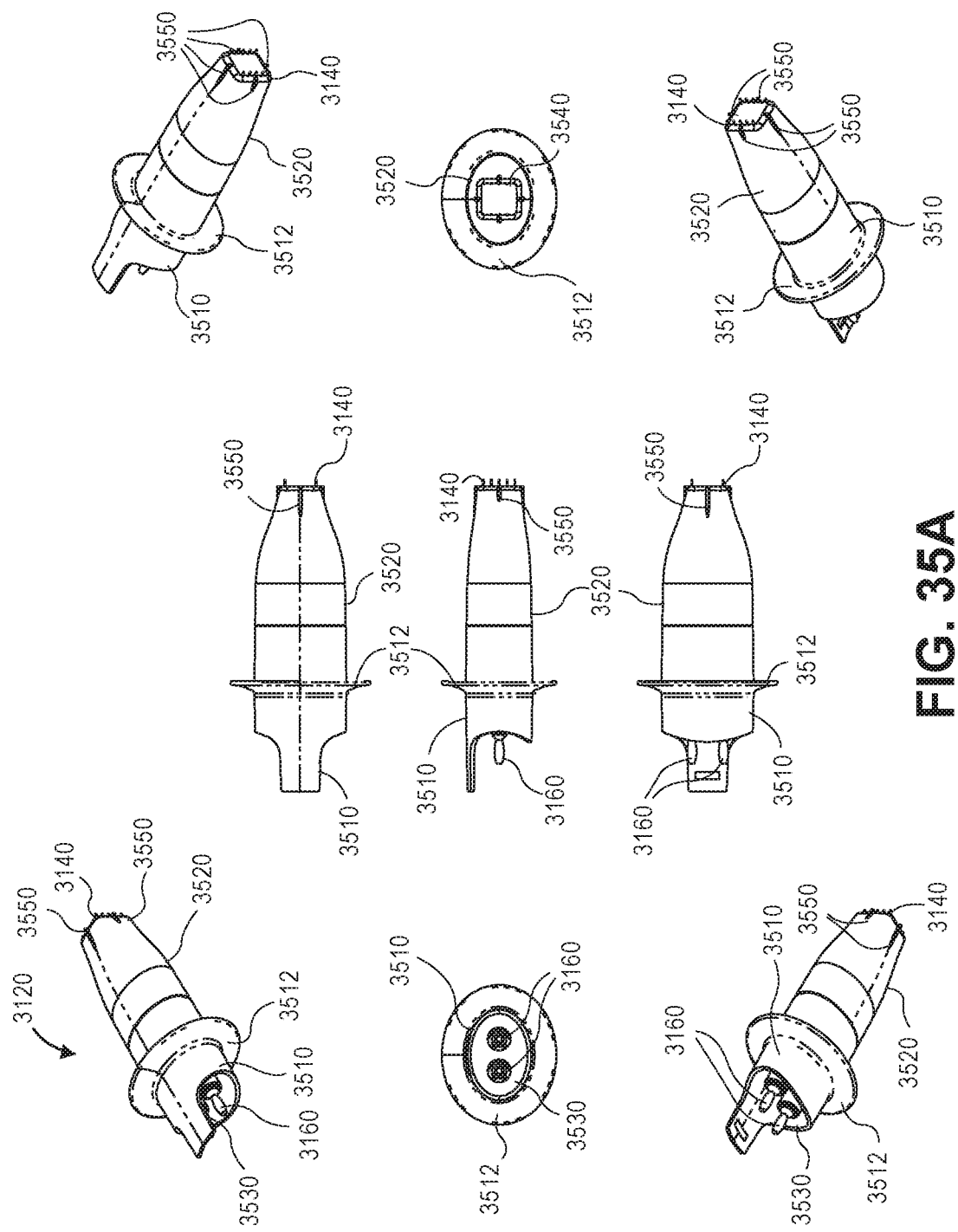
FIG. 35A illustrates an embodiment of a tip.

FIGS. 35A and 35B illustrate tip 3120. As shown, tip 3120 includes tip base 3510 and tip cap 3520. As shown, tip base 3510 and tip cap 3520 house wires 3590 which electrically connect connection terminals 3160 with therapeutic terminals 3140. When assembled, connection terminals 3160 protrude from tip base 3510 through holes 3580, wires 3590 extend through tip base wiring channels 3570 and tip cap wiring channels 3525, and therapeutic terminals 3140 extend through tip cap holes 3560. In some embodiments, one or more of the connection terminals 3160, wires 3590, and therapeutic terminals 3140 may be cemented in place, for example, with epoxy. In some embodiments, as part of the assembly process for tip 3120, tip base 3510 is cemented to tip cap 3520, for example, with epoxy.

As shown in FIG. 35B, tip base 3510 includes skirt holes 3515, which are configured to receive skirts 3517 of tip cap 3520 when tip base 3510 is connected with tip cap 3520. In alternative embodiments, tip cap 3520 has skirt holes configured to receive skirts of tip base 3510. In some embodiments each of tip cap 3520 and tip base 3510 have one skirt and one skirt hole, where the one skirt hole is configured to receive the skirt of the other of tip cap 3520 and tip base 3510. In some embodiments, a single skirt hole in either of tip cap 3520 and tip base 3510 is configured to receive both skirts of the other of tip cap 3520 and tip base 3510.

Because the voltage between therapeutic terminals 3140 can be very large, leakage may occur between therapeutic terminals 3140 along a path on a surface or combination of connected surfaces between therapeutic terminals 3140. At least to prevent or minimize the leakage, the skirts and skirt holes cause the distance between therapeutic terminals 3140 along any path on any surface or combination of surfaces is greater than a minimum distance. In some embodiments, the minimum distance is greater than 1, 1.25, 1.5, 1.75, 2, 2.5, 3, 4, 5, or more inches.

As shown in FIGS. 35A and 35B, tip base 3510 includes guard 3512. Guard 3512 serves at least to help ensure that a user's hand remains a minimum distance away from therapeutic terminals 3140. In some embodiments, the minimum distance is greater than 1, 1.25, 1.5, 1.75, 2, 2.5, 3, 4, 5, or more inches.

As shown in FIGS. 35A and 35B, tip base 3510 includes skirt hole 3530, which is configured to receive skirt 3130 of handle 3110 when tip 3120 is connected with handle 3110. In alternative embodiments, handle 3110 has skirt holes configured to receive skirts of tip 3510. In some embodiments each of handle 3110 and tip 3510 have one skirt and one skirt hole, where the one skirt hole is configured to receive the skirt of the other of handle 3110 and tip 3510. In some embodiments, a single skirt hole in either of handle 3110 and tip 3510 is configured to receive both skirts of the other of handle 3110 and tip 3510.

Because the voltage between connection terminals 3160 can be very large, leakage may occur between connection terminals 3160 along a path on a surface or combination of connected surfaces between connection terminals 3160. At least to prevent or minimize the leakage, the skirts and skirt holes cause the distance between connection terminals 3160 along any path on any surface or combination of surfaces is greater than a minimum distance. In some embodiments, the minimum distance is greater than 1, 1.25, 1.5, 1.75, 2, 2.5, 3, 4, 5, or more inches.

As shown in FIGS. 35A and 35B, tip cap 3520 includes fiducials 3550. Fiducials 3550 are radially aligned with a central point and may, for example, indicate a geometric center of the therapeutic terminals 3140 are particularly useful during therapeutic use of electrode 3100. For example, prior to use the desired location of treatment is determined and marked with perpendicular lines which intersect at the desired center point of treatment and which are long enough to extend beyond the electrode fiducials 3550 when the electrode 3100 is positioned for treatment. To properly place electrode 3100 for use on the desired location, the user of electrode 3100 places electrode 3100 such that fiducials 3550 align with the portion of the perpendicular lines which extend beyond the fiducials 3550 of electrode 3100.

Figure 36:
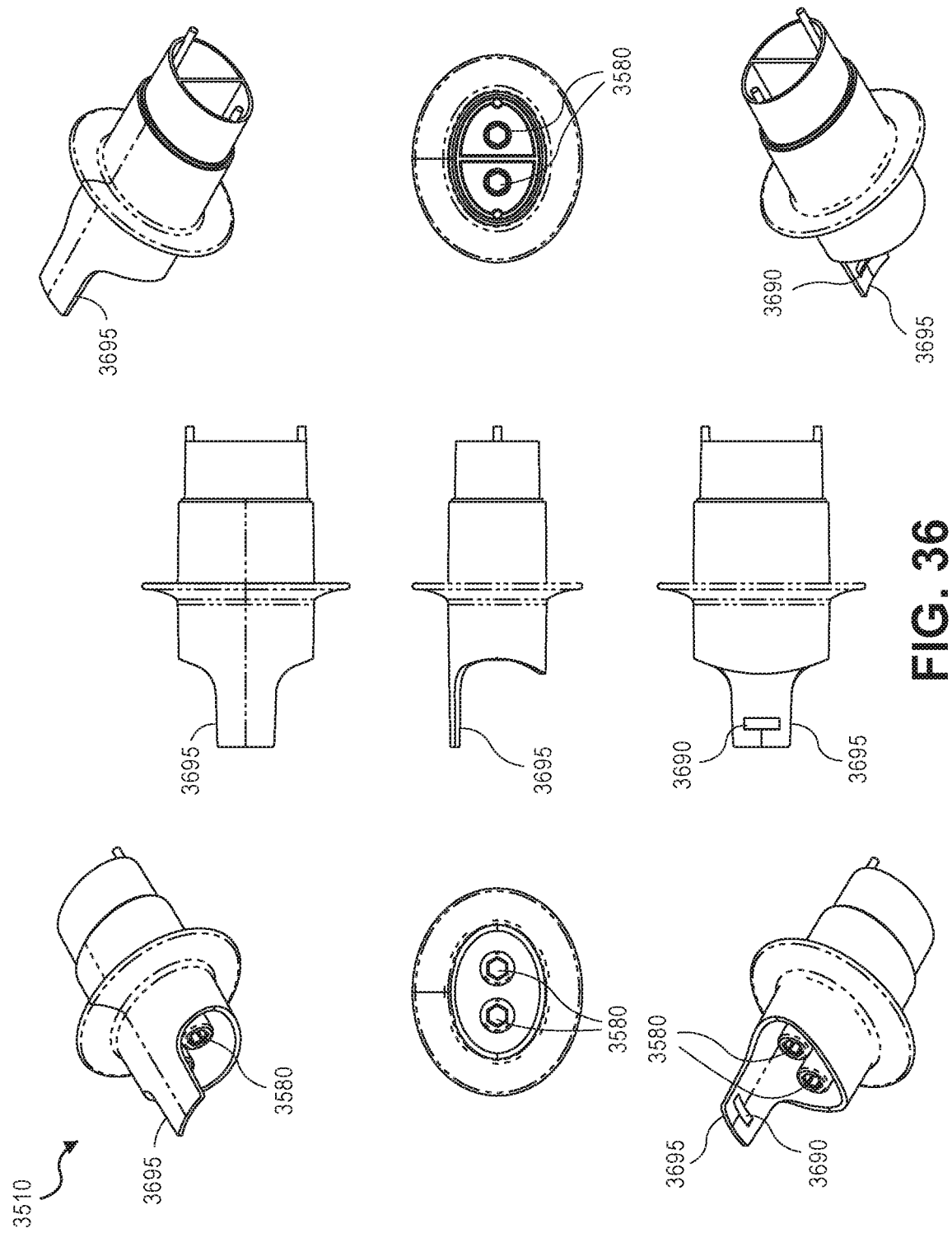
FIG. 36 illustrates an embodiment of a tip base.
Figure 38:
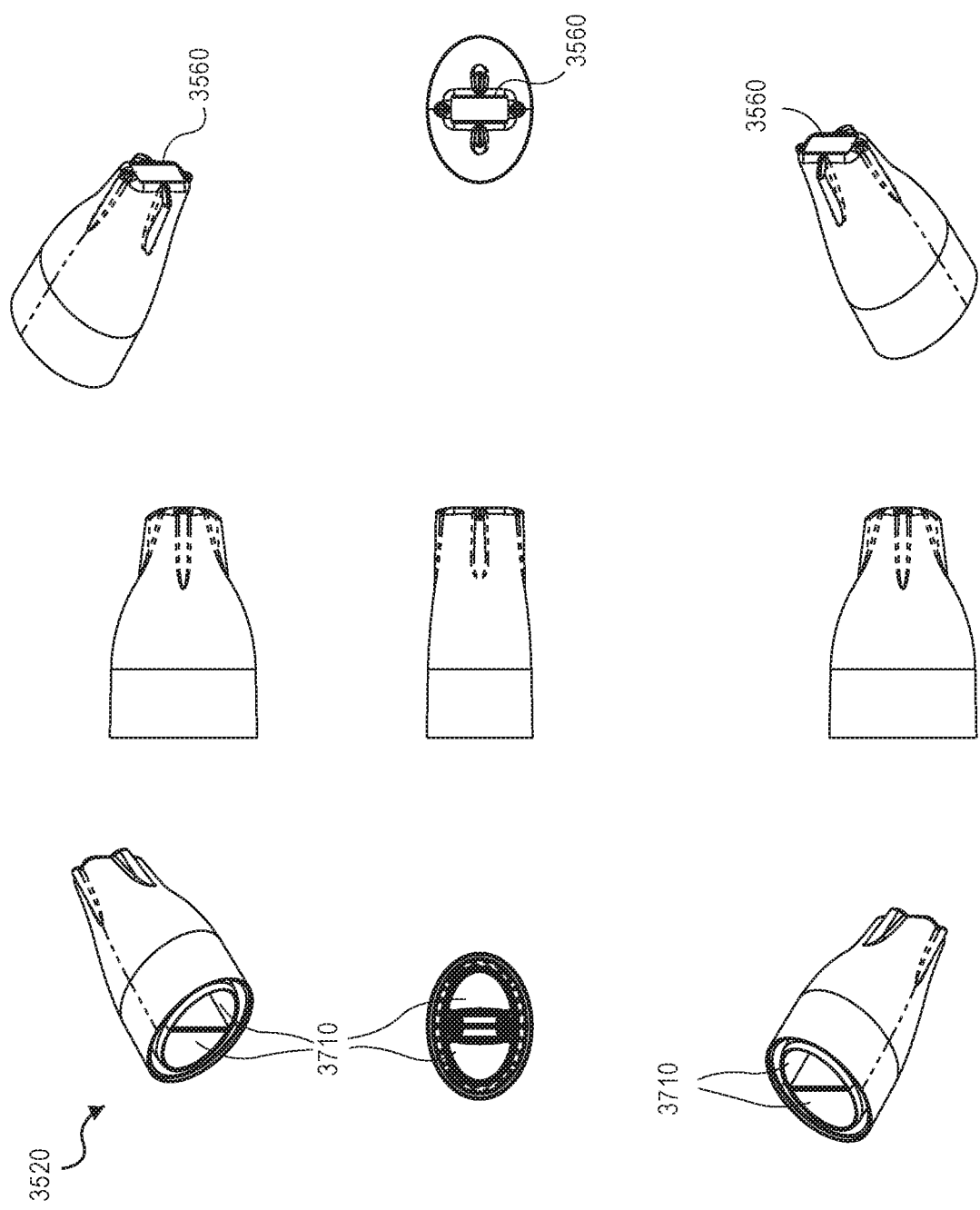
FIG. 38 illustrates an embodiment of a tip cap.
Figure 39:
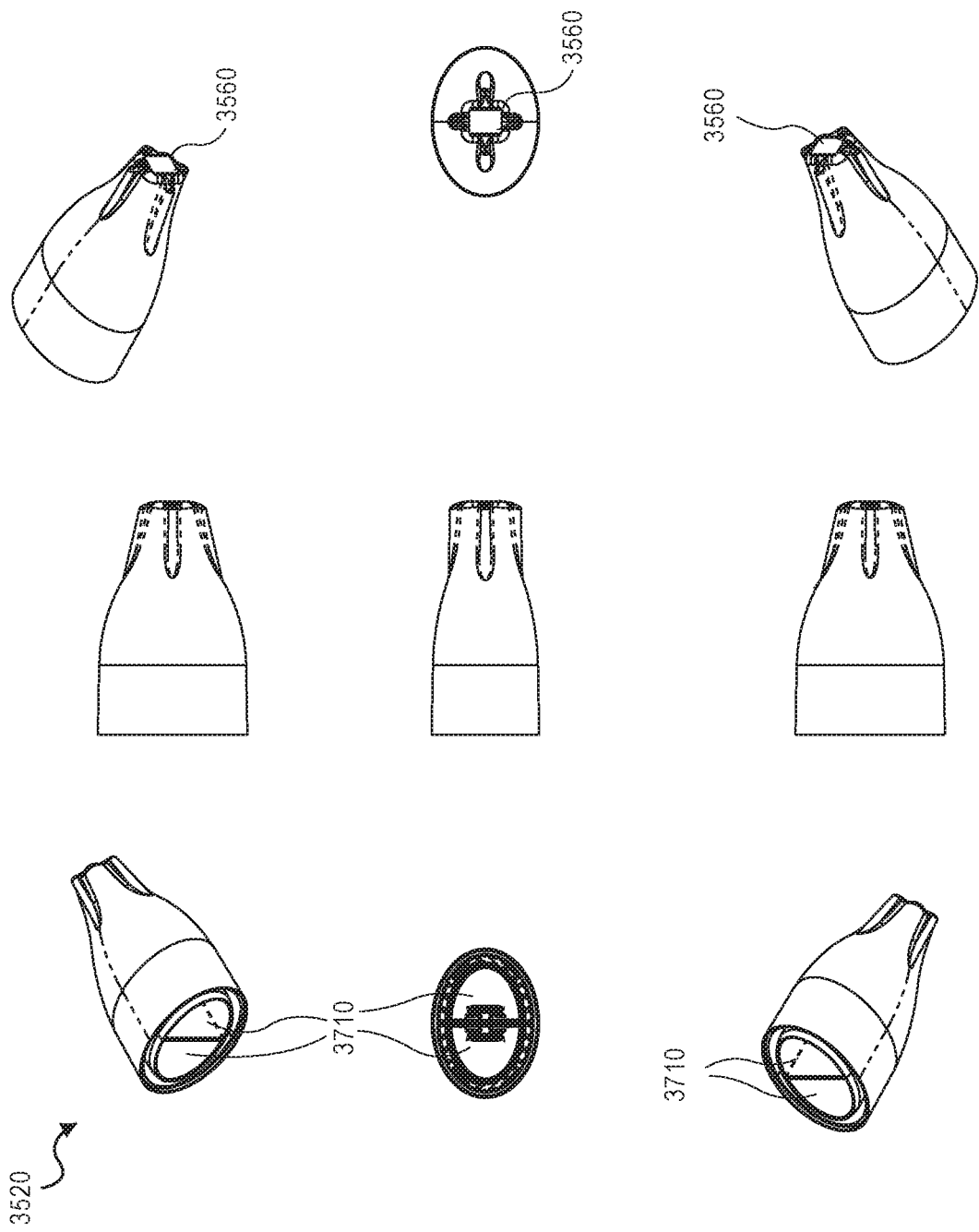
FIG. 39 illustrates an embodiment of a tip cap.
Figure 40:
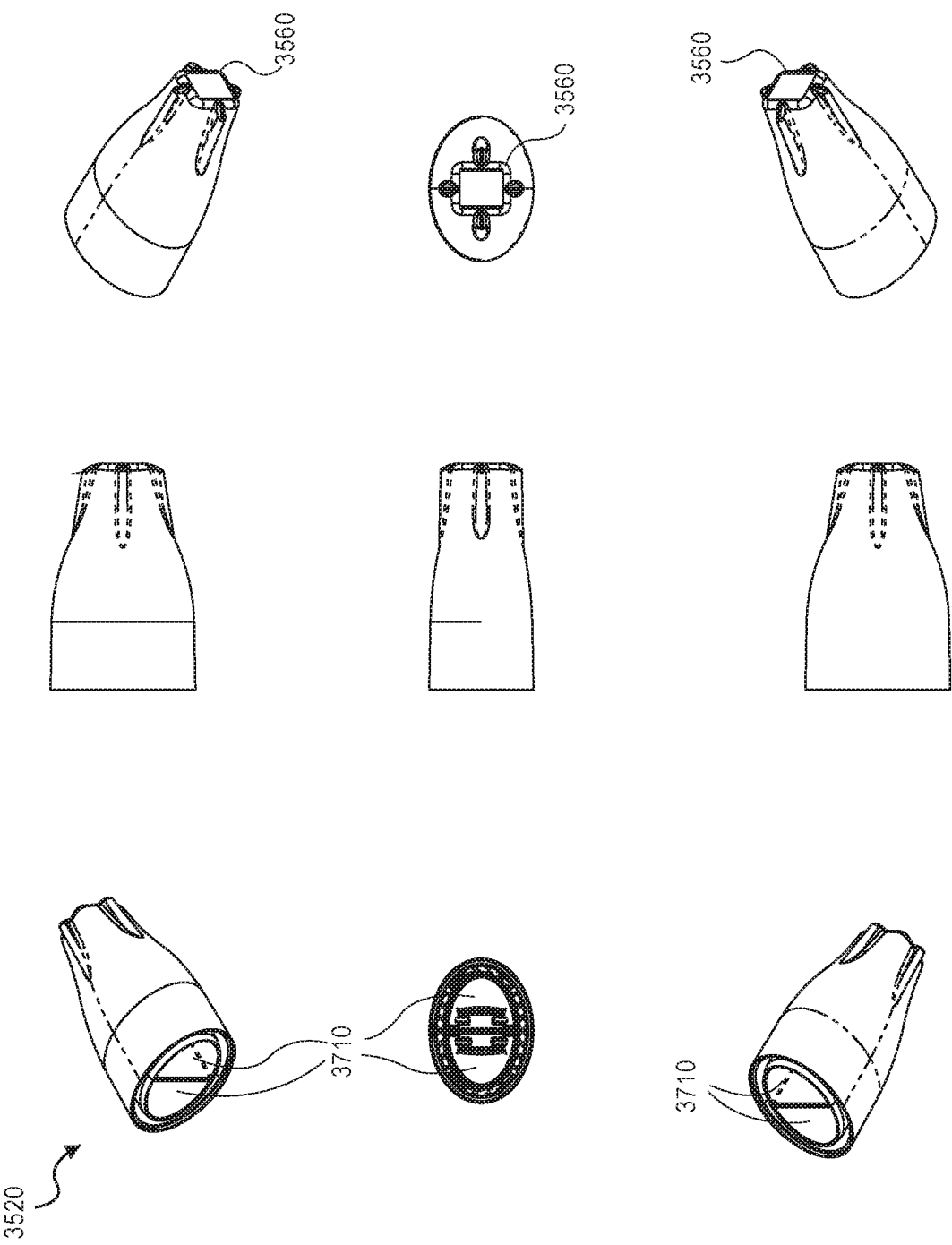
FIG. 40 illustrates an embodiment of a tip cap.
Figure 41:
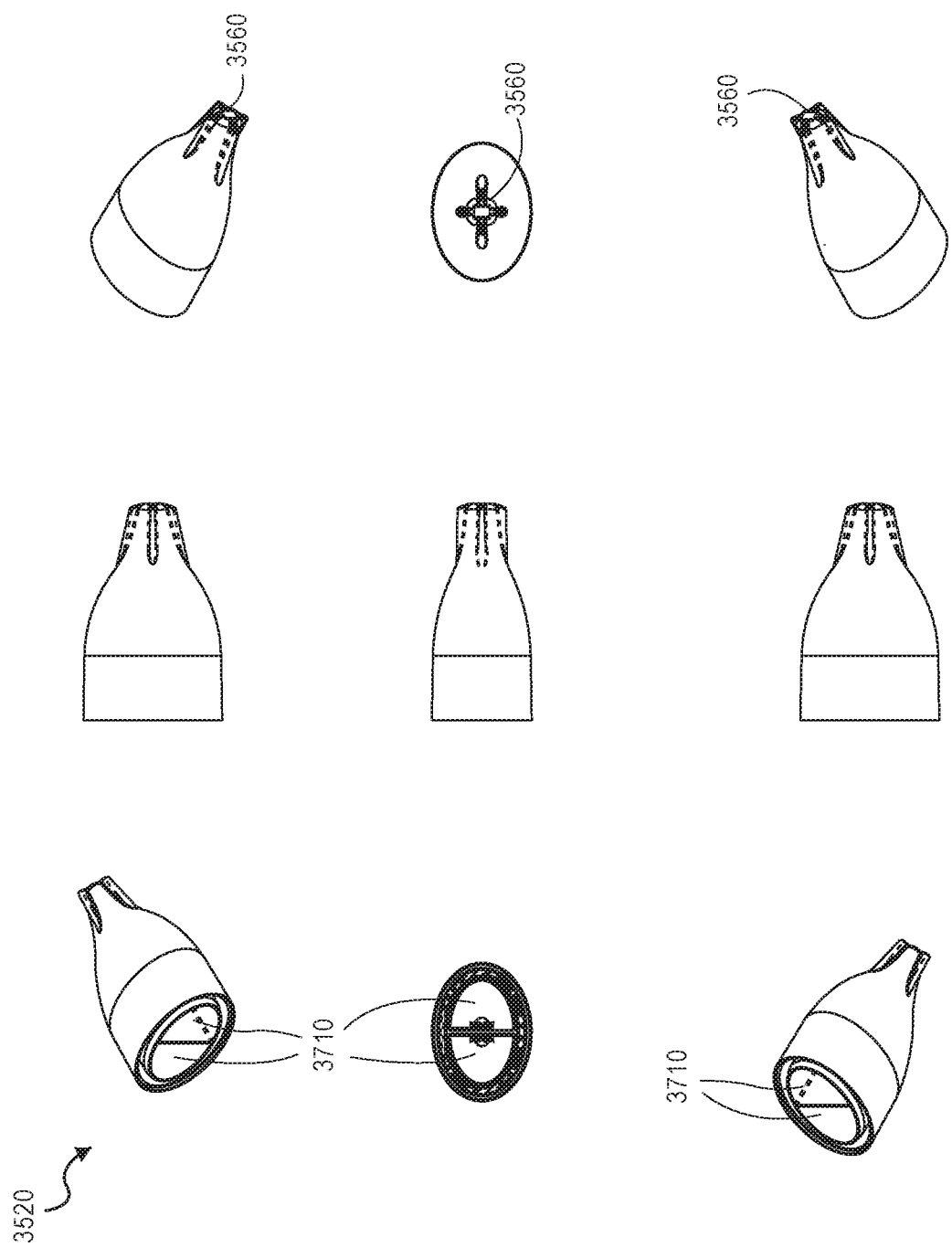
FIG. 41 illustrates an embodiment of a tip cap.

FIG. 36 illustrates tip base 3510. As shown, tip base 3510 includes tab 3695 which has latch notch 3690. Tab 3695 and latch notch 3690 are used to secure and to release the connection of tip 3120 and handle 3110. The connection of tip 3120 and handle 3110 is discussed in further detail below.

FIG. 37 illustrates tip cap 3520. As shown, tip cap 3520 includes holes 3710, which are openings in skirts 3517 to tip cap wiring channels 3525. In addition, tip cap 3520 includes therapeutic terminal holes 3560, through which therapeutic terminals 3140 extend, when tip 3120 is assembled. In this embodiment, tip cap wiring channels 3525 have cross-sectional geometries which correspond with the arrays of therapeutic terminals 3140. As a result, during assembly, when the therapeutic terminals 3140 are fed through tip cap 3520, the therapeutic terminals 3140 align with therapeutic terminal holes 3560 in tip cap 3520 because of the geometry of the therapeutic terminal arrays and the geometry of the tip cap wiring channels 3525. In addition, in this embodiment, therapeutic terminal holes 3560 collectively have geometric characteristics which correspond with corresponding embodiments of therapeutic terminals 3140.

FIGS. 38-41 illustrate various embodiments of tip cap 3520. As shown, the tip caps 3520 of these embodiments include holes 3710, which are openings to tip cap wiring channels 3525. In addition, tip caps 3520 of these embodiments include therapeutic terminal holes 3560, through which therapeutic terminals 3140 extend, when tip 3120 is assembled. In these embodiments, tip cap wiring channels 3525 have cross-sectional geometries which correspond with the arrays of therapeutic terminals 3140. As a result, during assembly, when the therapeutic terminals 3140 are fed through tip cap 3520, the therapeutic terminals 3140 align with therapeutic terminal holes 3560 in tip cap 3520 because of the geometry of the therapeutic terminal arrays and the geometry of the tip cap wiring channels 3525. In addition, in these embodiments, therapeutic terminal holes 3560 collectively have geometric characteristics which correspond with corresponding embodiments of therapeutic terminals 3140.

In some embodiments, the therapeutic terminal holes 3560 collectively have geometric characteristics which define a rectangle which is about 10 mm×10 mm. Alternatively, the therapeutic terminal holes 3560 may collectively have geometric characteristics which define a rectangle which is one of about 10 mm×5 mm, about 7.5 mm×5 mm, about 2.5 mm×5 mm, about 7.5 mm×7.5 mm, about 5 mm×10 mm, about 5 mm×5 mm, and about 2.5 mm×2.5 mm. Other geometric arrangements may alternatively be used.

Figure 42A:
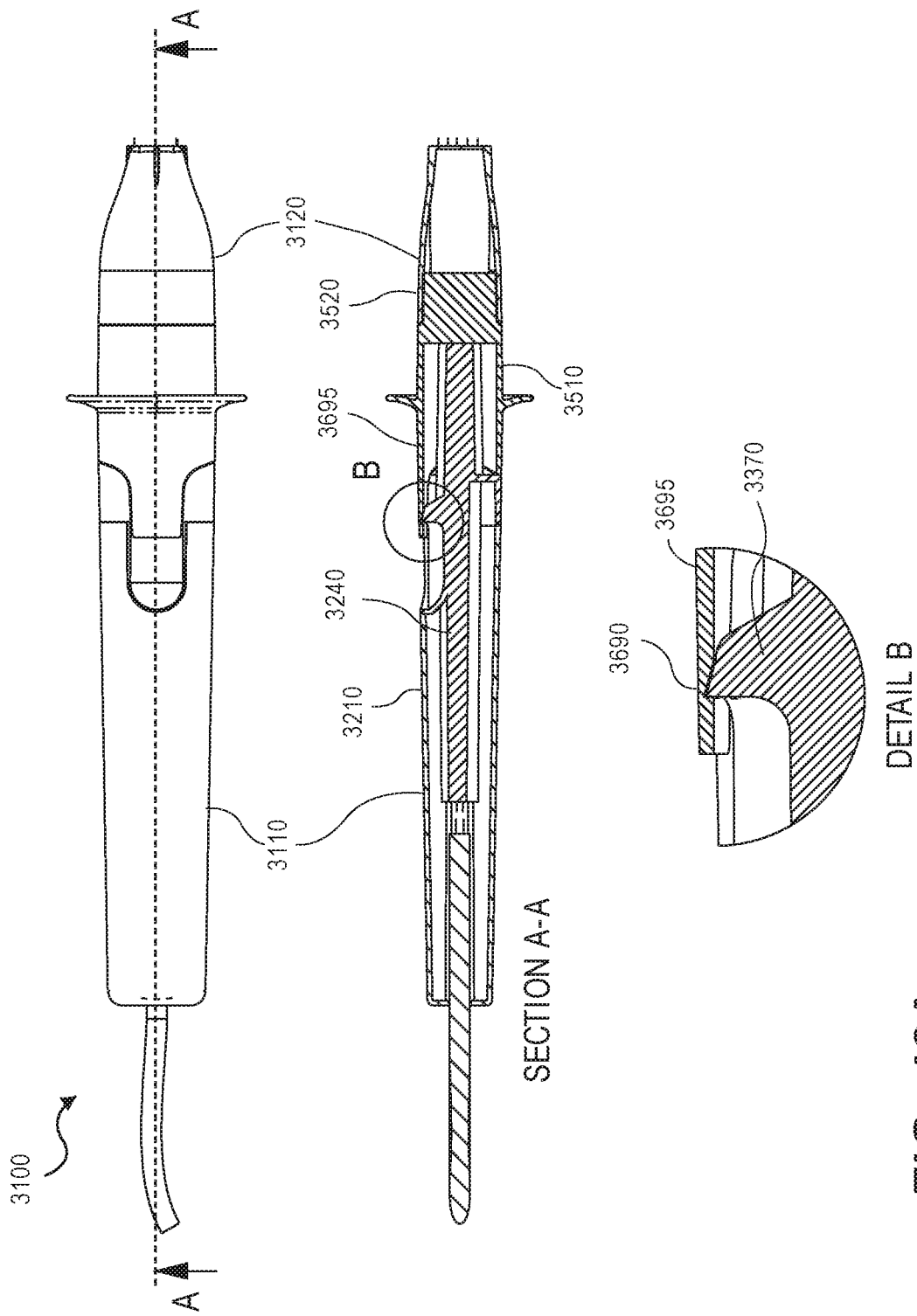
FIG. 42A illustrates an embodiment of an electrode.
Figure 42B:
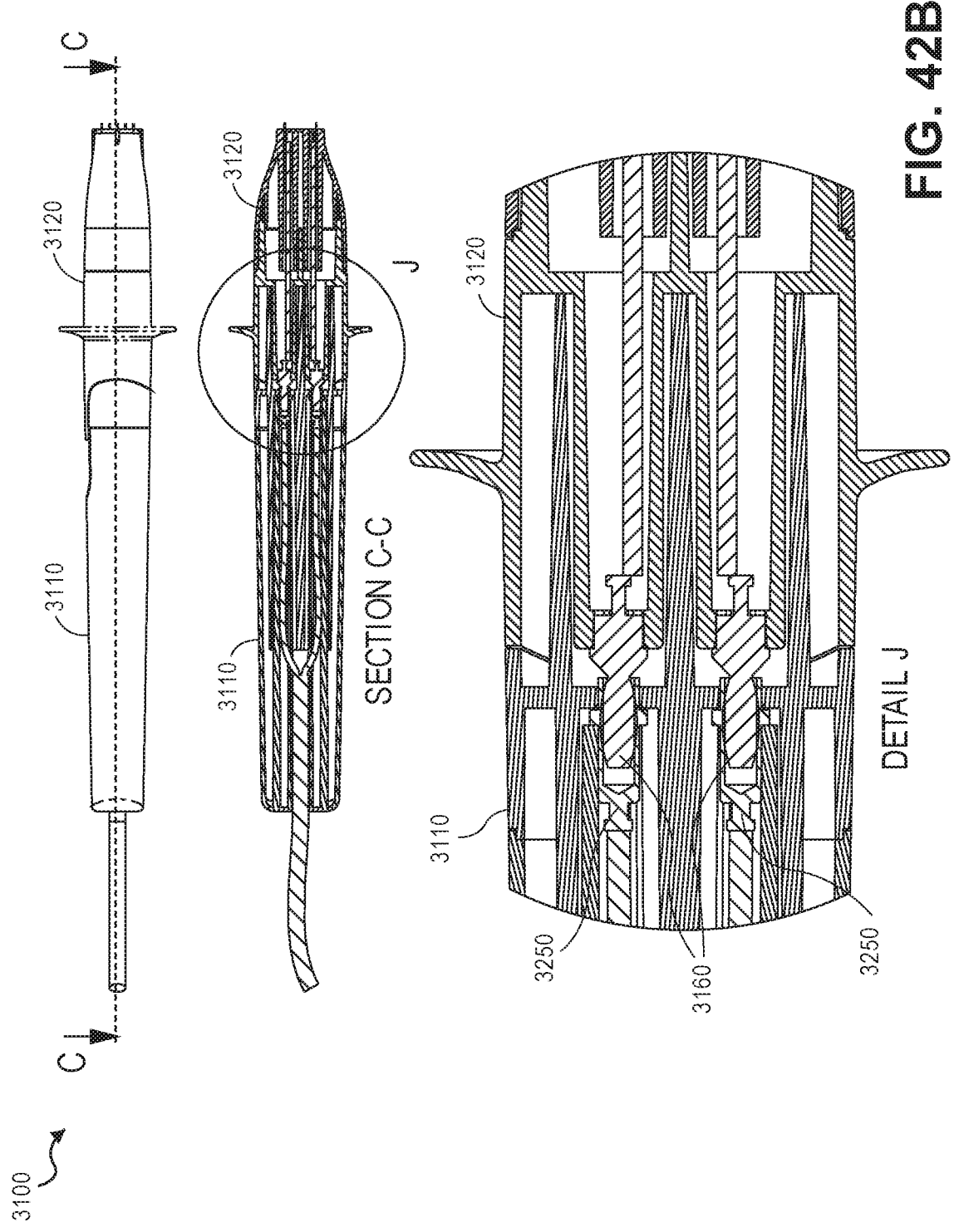
FIG. 42B illustrates an embodiment of an electrode.

FIGS. 42A and 42B illustrate electrode 3100 in an assembled state with tip 3120 connected with handle 3110. As shown, tip 3120, which includes tip base 3510 and tip cap 3520, is connected with handle 3110, which includes handle base 3210 and handle cap 3240. Tip 3120 is secured to handle 3110 by a latch which has latch hook 3370 of handle cap 3240 and latch notch 3690 in tab 3695 of tip base 3510. As shown in DETAIL B, latch hook 3370 is inserted in latch notch 3690 and prevents tip 3120 from detaching from handle 3110.

To release tip 3120 from handle 3110, a force is exerted on tab 3695 causing latch notch 3690 to move away from latch hook 3370, for example, by causing tab 3695 to flex. Once latch notch 3690 has moved enough that latch hook 3370 is no longer within latch notch 3690, a force exerted on tip 3120 may cause tip 3122 separate from handle 3110.

To connect tip 3120 to handle 3110, tip 3120 is pressed onto handle 3110. The pressing action causes latch hook 3372 engage latch notch 3690, for example, by causing tab 3695 to flex.

As shown in FIG. 42B, when handle 3110 is connected with tip 3120, connection terminals 3160 are mechanically and electrically connected with connectors 3250.

Figure 43:
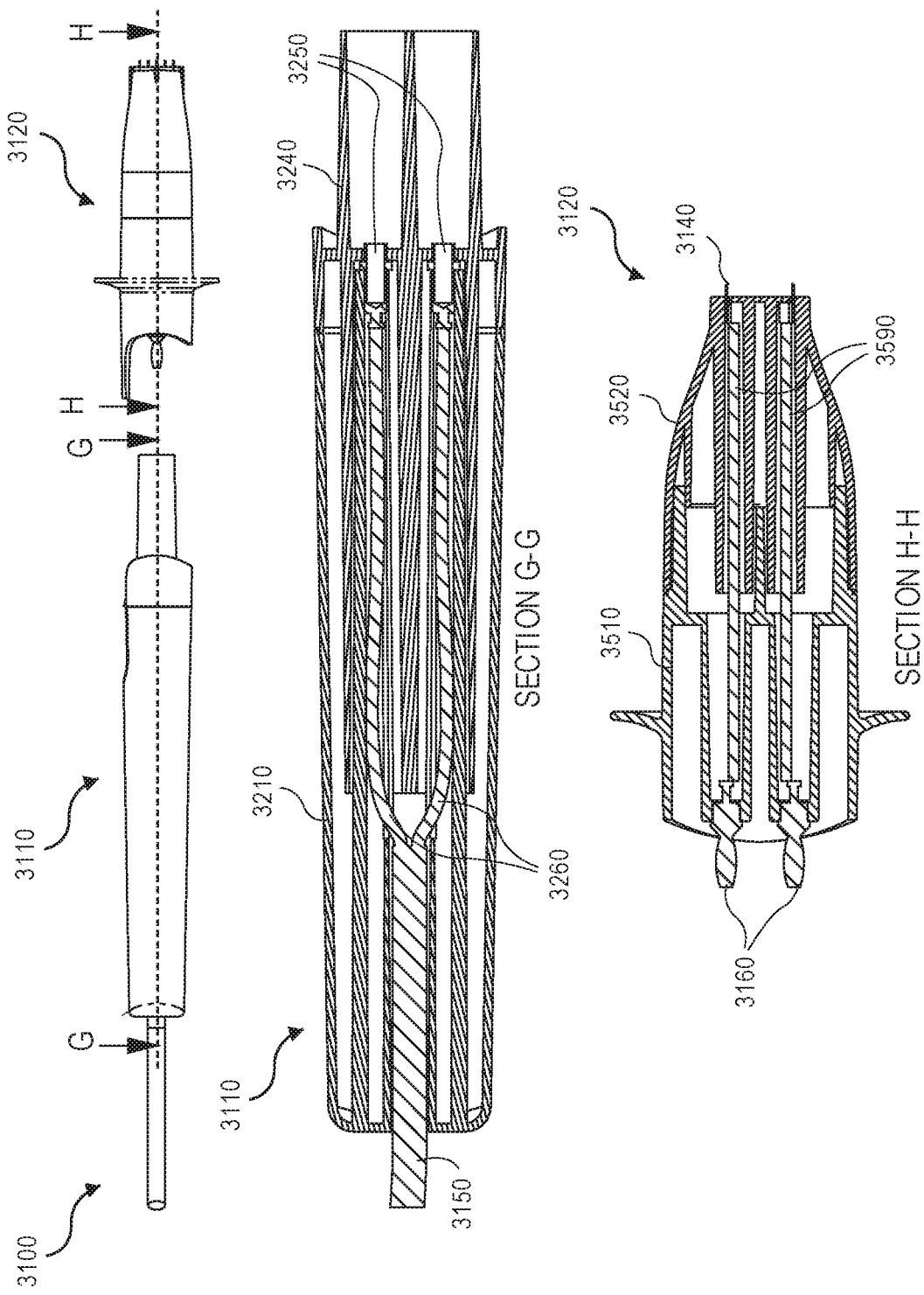
FIG. 43 illustrates an embodiment of an electrode.

FIG. 43 illustrates electrode 3100 in an assembled state with tip 3120 disconnected from handle 3110. As shown, handle 3110 includes handle base 3210 and handle cap 3240, which house connectors 3250, wires 3260, and a portion of cable 3150, such that connectors 3250 are accessible to connection terminals 3160 through handle cap 3240 when tip 3120 is connected with handle 3110. Also as shown, tip 3120 includes tip base 3510 and tip cap 3520, which house therapeutic terminals 3140, wires 3590, and connection terminals 3160, such that connection terminals 3160 connect with connectors 3250 when tip 3120 is connected with handle 3110.

As shown in FIG. 43 and in other figures, each component (e.g. tip base 3510, tip cap 3520, handle base 3210, and handle cap 3240) is mated to one or more adjacent components such that the uninsulated electrical terminals and connectors are housed within a skirt of one component which extends into a skirt hole of the adjacent component. As a result, current leakage between the uninsulated electrical terminals and or connectors is minimized or prevented or substantially prevented because the skirts and skirt holes cause the distance between the uninsulated electrical terminals and or connectors along any path on any surface or combination of surfaces is greater than a minimum distance. In some embodiments, the minimum distance is greater than 1, 1.25, 1.5, 1.75, 2, 2.5, 3, 4, 5, or more inches.

FIGS. 44A and 44B illustrate an embodiment of an alternative handle 3110A. In some embodiments, alternative handle 3110A has features similar or identical to those of handle 3110 and may be used in electrode 3100 instead of handle 3110, discussed above. Alternative handle 3110A includes alternative handle base 3210A and alternative handle cap 3240A. Alternative handle base 3210A has features similar or identical to those of handle base 3210. Alternative handle cap 3240A has features similar or identical to those of handle cap 3240.

In some embodiments, cable 3150 is a co-axial cable, having a central wire surrounded by an insulator and a shielding conductor surrounding the insulator. An outer insulated sheath also surrounds the shielding conductor. In such embodiments, splitting wires 3260 from co-axial cable 3150 may include removing the outer insulated sheath from an end portion of co-axial cable 3150, thereby exposing the shielding conductor along the end portion. In addition, some of the shielding conductor is also removed such that a short portion of the shielding conductor remains exposed and the insulator surrounding the central wire is exposed along the remainder of the end portion. As a result, the modified end portion includes a relatively long section of insulated central wire extending from a short portion of the exposed shielding conductor. Accordingly, a surface path between the connector 3250 of the insulated central wire and the exposed shielding conductor exists along the insulation of the insulated central wire. Accordingly, the relatively long section of insulated central wire should be at least a minimum distance. In some embodiments, the minimum distance is greater than 1, 1.25, 1.5, 1.75, 2, 2.5, 3, 4, 5, or more inches.

In the illustrated embodiment, the insulated central wire 3260A is circuitously routed from the exposed shielding conductor 3260B to the connector 3250 of the insulated central wire. This feature allows for the desired minimum distance along the surface leakage path between connectors 3250 to be achieved with alternative handle base 3210A being shorter than the desired minimum surface leakage path length.

In some embodiments, the distance between the shielding conductor 3260B and the hole in handle 3110A by which cable 3150 enters handle 3110A is greater than a minimum distance. In some embodiments, the minimum distance is greater than 1, 1.25, 1.5, 1.75, 2, 2.5, 3, 4, 5, or more inches. In some embodiments, a handle may be shorter than the minimum distance by a circuitous routing of the cable between the hole and shielding conductor 3260B, similar, for example, to the routing of insulated central wire 3260A illustrated in FIG. 44A.

Figure 45:
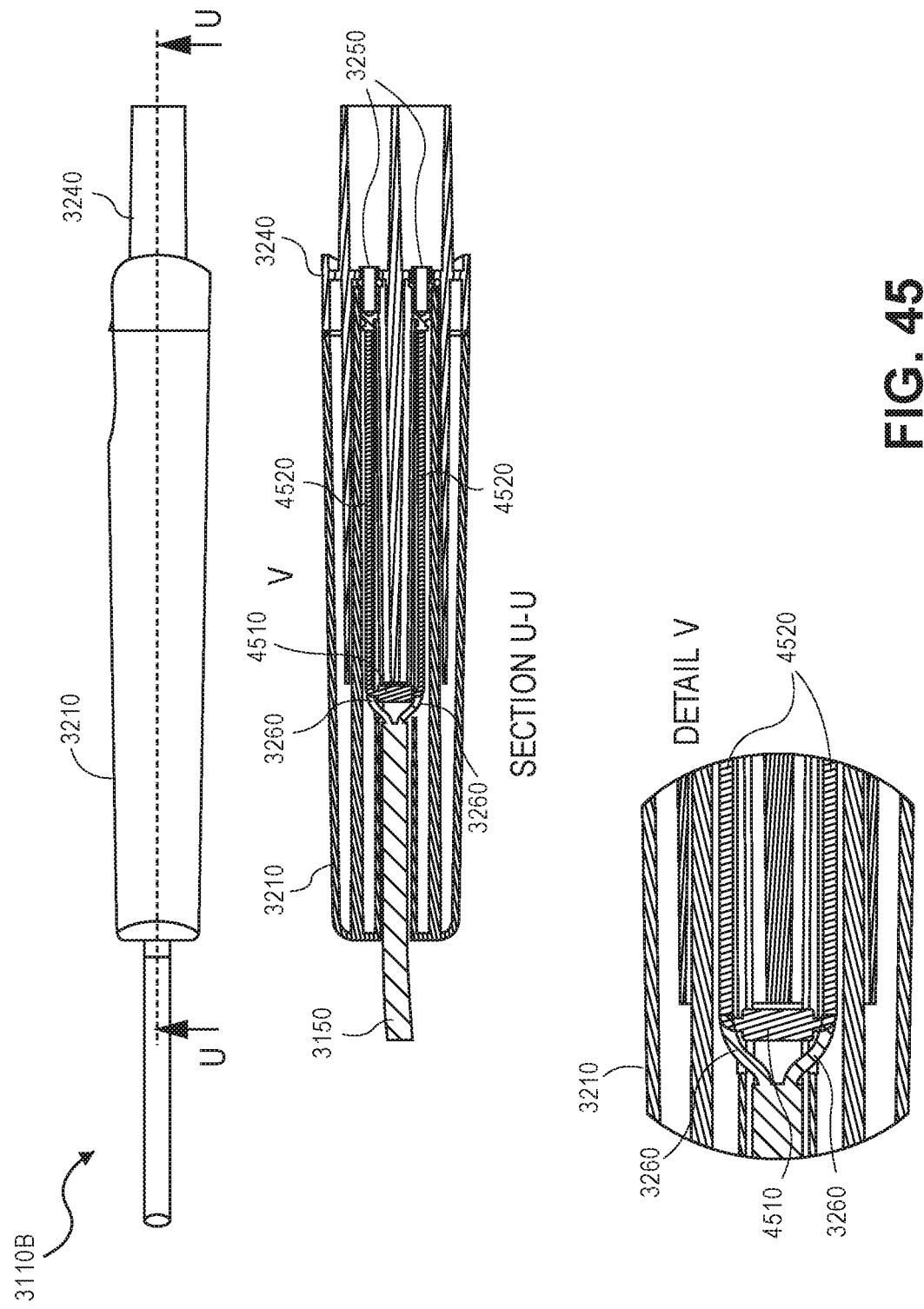
FIG. 45 illustrates an embodiment of a handle.

FIG. 45 illustrates an embodiment of an alternative handle 3110B. In some embodiments, alternative handle 3110B has features similar or identical to those of handle 3110 and may be used in electrode 3100 instead of handle 3110, discussed above. Alternative handle 3110B includes alternative handle base 3210B and alternative handle cap 3240B. Alternative handle base 3210B has features similar or identical to those of handle base 3210. Alternative handle cap 3240B has features similar or identical to those of handle cap 3240.

As shown, alternative handle base 3210B and alternative handle cap 3240B house connectors 3250, wires 3260, and a portion of cable 3150, such that connectors 3250 are accessible to connection terminals 3160 through alternative handle cap 3240B when tip 3120 is connected with alternative handle 3110B.

Alternative handle base 3210B also includes resistor 4510, which is connected with connectors 3250 by conductors 4520 and is, therefore electrically in parallel with a load to which the electrode is attached. Resistor 4510 advantageously ensures that the resistive load experienced by the pulse generator used with alternative handle 3110B is less than a predetermined maximum. For example, if the maximum desired resistance is 200 ohms, resistor 4510 may be 200 ohms. In alternative embodiments resistor 4510 may be 50 ohms, 75 ohms, 100 ohms, 500 ohms, 1000 ohms, or another value.

In some embodiments, the value of the resistor may correspond with a type of or an attribute of an electrode. For example, in embodiments of some systems, a resistor having a value between 100 ohms and 1000 ohms may be electrically adequate. In such systems, a resistor having a value of about 100 ohms may indicate an electrode of a first type and a resistor having a value of about 200 ohms may indicate an electrode of a second type. In some embodiments, the value of the resistor may be sensed by a controller, and nsPEF pulse parameters to be delivered using the electrode may be determined according to the sensed resistor value. In some embodiments, the type or attribute may be related to distance between therapeutic terminals, number of therapeutic terminals, type of therapeutic terminal, or another characteristic.

In some embodiments, a series resistor (not shown) may be placed so as to be electrically in series with the load. The resistor may be, for example, placed between a wire and a connector or may be spliced into a wire such that the electrode is configured to conduct current to or from the load through the resistor. In some embodiments, the resistor is placed elsewhere.

The series resistor guarantees a minimum impedance, and may, for example, be beneficial in improving a shape of the nsPEF pulses delivered by the electrode. In some embodiments, the series resistor may be about 50 ohms, about 75 ohms, about 100 ohms, about 200 ohms, about 500 ohms, about 1000 ohms, or another value.

FIG. 46 is an illustration of a connector 4600. Connector 4600 may, for example, be used in nsPEF system 100 to connect electrode 102 to housing 105. When mated, connector 4600 electrically connects electrode 102 with the electronic components internal to housing 105, such as an nsPEF pulse generator. Connector 4600 includes features similar to or identical to those of the other connectors discussed herein, such as connectors 2700 and 2900 discussed above.

As shown, connector 4600 electrically connects cable 4630 with connection terminals 4610 through wires 4620. Connector 4600 also includes resistor 4650, which is connected with connection terminals 4610 by conductors 4640. Resistor 4650 advantageously ensures that the resistive load experienced by connected the nsPEF pulse generator is less than a predetermined maximum. For example, if the maximum desired resistance is 200 ohms, resistor 4650 may be 200 ohms. In alternative embodiments resistor 4650 may be 50 ohms, 75 ohms, 100 ohms, 500 ohms, 1000 ohms, or another value.

In some embodiments, resistor 4650 includes circuitry configured to interface with a controller. For example, the controller may identify the connector 4600 or an electrode connected to the connector 4600 as a result of the controller receiving identifying information from the circuitry. In some embodiments, the circuitry may be configured to count and store the number of nsPEF pulses delivered through the connector 4600.

Applying nsPEF to a tumor sufficient to stimulate apoptosis may include at least the electrical characteristics found experimentally. For example, a 100 ns long pulse with a 20 ns rise time to 30 kV/cm (kilovolts per centimeter) at 1 to 7 pulses per second (pps) for 500 to 2000 pulses has been found to be sufficient to stimulate apoptosis, depending on the tumor type. Pulsed electric fields of at least 20 kV/cm have been shown to be effective. A number of pulses greater than 50 pulses has also been shown to be effective. Current values between 12 A and 60 A resulted, depending on the electrode type and skin resistance.

The embodiments of pulse generators described herein have many uses. Cancer that has metastasized through a subject's bloodstream may be treated using nsPEF's immune stimulation properties. For treatment, circulating tumor cells (CTCs) are isolated from the bloodstream and amassed in vial, test tube, or other suitable in vitro environment. In some cases, there may only be a few (e.g., 5, 10), tumor cells that are collected and amassed. Through this mass, an nsPEF electric field is applied in order to treat the cells. This may cause calreticulin or one or more other damage-associated molecular patterns (DAMPs) to be expressed on the surface membranes of the tumor cells. The tumor cells may then be introduced back into the subject's bloodstream by injection, infusion, or otherwise.

In an alternative embodiment, single CTCs may also be isolated from the bloodstream, and each tumor cell treated individually. An automated system that captures CTCs in whole blood using iron nanoparticles coated with a polymer layer carrying biotin analogues and conjugated with antibodies for capturing CTCs can automatically capture the tumor cells, and a magnet and or centrifuge can separate them. After separation from the antibodies, the CTCs may be treated with nsPEF through a small capillary and then reintroduced to the patient's bloodstream.

While examples in the application discuss human and murine subjects, the treatment of other animals is contemplated. Agricultural animals, such as horses and cows, or racing animals, such as horses, may be treated. Companion animals, such as cats and dogs, may find special use with the treatments described herein. It may be difficult for a veterinarian to remove many tumors from a small animal, and cancers may be caught relatively late because the animals cannot communicate their advancing pain. Further, the risk inherent in reinjecting tumor cells—albeit treated tumor cells—may be worth the potential benefits of potentially halting a metastasized cancer in a loved pet.

The methods of the present invention can be used for the treatment of any type of cancer, whether characterized as malignant, benign, soft tissue, or solid, and cancers of all stages and grades including pre- and post-metastatic cancers. Examples of different types of cancer include, but are not limited to, digestive and gastrointestinal cancers such as gastric cancer (e.g., stomach cancer), colorectal cancer, gastrointestinal stromal tumors, gastrointestinal carcinoid tumors, colon cancer, rectal cancer, anal cancer, bile duct cancer, small intestine cancer, and esophageal cancer; breast cancer; lung cancer; gallbladder cancer; liver cancer; pancreatic cancer; appendix cancer; prostate cancer, ovarian cancer; renal cancer (e.g., renal cell carcinoma); cancer of the central nervous system; skin cancer (e.g., melanoma); lymphomas; gliomas; choriocarcinomas; head and neck cancers; osteogenic sarcomas; and blood cancers.

Electrical characteristics of nsPEF treatments can be adjusted based on a size and/or a type of a tumor. Types of tumors may include tumors of different regions of the body, such as the cancerous tumors described above.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

As noted previously, all measurements, dimensions, and materials provided herein within the specification or within the figures are by way of example only.

A recitation of "a," "an," or "the" is intended to mean "one or more" unless specifically indicated to the contrary. Reference to a "first" component does not necessarily require that a second component be provided. Moreover reference to a "first" or a "second" component does not limit the referenced component to a particular location unless expressly stated.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

What is claimed is:

1. An electrode electrically connectable to a pulse generator, wherein the electrode is configured to deliver a pulse generated by the pulse generator to a patient, and wherein the electrode comprises:
    a handle comprising:
        a handle skirt comprising a first hole and a second hole, and
        a first connection terminal within the first hole and a second connection terminal within the second hole of the handle skirt, the first and second connection terminals each comprising an uninsulated portion, the uninsulated portion of the first connection terminal coupled to a first insulated conductor and the uninsulated portion of the second connection terminal coupled to a second insulated conductor; and
    a tip, connected to the handle, wherein the tip includes a tip base having first and second insulative wiring channels, the tip further comprises:
        a plurality of therapeutic terminals,
        first and second connectors configured to electrically connect with the first and second connection terminals of the handle while the tip is connected to the handle, wherein:
            the first and second connectors are configured to electrically couple to the plurality of therapeutic terminals,
            each of the first and second connectors are electrically conductive,
            the first connector is received within the first insulative wiring channel of the tip base of the tip, and
            the second connector is received within the second insulative wiring channel of the tip base, and
        a tip skirt hole configured to receive the handle skirt while the tip is connected to the handle such that the first connector and at least a portion of the first insulative wiring channel are received into the first hole of the handle skirt, and the second connector and at least a portion of the second insulative wiring channel are received into the second hole of the handle skirt,
    wherein the handle skirt and the first and second holes of the handle skirt are configured and sized to cause a distance between the uninsulated portions of the first and second connection terminals along every and any path on any surface or combination of surfaces to be greater than a minimum distance to prevent or minimize current leakage while the tip is connected to the handle.

2. The electrode of claim 1, wherein the tip is removably connected to the handle.

3. The electrode of claim 2, further comprising:
    a latch comprising a latch hook and a latch notch, the latch removably connecting the handle to the tip.

4. The electrode of claim 1, wherein the tip further comprises a guard configured to maintain a user's hand a minimum user distance away from the therapeutic terminals.

5. The electrode of claim 1, further comprising:
    a cable having the first insulated conductor and the second insulated conductor extending therefrom, wherein the cable is electrically connected with the first connection terminal by the first insulated conductor and the cable is electrically connected with the second connection terminal by the second insulated conductor, and wherein the cable is connectable to the pulse generator.

6. The electrode of claim 5, wherein a first portion of the second insulated conductor is routed from the cable away from the second connection terminal and a second portion of the second insulated conductor is routed from the first portion toward the second connection terminal such that the handle is configured to be shorter than the minimum distance.

7. The electrode of claim 5, wherein the handle further comprises first and second bosses, wherein the first insulated conductor extends from the cable to the first connection terminal through the first boss, wherein the second insulated conductor extends from the cable to the second connection terminal through the second boss, wherein the first boss includes a first slot extending along a side of the first boss, and wherein the second boss includes a second slot extending along a side of the second boss.

8. The electrode of claim 1, further comprising a resistor electrically connected to the first and second connection terminals.

9. The electrode of claim 8, wherein the resistor has a value corresponding with an attribute of the electrode.

10. The electrode of claim 1, further comprising a resistor electrically connected to one of the first and second connection terminals, wherein the electrode is configured to conduct current to or from one of the therapeutic terminals through the resistor.

11. The electrode of claim 1, further comprising a plurality of fiducials radially aligned with a geometric center of the therapeutic terminals.

12. The electrode of claim 1, wherein the minimum distance is 2.5 cm or greater.

13. The electrode of claim 1, wherein a voltage is adapted to be applied between the connection terminals between about 5 kV and 30 kV and the minimum distance is based at least in part on an expected voltage between the connection terminals.

14. An electrode configured to deliver high voltage sub-microsecond pulses, the electrode comprising:
a handle comprising:
a handle skirt comprising a first hole and a second hole;
a first connection terminal accessible through the first hole; and
a second connection terminal accessible through the second hole;
a tip configured to couple to the handle, the tip including a tip base having first and second insulative wiring channels, the tip further comprising:
a tip skirt hole configured to receive the handle skirt;
a first connector electrically conductive and comprising an uninsulated portion, the first connector received within the first insulative wiring channel of the tip base of the tip, and wherein the first connector and at least a portion of the first insulative wiring channel are received by the first hole of the handle skirt and electrically connectable to the first connection terminal; and
a second connector electrically conductive and comprising an uninsulated portion, the second connector is received within the second insulative wiring channel of the tip base, and wherein the second connector and at least a portion of the second insulative wiring channel are received by the second hole of the handle skirt and electrically connectable to the second connection terminal; and
a plurality of therapeutic terminals configured to electrically couple to the first connector and second connector of the tip, the plurality of therapeutic terminals configured to deliver the high voltage sub-microsecond pulses to a patient,
wherein the handle skirt and the tip are configured and sized to cause a distance between the uninsulated portions of the first and second connectors along every and any path on any surface or combination of surfaces to be greater than a minimum distance to prevent or minimize current leakage.

15. The electrode of claim 14, wherein the first connector and the second connector are physically connected to the first connection terminal and the second connection terminal, respectively.

16. The electrode of claim 14, wherein the tip is removably coupled to the handle.

17. The electrode of claim 14, further comprising:
a latch, wherein the tip is locked to the handle by the latch.

18. The electrode of claim 14, wherein the tip further comprises a guard at a user minimum distance from the therapeutic terminals, the user minimum distance greater than a threshold value.

19. The electrode of claim 14, wherein the handle further comprises a resistor electrically connected to the first connection terminal and the second connection terminal.

20. The electrode of claim 14, wherein the tip further comprises a plurality of fiducials radially aligned with a geometric center of the therapeutic terminals.

21. The electrode of claim 14, wherein a distance between the first and second connection terminals along any path on any surface or combination of surfaces is greater than the minimum distance.

22. The electrode of claim 14, wherein the minimum distance is at least 2.5 cm.

23. The electrode of claim 14, wherein the electrode is configured to deliver the high voltage sub-microsecond pulse having voltage of five thousand (5000) volts or greater.

24. The electrode of claim 1, wherein the first insulated conductor is circuitously routed from the uninsulated portion of the first connection terminal to the uninsulated portion of the second connection terminal such that a length of the handle is less than the minimum distance.

25. The electrode of claim 14, wherein a voltage is adapted to be applied between the connectors between about 5 kV and 30 kV and the minimum distance is based at least in part on an expected voltage between the connectors.

* * * * *